(12) United States Patent
Green et al.

(10) Patent No.: US 7,612,065 B2
(45) Date of Patent: Nov. 3, 2009

(54) INHIBITORS OF C-JUN N-TERMINAL KINASES (JNK)

(75) Inventors: Jeremy Green, Waltham, MA (US); Susanne Wilke, Norwich, CT (US); Francesco Salituro, Marlborough, MA (US); Edmund Harrington, Plymouth, MA (US); Jingrong Cao, Newton, MA (US); Guy Bemis, Arlington, MA (US); Huai Gao, Arlington, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/729,420

(22) Filed: Mar. 28, 2007

(65) Prior Publication Data

US 2008/0033022 A1     Feb. 7, 2008

(51) Int. Cl.
 A61K 31/535  (2006.01)
 A61K 31/445  (2006.01)
 A61K 31/44   (2006.01)
 A61K 31/405  (2006.01)
 C07D 413/12  (2006.01)
 C07D 401/12  (2006.01)
 C07D 211/22  (2006.01)
 C07D 213/26  (2006.01)
 C07D 209/34  (2006.01)

(52) U.S. Cl. .............. 514/231.5; 514/320; 514/415; 514/416; 544/143; 546/196; 546/197; 546/258; 548/469; 548/483; 548/484; 548/486; 548/491

(58) Field of Classification Search ............. 514/231.5, 514/320, 415, 416; 544/143; 546/197, 258; 548/469, 483, 484, 486, 491
See application file for complete search history.

(56) References Cited

U.S. PATENT DOCUMENTS 5,849,710 A    12/1998    Battistini et al.

FOREIGN PATENT DOCUMENTS

| EP | 0685463 A1 | 12/1995 |
|---|---|---|
| WO | 94/18194 | 8/1994 |
| WO | 96/16046 | 5/1996 |
| WO | 99/01449 | 1/1999 |
| WO | 99/51590 | 10/1999 |
| WO | 99/65875 A1 | 12/1999 |

OTHER PUBLICATIONS

Bozyczko-Coyne D et al. "Targeting the JNK pathway for therapeutic benefit in CNS disease", Curr Drug Target CNS Neurol Disord. Feb. 2002; 1 (1): 31-49.
Tran, Viet Hung; Nguyen, Quang Dat; Pham, Minh Thuy, Tap Chi Duoc Hoc (12), 10-12 (Vietnamese) 2000, cited in Chemical Abstracts 2001: 349350.
Tran, Viet Hung; Nguyen, Quang Dat; Pham, Minh Thuy, Tap Chi Duoc Hoc (5), 14-16 (Vietnamese) 2000, cited in Chemical Abstracts 2000: 692850.
Zhavrid, S.V., et al., "Synthesis of Indole Derivatives and Their Antimicrobial Activitiy", Chemical Abstract, 99(9), Aug. 29, 1983, Columbus, OH, Abstract No. 70513n.
Khim. -Farm. ZH., vol. 17, No. 2, (1983) pp. 153-158, anmd Database Chemical Abstracts 'Online' CA 99:70513.
Abramenko, P.I., et al. "Synthesis of Substituted Indolothiazoles and Thienothiazoles", Chemical Abstract, vol. 90, No. 19, May 7, 1979, Columbus, OH, abstract No. 152060r.
Zh. Vses. Khim. O.V.A., vol. 23, No. 6 (1978), pp. 711-712, and Database Chemical Abstracts 'Online' CA 90:152060.
Santilli, A.A., et al., "7-Deazapurines VI. Syntheses and reactions of 5, 7-dihydro-4-methyl-2-phenyl-7-substitute d-6H-pyrrolo (2,3-d) pyrimidin-6-ones", J. Heterocyclic Chem., 13:135-137 (1976).
Plana, F., et al., "N-Ethanol-beta-isatoxime", Chemical Abstract, 80(6) (1974).
Plana, F., et al., Chemical Abstract, Cryst. Struct. Commun., 2(4): 613-617, (1973).
Miravitlles, C., et al., "Determination of hydrogen bonds in organic compounds by x-ray diffraction", 82(23), Chemical Abstract, (1975).
Miravitlles, C., et al., Chemical Abstract, Circ. Farm., 32(245): 613-622, Database Chemical Abstracts (1974).
Hirose, N, et al., "Benzoheterocyclic derivatives. Xl. Synthesis and pharmacological actions of indoline derivatives", 76 (9), Chemical Abstract, (1972).
Zasshi, Y., Chemical Abstract, 91(12):1323-1334, Database Chemical Abstracts (1971).
Izquierdo, A., et al., "Analytical applications of N-substituted beta-isatin oximes", Chemical Abstracts (1971).
Izquierdo, A., et al., Abstract. Inform Quim. Anal., 23(6): 161-168(1969).
Ludvik, D., Analytically important reactions of isatin oximes:, Chemical Abstracts, 73(2) (1970).
Ludvik, D., Abstract, Sb. Vys. Sk. Chem.-Technol. Praz, Anal. Chem. 3:85-112 (1968).
Homes et al., Gastroenterology Jan. 2002, 122 (1) pp. 7-14.

*Primary Examiner*—James O Wilson
*Assistant Examiner*—Ebenezer Sackey
(74) *Attorney, Agent, or Firm*—Jennifer G. Che

(57) ABSTRACT

The present invention relates to inhibitors of JNK, a mammalian protein kinase involved cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

22 Claims, No Drawings

INHIBITORS OF C-JUN N-TERMINAL KINASES (JNK)

TECHNICAL FIELD OF INVENTION

The present invention relates to inhibitors of c-Jun N-terminal kinases (JNK), which are members of the mitogen-activated protein (MAP) kinase family. There are a number of different genes and isoforms which encode JNKs. Members of the JNK family regulate signal transduction in response to environmental stress and proinflammatory cytokines and have been implicated to have a role in mediating a number of different disorders. The invention also relates to methods for producing these inhibitors. The invention also provides pharmaceutical compositions comprising the inhibitors of the invention and methods of utilizing those compositions in the treatment and prevention of various disorders.

BACKGROUND OF THE INVENTION

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are activated by a variety of signals including growth factors, cytokines, UV radiation, and stress-inducing agents. MAPKs are serine/threonine kinases and their activation occur by dual phosphorylation of threonine and tyrosine at the Thr-X-Tyr segment in the activation loop. MAPKs phosphorylate various substrates including transcription factors, which in turn regulate the expression of specific sets of genes and thus mediate a specific response to the stimulus.

One particularly interesting kinase family are the c-Jun $NH_2$-terminal protein kinases, also known as JNKs. Three distinct genes, JNK1, JNK2, JNK3 have been identified and at least ten different splicing isoforms of JNKs exist in mammalian cells [Gupta et al., EMBO J., 15:2760-70 (1996)]. Members of the JNK family are activated by proinflammatory cytokines, such as tumor necrosis factor-α (TNFα) and interleukin-1β (IL-1β), as well as by environmental stress, including anisomycin, UV irradiation, hypoxia, and osmotic shock [Minden et al., Biochemica et Biophysica Acta, 1333:F85-F104 (1997)].

The down-stream substrates of JNKs include transcription factors c-Jun, ATF-2, Elk1, p53 and a cell death domain protein (DENN) [Zhang et al. Proc. Natl. Acad. Sci. USA, 95:2586-91 (1998)]. Each JNK isoform binds to these substrates with different affinities, suggesting a regulation of signaling pathways by substrate specificity of different JNKs in vivo (Gupta et al., supra).

JNKs, along with other MAPKs, have been implicated in having a role in mediating cellular-response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases.

Several reports have detailed the importance of JNK activation associated with liver disease or episodes of hepatic ischemia [Nat. Genet. 21:326-9 (1999); FEBS Lett. 420:201-4 (1997); J. Clin. Invest. 102:1942-50 (1998); Hepatology 28:1022-30 (1998)]. Therefore, inhibitors of JNK may be useful to treat various hepatic disorders.

A role for JNK in cardiovascular disease such as myocardial infarction or congestive heart failure has also been reported as it has been shown JNK mediates hypertrophic responses to various forms of cardiac stress [Circ. Res. 83:167-78 (1998); Circulation 97:1731-7 (1998); J. Biol. Chem. 272:28050-6 (1997); Circ. Res. 79:162-73 (1996); Circ. Res. 78:947-53 (1996); J. Clin. Invest. 97:508-14 (1996)].

It has been demonstrated that the JNK cascade also plays a role in T-cell activation, including activation of the IL-2 promoter. Thus, inhibitors of JNK may have therapeutic value in altering pathologic immune responses [J. Immunol. 162:3176-87 (1999); Eur. J. Immunol. 28:3867-77 (1998); J. Exp. Med. 186:941-53 (1997); Eur. J. Immunol. 26:989-94 (1996)].

A role for JNK activation in various cancers has also been established, suggesting the potential use of JNK inhibitors in cancer. For example, constitutively activated JNK is associated with HTLV-1 mediated tumorigenesis [Oncogene 13:135-42 (1996)]. JNK may play a role in Kaposi's sarcoma (KS) because it is thought that the proliferative effects of bFGF and OSM on KS cells are mediated by their activation of the JNK signaling pathway [J. Clin. Invest. 99:1798-804 (1997)]. Other proliferative effects of other cytokines implicated in KS proliferation, such as vascular endothelial growth factor (VEGF), IL-6 and TNFα, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) [Blood 92-2450-60 (1998)].

JNK1 and JNK2 are widely expressed in a variety of tissues. In contrast, JNK3, is selectively expressed in the brain and to a lesser extent in the heart and testis [Gupta et al., supra; Mohit et al., Neuron 14:67-78 (1995); Martin et al., Brain Res. Mol. Brain. Res. 35:47-57 (1996)]. JNK3 has been linked to neuronal apoptosis induced by kainic acid, indicating a role of JNK in the pathogenesis of glutamate neurotoxicity. In the adult human brain, JNK3 expression is localized to a subpopulation of pyramidal neurons in the CA1, CA4 and subiculum regions of the hippocampus and layers 3 and 5 of the neocortex [Mohit et al., supra]. The CA1 neurons of patients with acute hypoxia showed strong nuclear JNK3-immunoreactivity compared to minimal, diffuse cytoplasmic staining of the hippocampal neurons from brain tissues of normal patients [Zhang et al., supra]. Thus, JNK3 appears to be involved involved in hypoxic and ischemic damage of CA1 neurons in the hippocampus.

In addition, JNK3 co-localizes immunochemically with neurons vulnerable in Alzheimer's disease [Mohit et al., supra]. Disruption of the JNK3 gene caused resistance of mice to the excitotoxic glutamate receptor agonist kainic acid, including the effects on seizure activity, AP-1 transcriptional activity and apoptosis of hippocampal neurons, indicating that the JNK3 signaling pathway is a critical component in the pathogenesis of glutamate neurotoxicity (Yang et al., Nature, 389:865-870 (1997)].

Based on these findings, JNK signalling, especially that of JNK3, has been implicated in the areas of apoptosis-driven neurodegenerative diseases such as Alzheimer's Disease, Parkinson's Disease, ALS (Amyotrophic Lateral Sclerosis), epilepsy and seizures, Huntington's Disease, traumatic brain injuries, as well as ischemic and hemorrhaging stroke.

There is a high unmet medical need to develop JNK specific inhibitors that are useful in treating the various conditions associated with JNK activation, especially considering the currently available, relatively inadequate treatment options for the majority of these conditions.

Recently, we have described crystallizable complexes of JNK protein and adenosine monophosphate, including complexes comprising JNK3, in U.S. Provisional Application 60/084,056, filed May 4, 1998. Such information has been extremely useful in identifying and designing potential inhibitors of various members of the JNK family, which, in turn, have the described above therapeutic utility.

International PCT publication WO 96/16046 discloses substituted 5-benzyl-2,4-diaminopyrimidines which can be used in the control or prevention of infectious diseases. European Patent Application 0 685 463 A1 describes indolin-2-one derivatives which are efficacious for the treatment and prevention of peptic ulcer, gastritis, reflex esophagitis and Zollinger-Ellison syndrome, and for the treatment of neoplasm originating in the gastrointestinal system. *Khim.-Farm. Zh.* 17, pp. 153-8 (1983) describes the synthesis and antiviral activity of several indole derivatives. *Zh. Vses. Kim. O-va.* 23, pp. 711-12 (1978) relates to the synthesis of substituted indolothiazoles and thienothiazoles. *J. Het. Chem.* 13, pp. 135-137 (1976) describes the synthesis of a variety of 7-substituted pyrrolo[2,3-d]-pyrimidin-6-ones. *Cryst. Struct. Commun.* 2, pp. 613-617 (1973) and Cir. Farm. 32, pp. 613-22 (1974) relate to the crystal structure of N-ethanol-β-isatoxime. *Yakugaku Zasshi* 91, pp. 1323-34 (1971) describes the syntheses and pharmalogical activity of various 3-substituted 1-benzylinolin-2-ones. *Inform. Quim. Anal.* 23, pp. 161-8 (1969) discloses the preparation of N-substituted m-methyl-β-isatoxime derivatives and their reactivity with metallic ions. *Sb. Vys. Sk. Chem.-technol. Praze, Anal. Chem.* 3, pp. 85-112 (1968) relates to the reactions of isatin oximes and their derivatives with metal ions. International PCT publication WO 94/18194 discloses oxindole 1-[N-(alkoxycarbonyl)]carboxamides and 1-(N-carboamido)carboxamides as antiflammatory and analgesic agents.

Much work has been done to identify and develop drugs that inhibit MAPKs, such as p38 inhibitors. See, e.g., WO 98/27098 and WO 95/31451. However, to our knowledge, no MAPK inhibitors have been shown to be specifically selective for JNKs versus other related MAPKs.

Accordingly, there is still a great need to develop potent inhibitors of JNKs, including JNK3 inhibitors, that are useful in treating various conditions associated with JNK activation.

SUMMARY OF THE INVENTION

The present invention addresses this problem by providing compounds that demonstrate strong inhibition of JNK.

These compounds have the general formulae:

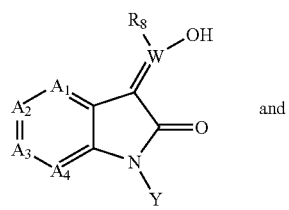

and

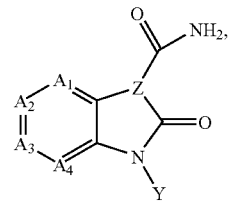

or pharmaceutically acceptable derivatives or prodrugs thereof.

Y is selected from —$(CH_2)$-$Q_1$; —(CO)-$Q_1$; —(CO)NH-$Q_1$; —(CO)—O-$Q_1$; —$(SO_2)$-$Q_1$ or —$(SO_2)$NH-$Q_1$.

$Q_1$ is a $C_1$-$C_6$ straight chain or branched alkyl or alkenyl group; a 5-7 membered aromatic or non-aromatic carbocyclic or heterocyclic ring; or a 9-14 membered bicyclic or tricyclic aromatic or non-aromatic carbocyclic or heterocyclic ring system, wherein said alkyl, alkenyl, ring or ring system is optionally substituted with one to four substituents, each of which is independently selected from $NH_2$, NH—R, $N(R)_2$, $NO_2$, OH, OR, $CF_3$, halo, CN, $CO_2H$, C(O)—$NH_2$, C(O)—NH—R, C(O)—$N(R)_2$, C(O)—R, SR, S(O)—R, $S(O)_2$—R, $S(O)_2$—NH—R or —R.

A heterocyclic ring system or a heterocyclic ring as defined herein is one that contains 1 to 4 heteroatoms, which are independently selected from N, O, S, SO and $SO_2$.

W is N or C. When W is N, $R_8$ is a lone pair of electrons. When W is C, $R_8$ is $R_7$.

$A_1$ is N or $CR^1$;
$A_2$ is N or $CR^2$;
$A_3$ is N or $CR^3$;
$A_4$ is N or $CR^4$;

provided that at least one of $A_1$, $A_2$, $A_3$ and $A_4$ must not be N.

$R^1$ is —$NHR^5$, —$OR^5$, —$SR^5$, or —$R^5$.

$R^2$, $R^3$, and $R^4$ are independently selected from —(CO)$NH_2$, —(CO)NHR, —(CO)$N(R)_2$, —$NHR^5$, —$NHCH_2R^5$, —$OR^5$, —$SR^5$, —$R^5$, —NH(CO)—$R^6$, —NH(CO)—$NHR^6$, —NH(CO)—NH(CO)$R^6$, —NH(CO)—$OR^6$, —NH($SO_2$)—$R^6$, —NH($SO_2$)—$NHR^6$, —C(O)OH, —C(O)OR, —(CO)-$Q_1$, —(CO)NH-$Q_1$, —(CO)NR-$Q_1$, —(CO)—O-$Q_1$, —$(SO_2)$-$Q_1$ or —$(SO_2)$NH-$Q_1$.

$R^5$ and $R^6$ are each independently selected from H; $N(R)_2$, NHOH, $NO_2$, C(O)OR or halo; a $C_1$-$C_6$ straight chain or branched alkyl, alkenyl or alkynyl group; a 5-7 membered aromatic or non-aromatic carbocyclic or heterocyclic ring; or a 9-14 membered bicyclic or tricyclic-aromatic or non-aromatic carbocyclic or heterocyclic ring, wherein said alkyl, alkenyl, ring or ring system is optionally substituted with one to four substituents, each of which is independently selected from $NH_2$, NHR, NHCC(O)OR, $N(R)_2$, $NO_2$, OH, OR, $CF_3$, halo, CN, $Si(R)_3$, $CO_2H$, COOR, $CONH_2$, CONHR, $CON(R)_2$, COR, SR, S(O)R, $S(O)_2R$, $S(O)_2NHR$ or R.

$R^7$ is H; a $C_1$-$C_6$ straight chain or branched alkyl or alkenyl group; a 5-7 membered aromatic or non-aromatic carbocyclic or heterocyclic ring; or a 9-14 membered bicyclic or tricyclic aromatic or non-aromatic carbocyclic or heterocyclic ring; wherein said alkyl, alkenyl, ring or ring system is optionally substituted with one to four substituents, each of which is independently selected from $NH_2$, NHR, $N(R)_2$, $NO_2$, OH, OR, $CF_3$, halo, CN, $CO_2H$, $CONH_2$, CONHR, $CON(R)_2$, COR, SR, S(O)R, $S(O)_2R$, $S(O)_2NHR$ or R.

R is a $C_1$-$C_6$ straight chain or branched alkyl or alkenyl group, a 5-7 membered aromatic or non-aromatic carbocyclic or heterocyclic ring, or a 9-10 membered bicyclic aromatic or non-aromatic carbocyclic or heterocyclic ring system.

Z is CH or N.

In another embodiment, the invention provides pharmaceutical compositions comprising the JNK inhibitors of this invention. These compositions may be utilized in methods for treating or preventing a variety of disorders, such as heart disease, immunodeficiency disorders, inflammatory diseases, allergic diseases, autoimmune diseases, destructive bone disorders such as osteoporosis, proliferative disorders, infectious diseases and viral diseases. These compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), rheumatoid arthritis, asthma, osteoarthritis, ischemia, cancer, liver disease including hepatic ischemia, heart disease such as myocardial infarction and congestive heart failure, pathologic immune conditions involving T cell activation and neurodegenerative disorders. Each of these above-described methods is also part of the present invention.

DETAILED DESCRIPTION OF THE INVENTION

These compounds have the general formulae:

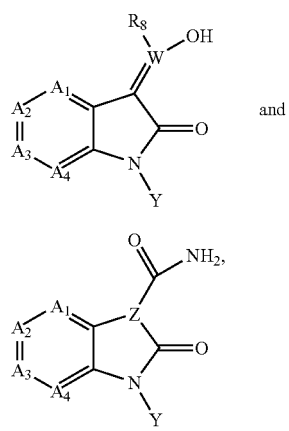

and

I

II or pharmaceutically acceptable derivatives or prodrugs thereof.

Y is selected from —($CH_2$)-$Q_1$; —(CO)-$Q_1$; —(CO)NH-$Q_1$; —(CO)—O-$Q_1$; —($SO_2$)-$Q_1$ or —($SO_2$)NH-$Q_1$.

$Q_1$ is a $C_1$-$C_6$ straight chain or branched alkyl or alkenyl group; a 5-7 membered aromatic or non-aromatic carbocyclic or heterocyclic ring; or a 9-14 membered bicyclic or tricyclic aromatic or non-aromatic carbocyclic or heterocyclic ring system, wherein said alkyl, alkenyl, ring or ring system is optionally substituted with one to four substituents, each of which is independently selected from $NH_2$, NH—R, N(R)$_2$, $NO_2$, OH, OR, $CF_3$, halo, CN, $CO_2$H, C(O)—$NH_2$, C(O)—NH—R, C(O)—N(R)$_2$, C(O)—R, SR, S(O)—R, S(O)$_2$—R, S(O)$_2$—NH—R or —R.

A heterocyclic ring system or a heterocyclic ring as defined herein is one that contains 1 to 4 heteroatoms, which are independently selected from N, O, S, SO and $SO_2$.

W is N or C. When W is N, $R_8$ is a lone pair of electrons. When W is C, $R_8$ is $R_7$.

$A_1$ is N or $CR^1$;
$A_2$ is N or $CR^2$;
$A_3$ is N or $CR^3$;
$A_4$ is N or $CR^4$;
provided that at least one of $A_1$, $A_2$, $A_3$ and $A_4$ must not be N.

$R^1$ is —$NHR^5$, —$OR^5$, —$SR^5$, or —$R^5$.

$R^2$, $R^3$, and $R^4$ are independently selected from —(CO)$NH_2$, —(CO)NHR, —(CO)N(R)$_2$, —$NHR^5$, —$NHCH_2R^5$, —$OR^5$, —$SR^5$, —$R^5$, —NH(CO)—$R^6$, —NH(CO)—$NHR^6$, —NH(CO)—NH(CO)$R^6$, —NH(CO)—$OR^6$, —NH($SO_2$)—$R^6$, —NH($SO_2$)—$NHR^6$, —C(O)OH, —C(O)OR, —(CO)-$Q_1$, —(CO)NH-$Q_1$, —(CO)NR-$Q_1$, —(CO)—O-$Q_1$, —($SO_2$)-$Q_1$ or —($SO_2$)NH-$Q_1$.

$R^5$ and $R^6$ are each independently selected from H; N(R)$_2$, NHOH, $NO_2$, C(O)OR or halo; a $C_1$-$C_6$ straight chain or branched alkyl, alkenyl or alkynyl group; a 5-7 membered aromatic or non-aromatic carbocyclic or heterocyclic ring; or a 9-14 membered bicyclic or tricyclic aromatic or non-aromatic carbocyclic or heterocyclic ring optionally substituted with one to four substituents, wherein said alkyl, alkenyl, ring or ring system is optionally substituted with one to four substituents, each of which is independently selected from $NH_2$, NHR, NHC(O)OR, N(R)$_2$, $NO_2$, OH, OR, $CF_3$, halo, CN, Si(R)$_3$, $CO_2$H, COOR, $CONH_2$, CONHR, CON(R)$_2$, COR, SR, S(O)R, S(O)$_2$R, S(O)$_2$NHR or R.

$R^7$ is H; a $C_1$-$C_6$ straight chain or branched alkyl or alkenyl group, optionally substituted with one to four substituents, each of which is independently selected from $NH_2$, NHR, N(R)$_2$, $NO_2$; OH, OR, $CF_3$, halo, CN, $CO_2$H, $CONH_2$, CONHR, CON(R)$_2$, COR, SR, S(O)R, S(O)$_2$R, S(O)$_2$NHR or R; a 5-7 membered aromatic or non-aromatic carbocyclic or heterocyclic ring, optionally substituted with one to four substituents, each of which is independently selected from $NH_2$, NHR, N(R)$_2$, $NO_2$, OH, OR, $CF_3$, halo, CN, $CO_2$H, $CONH_2$, CONHR, CON(R)$_2$, COR, SR, S(O)R, S(O)$_2$R, S(O)$_2$NHR or R; or a 9-10 membered bicyclic aromatic or non-aromatic carbocyclic or heterocyclic ring optionally substituted with one to four substituents, each of which is independently selected from $NH_2$, NHR, N(R)$_2$, $NO_2$, OH, OR, $CF_3$, halo, CN, $CO_2$H, $CONH_2$, CONHR, CON(R)$_2$, COR, SR, S(O)R, S(O)$_2$R, S(O)$_2$NHR or R.

R is a $C_1$-$C_6$ straight chain or branched alkyl or alkenyl group, a 5-7 membered aromatic or non-aromatic carbocyclic or heterocyclic ring, or a 9-10 membered bicyclic aromatic or non-aromatic carbocyclic or heterocyclic ring system.

Z is CH or N.

When Z is CH, the carbon is chiral. Both isomeric forms of the compound are encompassed by the instant invention. In addition, when Z is CH, the acidic nature of the CH proton can result in tautomeric structures of formula II, as shown below. These tautomeric structures,

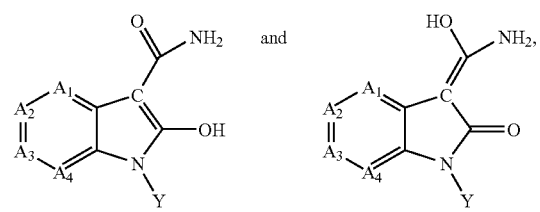

are encompassed by the instant invention.

The present invention envisions all possible stereoisomers, enantiomers and racemic mixtures. For example, oxime compounds may exist in isomeric forms. The oxime compounds of this invention may exist as either an E-isomer, a Z-isomer, or a mixture of E- and Z-isomers.

According to a preferred embodiment, Y is —(CH$_2$)-Q$_1$.

According to a preferred embodiment, Q$_1$ is benzodioxanyl, an optionally substituted phenyl group, a substituted heterocyclic ring, a 10-membered heterocyclic bicyclic ring, or a straight chain alkyl group substituted with phenyl or a heterocyclic monocyclic or bicyclic ring.

According to a preferred embodiment, W is N and R$^8$ is a lone pair of electrons.

According to a preferred embodiment, A$_1$ is CR$^1$.
According to a preferred embodiment, A$_2$ is CR$^2$ or CR$^3$.
According to a preferred embodiment, A$_3$ is CR$^2$ or CR$^3$.
According to a preferred embodiment, A4 is CR$^4$.
According to a preferred embodiment, R$^1$ is R$^5$. In a more preferred embodiment, R$^1$ is H, methyl, halo, an optionally substituted phenyl, a monocyclic or bicyclic heterocycle, a substituted or unsubstituted alkyl, alkenyl or alkynyl, or COOR.

According to a preferred embodiment, R$^2$ is R$^5$, NH(CO)—R$^6$, NH(SO$_2$)—R$^6$, —NHCH$_2$R$^5$, CO-Q$_1$ or CONH-Q$_1$. In a more preferred embodiment, R$^2$ is H, halo, NO$_2$, NH$_2$, methyl, OCF$_3$, —N(R)$_2$, or substituted phenyl.

According to a preferred embodiment, R$^3$ is R$^5$, NH(CO)—R$^6$, NH(SO$_2$)—R$^6$, CONH-Q$_1$, In a more preferred embodiment, R$^3$ is H, halo, methyl, CF$_3$, substituted or unsubstituted phenyl, a heterocyclic ring, a bicyclic ring, NO$_2$ or NH$_2$.

According to a preferred embodiment, R$^4$ is R$^5$. In a more preferred embodiment, R$^4$ is H or methyl.

Some specific examples of preferred compounds of the instant invention are provided in Tables 1 to 17 below. In Tables 1 to 17, "+" represents a Ki$\geq$1 µM, "++" represents a Ki <1 µM, and "ND" means not determined. The Ki is determined by the method disclosed in Example 6.

TABLE 1

| Cmpd | Structure | Ki |
|---|---|---|
| 1 | ![structure] | + |
| 2 | ![structure] | ++ |
| 3 | ![structure] | + |
| 4 | ![structure] | ++ |

TABLE 1-continued
| Cmpd | Structure | Ki |
|---|---|---|
| 5 | 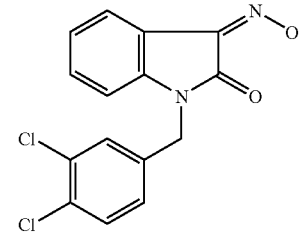 | ++ |
| 6 | 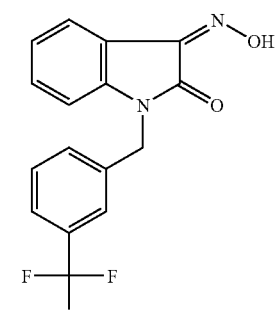 | + |
| 7 | 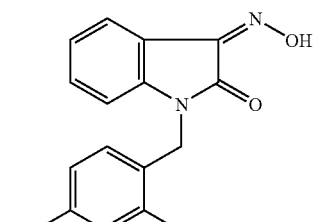 | ++ |
| 8 | 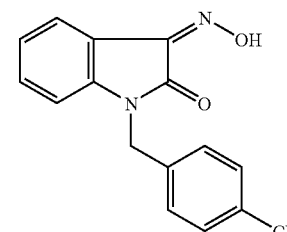 | + |
| 9 | 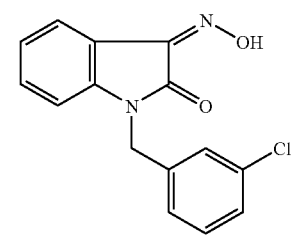 | + |
| 10 | 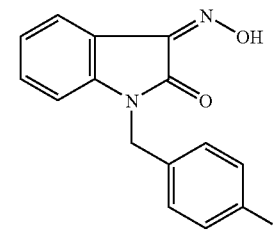 | + |

TABLE 1-continued
| Cmpd | Structure | Ki |
|------|-----------|-----|
| 11 | 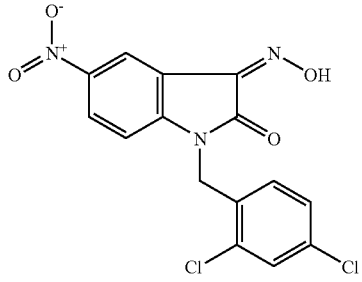 | + |
| 12 | 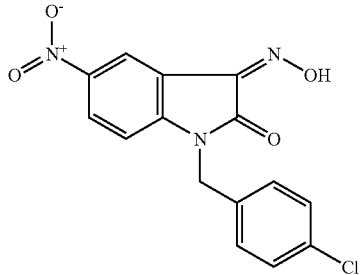 | + |
| 13 | 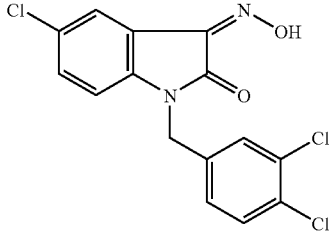 | ++ |
| 14 | 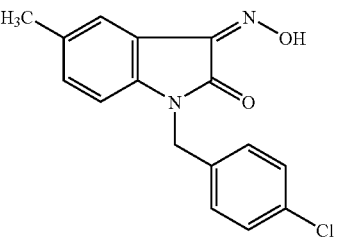 | + |
| 15 | 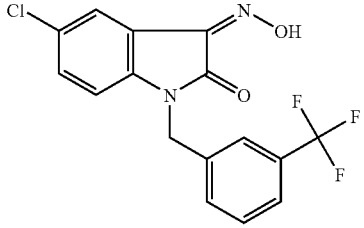 | + |

TABLE 1-continued

| Cmpd | Structure | Ki |
|---|---|---|
| 16 | 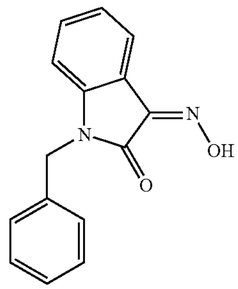 | ND |
| 17 | 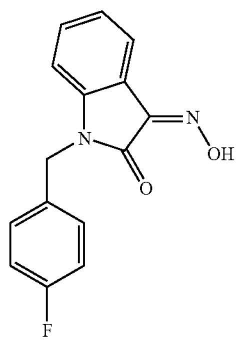 | + |
| 18 | 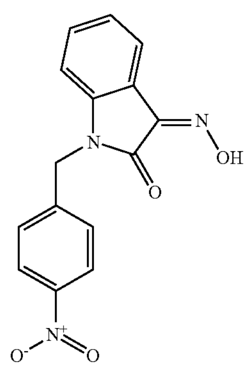 | + |
| 19 | 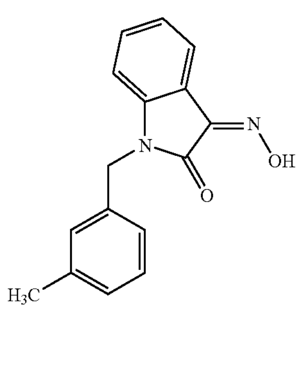 | + |

TABLE 1-continued

| Cmpd | Structure | Ki |
|------|-----------|-----|
| 20 | 1-(3-fluorobenzyl)-3-(hydroxyimino)indolin-2-one | + |
| 21 | 1-(2-fluorobenzyl)-3-(hydroxyimino)indolin-2-one | + |
| 22 | 3-(hydroxyimino)-1-(2-nitrobenzyl)indolin-2-one | ND |
| 23 | 1-benzyl-5-bromo-3-(hydroxyimino)indolin-2-one | + |

TABLE 1-continued

| Cmpd | Structure | Ki |
|------|-----------|-----|
| 24 | 5-bromo-1-(4-fluorobenzyl)-3-(hydroxyimino)indolin-2-one | + |
| 25 | 5-bromo-1-(4-nitrobenzyl)-3-(hydroxyimino)indolin-2-one | + |
| 26 | 5-bromo-1-(4-methylbenzyl)-3-(hydroxyimino)indolin-2-one | + |
| 27 | 5-bromo-1-(3-methylbenzyl)-3-(hydroxyimino)indolin-2-one | + |

TABLE 1-continued

| Cmpd | Structure | Ki |
|------|-----------|-----|
| 28 | 5-bromo-1-(3-fluorobenzyl)-3-(hydroxyimino)indolin-2-one | + |
| 29 | 5-bromo-1-(2-fluorobenzyl)-3-(hydroxyimino)indolin-2-one | + |
| 30 | 5-bromo-3-(hydroxyimino)-1-(2-nitrobenzyl)indolin-2-one | ND |
| 31 | 1-benzyl-3-(hydroxyimino)-5-nitroindolin-2-one | ND |

TABLE 1-continued
| Cmpd | Structure | Ki |
|---|---|---|
| 32 | 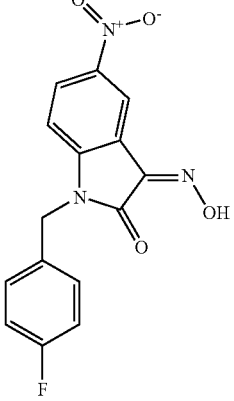 | ND |
| 33 | 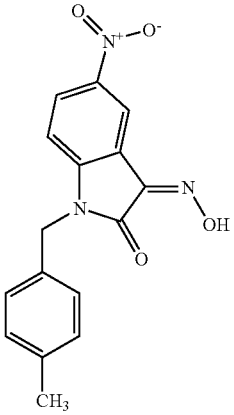 | + |
| 34 | 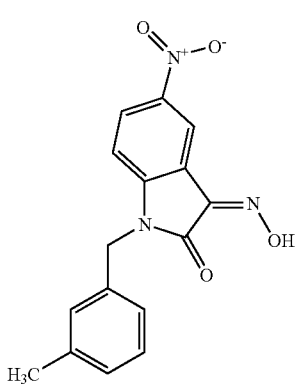 | + |
| 35 | 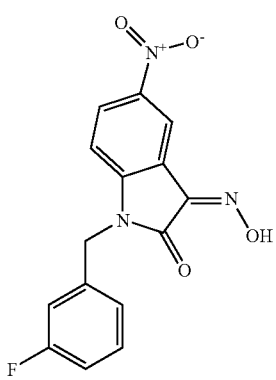 | ND |

TABLE 1-continued

| Cmpd | Structure | Ki |
|------|-----------|----|
| 36 | 5-nitro-1-(2-fluorobenzyl)isatin-3-oxime | ND |
| 37 | 5-methyl-1-benzylisatin-3-oxime | ND |
| 38 | 5-methyl-1-(4-fluorobenzyl)isatin-3-oxime | ND |
| 39 | 5-methyl-1-(4-nitrobenzyl)isatin-3-oxime | + |

TABLE 1-continued
| Cmpd | Structure | Ki |
|---|---|---|
| 40 | 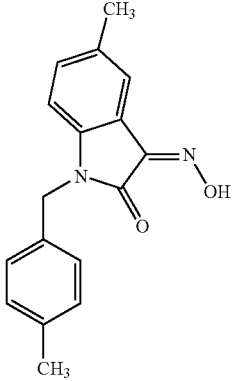 | ND |
| 41 | 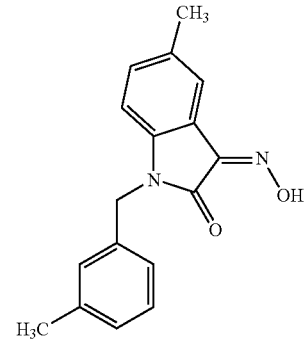 | ND |
| 42 | 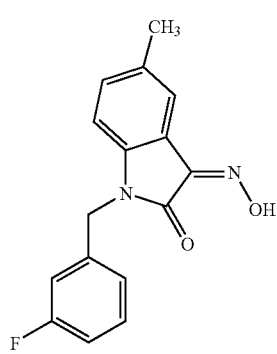 | ND |
| 43 | 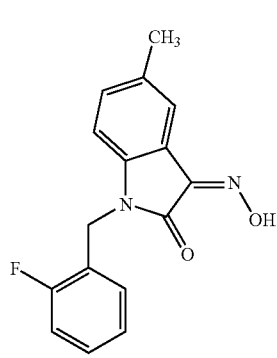 | ND |

TABLE 1-continued

| Cmpd | Structure | Ki |
|------|-----------|----|
| 44 | 5-methyl-1-(2-nitrobenzyl)-3-(hydroxyimino)indolin-2-one | ND |
| 45 | 5-chloro-1-benzyl-3-(hydroxyimino)indolin-2-one | + |
| 46 | 5-chloro-1-(4-fluorobenzyl)-3-(hydroxyimino)indolin-2-one | + |
| 47 | 5-chloro-1-(4-nitrobenzyl)-3-(hydroxyimino)indolin-2-one | + |

TABLE 1-continued

| Cmpd | Structure | Ki |
|---|---|---|
| 48 | 5-chloro-1-(4-methylbenzyl)-3-(hydroxyimino)indolin-2-one | + |
| 49 | 5-chloro-1-(3-methylbenzyl)-3-(hydroxyimino)indolin-2-one | + |
| 50 | 5-chloro-1-(3-fluorobenzyl)-3-(hydroxyimino)indolin-2-one | + |
| 51 | 5-chloro-1-(2-fluorobenzyl)-3-(hydroxyimino)indolin-2-one | + |

TABLE 1-continued

| Cmpd | Structure | Ki |
|------|-----------|-----|
| 52 | 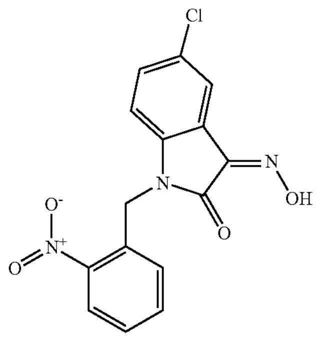 | ND |
| 53 | 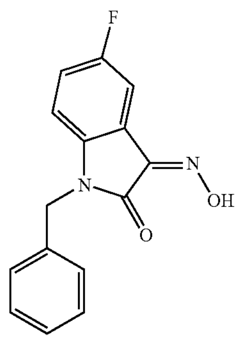 | ND |
| 54 | 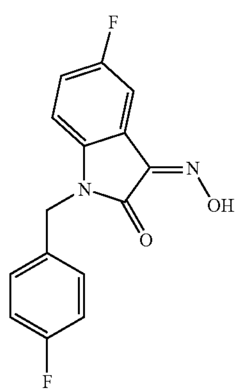 | + |
| 55 | 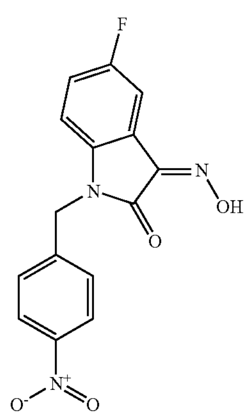 | + |

TABLE 1-continued
| Cmpd | Structure | Ki |
|---|---|---|
| 56 | 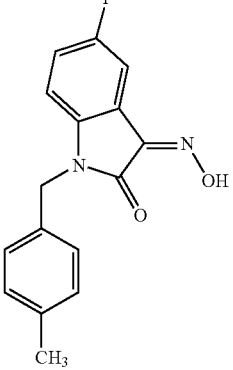 | + |
| 57 | 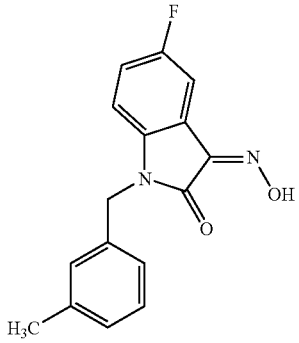 | + |
| 58 | 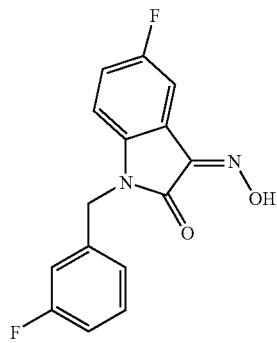 | + |
| 59 | 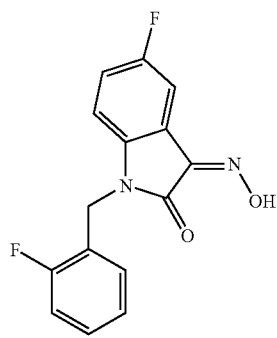 | + |

TABLE 1-continued

| Cmpd | Structure | Ki |
|---|---|---|
| 60 | (5-fluoro-1-(2-nitrobenzyl)-1H-indole-2,3-dione 3-oxime) | ND |
| 61 | (1-(4-methoxybenzyl)-1H-indole-2,3-dione 3-oxime) | + |
| 62 | (1-(3-nitrobenzyl)-1H-indole-2,3-dione 3-oxime) | ++ |
| 63 | (1-(2-cyanobenzyl)-1H-indole-2,3-dione 3-oxime) | + |

TABLE 1-continued
| Cmpd | Structure | Ki |
|---|---|---|
| 64 | 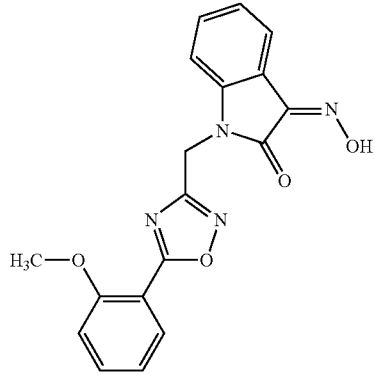 | + |
| 65 | 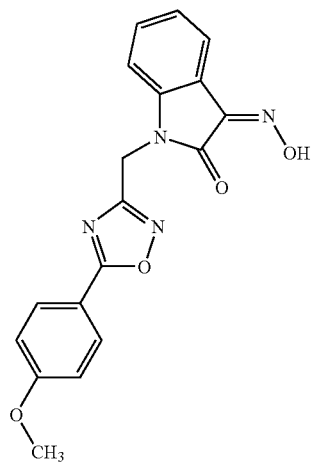 | + |
| 66 | 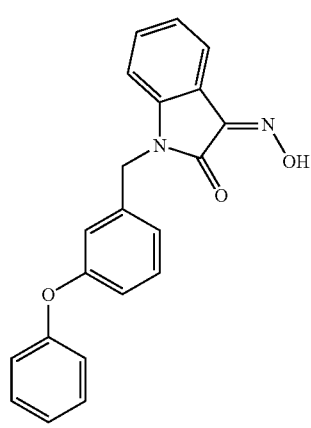 | + |

TABLE 1-continued
| Cmpd | Structure | Ki |
|---|---|---|
| 67 | 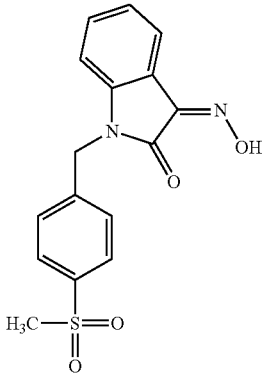 | + |
| 68 | 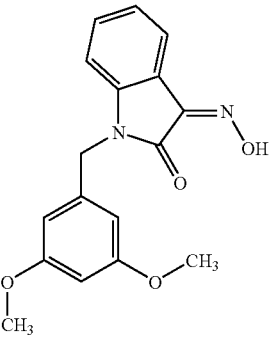 | ++ |
| 69 | 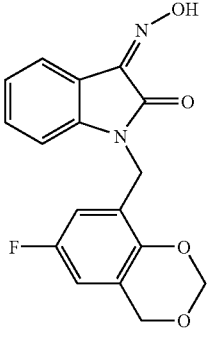 | ++ |
| 70 | 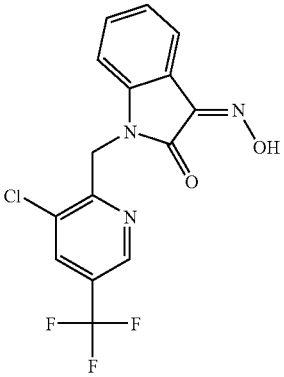 | + |

TABLE 1-continued

| Cmpd | Structure | Ki |
|------|-----------|-----|
| 71 | 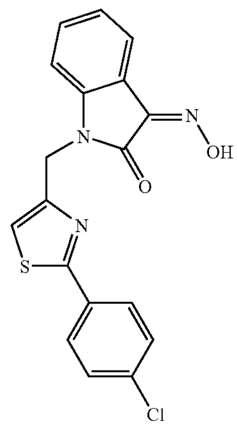 | + |
| 72 | 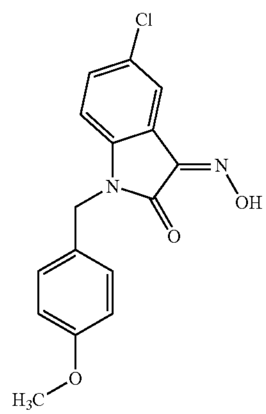 | + |
| 73 | 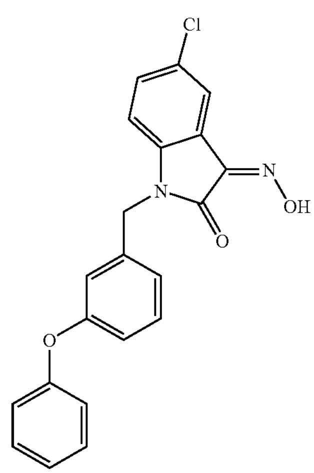 | + |

TABLE 1-continued

| Cmpd | Structure | Ki |
|---|---|---|
| 74 | 5-chloro-1-(3,5-dimethoxybenzyl)-3-(hydroxyimino)indolin-2-one | ++ |
| 75 | 5-chloro-1-((7-fluoro-2,3-dihydrobenzo[b][1,4]dioxin-5-yl)methyl)-3-(hydroxyimino)indolin-2-one | ++ |
| 76 | 5-chloro-3-(hydroxyimino)-1-(pyridin-2-ylmethyl)indolin-2-one | + |
| 77 | 5-chloro-1-((2-(4-chlorophenyl)thiazol-4-yl)methyl)-3-(hydroxyimino)indolin-2-one | ++ |

TABLE 1-continued

| Cmpd | Structure | Ki |
|---|---|---|
| 78 | 5-fluoro-3-(hydroxyimino)-1-(4-methoxybenzyl)indolin-2-one | + |
| 79 | 5-fluoro-3-(hydroxyimino)-1-(3-nitrobenzyl)indolin-2-one | + |
| 80 | 2-((5-fluoro-3-(hydroxyimino)-2-oxoindolin-1-yl)methyl)benzonitrile | + |
| 81 | 5-fluoro-3-(hydroxyimino)-1-((5-(2-methoxyphenyl)-1,2,4-oxadiazol-3-yl)methyl)indolin-2-one | + |

TABLE 1-continued
| Cmpd | Structure | Ki |
|------|-----------|-----|
| 82 | 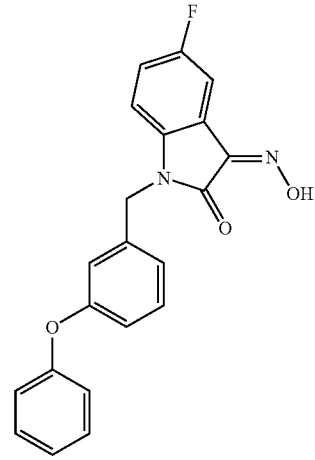 | + |
| 83 | 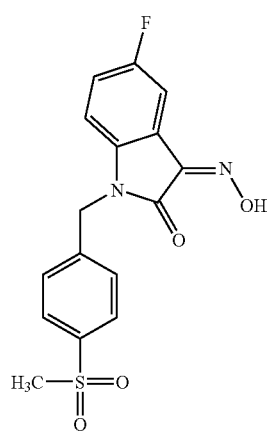 | + |
| 84 | 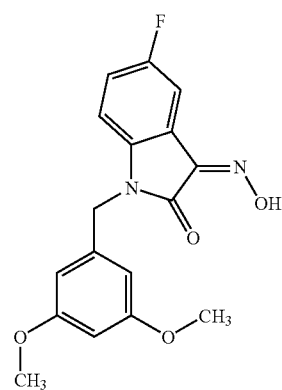 | ++ |

TABLE 1-continued

| Cmpd | Structure | Ki |
|------|-----------|-----|
| 85 | 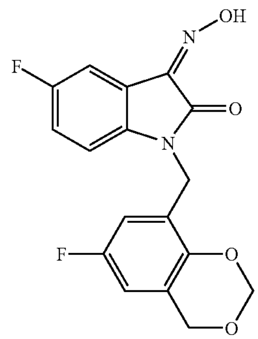 | ++ |
| 86 | 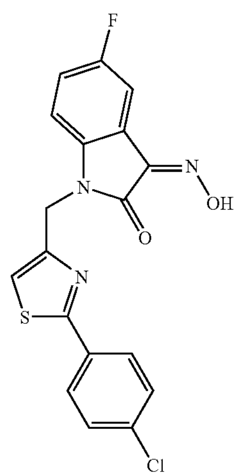 | + |
| 87 | 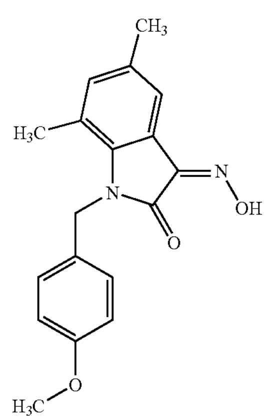 | + |

TABLE 1-continued
| Cmpd | Structure | Ki |
|---|---|---|
| 88 | 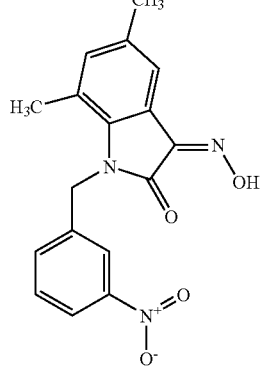 | + |
| 89 | 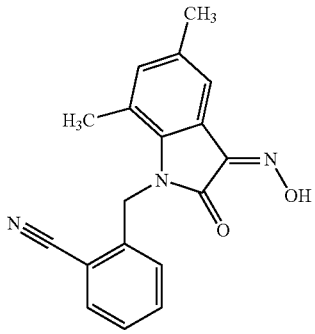 | + |
| 90 | 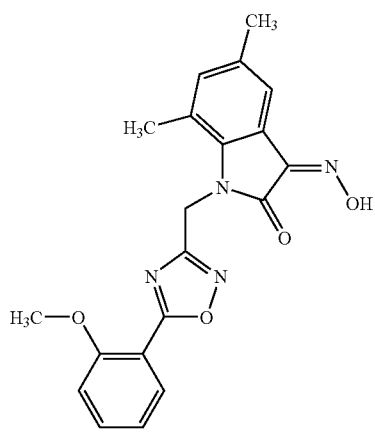 | + |

TABLE 1-continued
| Cmpd | Structure | Ki |
|------|-----------|-----|
| 91 | 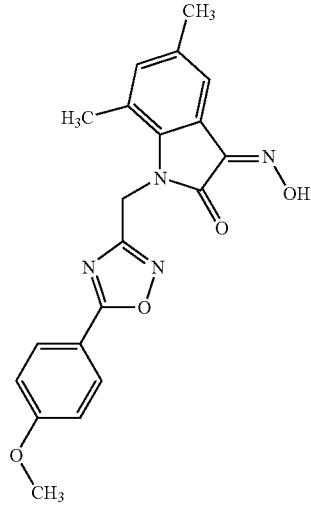 | + |
| 92 | 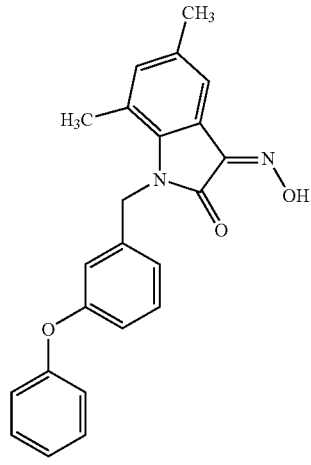 | + |
| 93 | 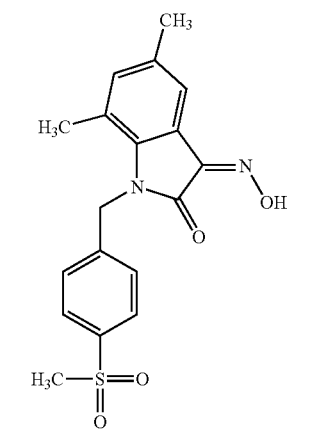 | + |

TABLE 1-continued

| Cmpd | Structure | Ki |
|------|-----------|----|
| 94 | 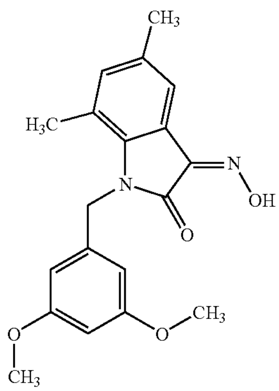 | + |
| 95 | 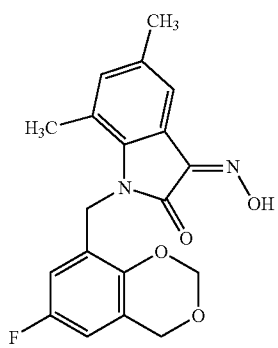 | + |
| 96 | 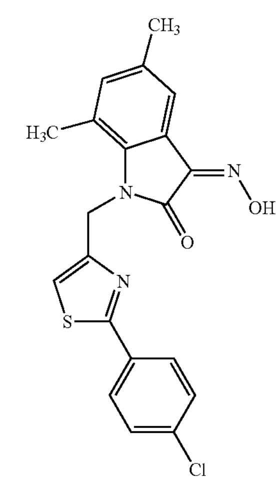 | + |

TABLE 1-continued

| Cmpd | Structure | Ki |
|---|---|---|
| 97 | 5-Cl, 7-CH₃, 1-(4-methoxybenzyl) isatin 3-oxime | + |
| 98 | 5-Cl, 7-CH₃, 1-(3-nitrobenzyl) isatin 3-oxime | ++ |
| 99 | 5-Cl, 7-CH₃, 1-(2-cyanobenzyl) isatin 3-oxime | + |

TABLE 1-continued

| Cmpd | Structure | Ki |
|---|---|---|
| 100 | 5-chloro-7-methyl-1-(3-phenoxybenzyl)-3-(hydroxyimino)indolin-2-one | + |
| 101 | 5-chloro-7-methyl-1-(4-(methylsulfonyl)benzyl)-3-(hydroxyimino)indolin-2-one | + |
| 102 | 5-chloro-1-(3,5-dimethoxybenzyl)-7-methyl-3-(hydroxyimino)indolin-2-one | ++ |

TABLE 1-continued

| Cmpd | Structure | Ki |
|------|-----------|-----|
| 103 | 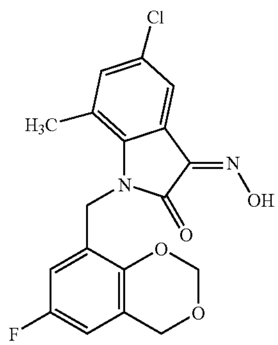 | ++ |
| 104 | 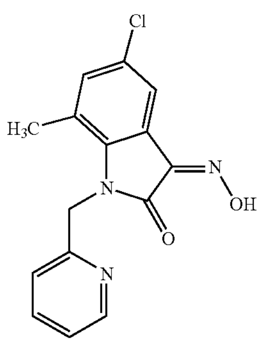 | + |
| 105 | 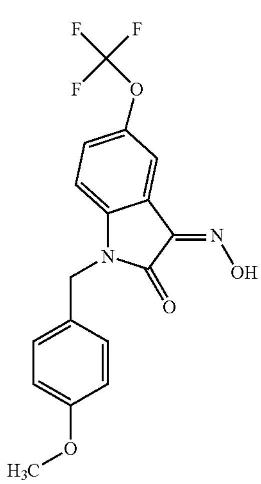 | + |

TABLE 1-continued
| Cmpd | Structure | Ki |
|------|-----------|----|
| 106 | 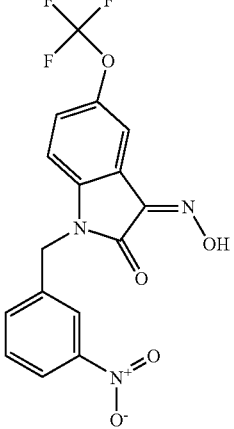 | + |
| 107 | 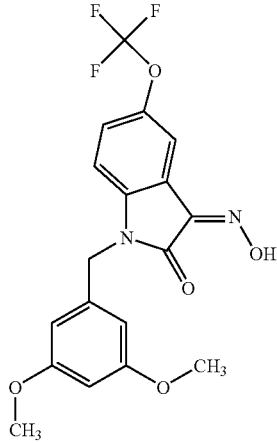 | + |
| 108 | 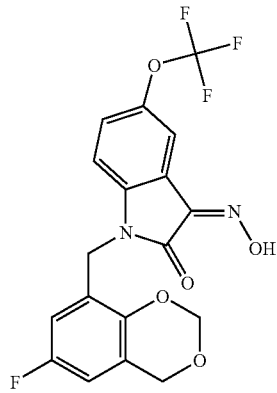 | + |

TABLE 1-continued

| Cmpd | Structure | Ki |
|------|-----------|-----|
| 109 | 5-fluoro-3-(hydroxyimino)-1-{[5-(4-methoxyphenyl)-1,2,4-oxadiazol-3-yl]methyl}-1,3-dihydro-2H-indol-2-one | + |
| 110 | 3-(hydroxyimino)-5,7-dimethyl-1-(pyridin-2-ylmethyl)-1,3-dihydro-2H-indol-2-one | + |
| 111 | 1-(1H-benzimidazol-2-ylmethyl)-5-chloro-3-(hydroxyimino)-7-methyl-1,3-dihydro-2H-indol-2-one | + |
| 112 | 5-chloro-1-{[2-(4-chlorophenyl)-1,3-thiazol-4-yl]methyl}-3-(hydroxyimino)-7-methyl-1,3-dihydro-2H-indol-2-one | ND |

TABLE 1-continued

| Cmpd | Structure | Ki |
|---|---|---|
| 113 | 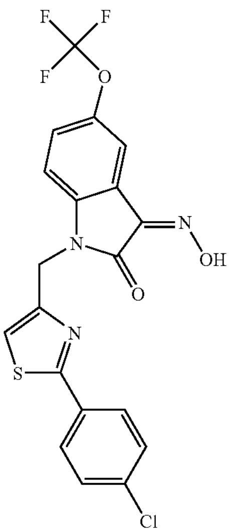 | ND |
| 114 | 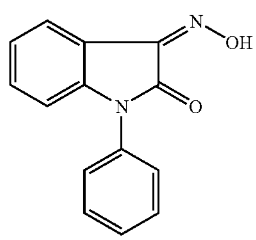 | ND |
| 115 | 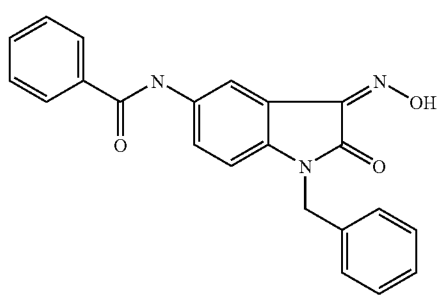 | + |
| 116 | 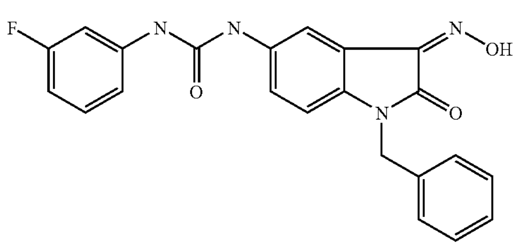 | ND |

TABLE 1-continued

| Cmpd | Structure | Ki |
|------|-----------|----|
| 117 | 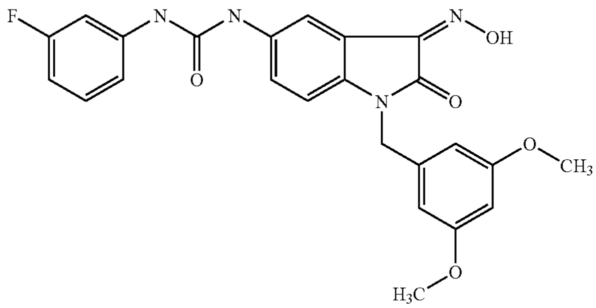 | ND |
| 118 | 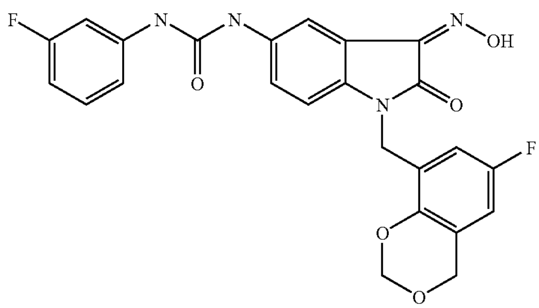 | ND |
| 119 | 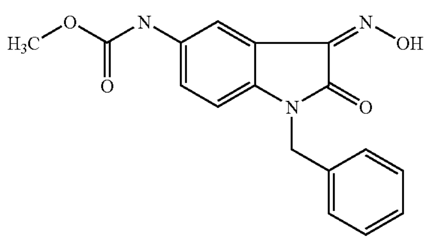 | ND |
| 120 | 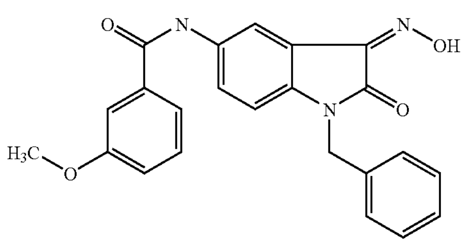 | + |
| 121 | 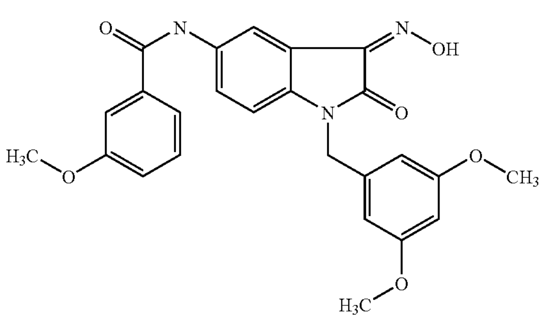 | + |

TABLE 1-continued

| Cmpd | Structure | Ki |
|------|-----------|-----|
| 122 | 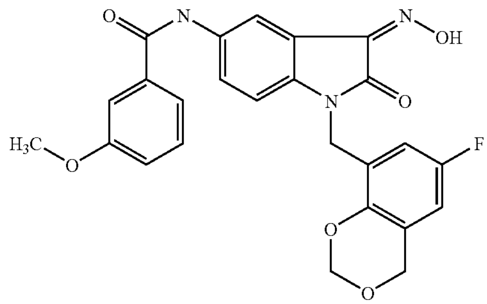 | + |
| 123 | 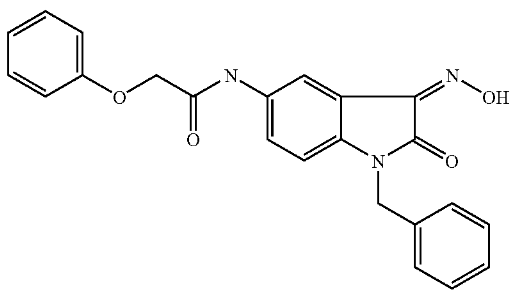 | ND |
| 124 | 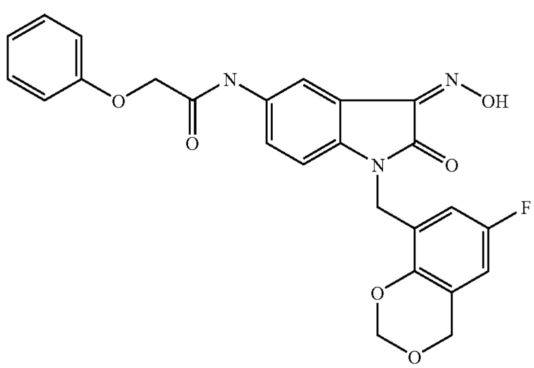 | ND |
| 125 | 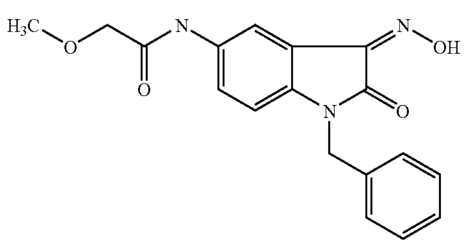 | ND |
| 126 | 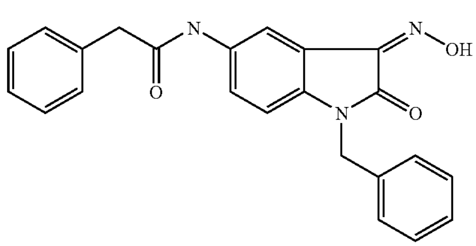 | ND |

TABLE 1-continued

| Cmpd | Structure | Ki |
|------|-----------|-----|
| 127 | 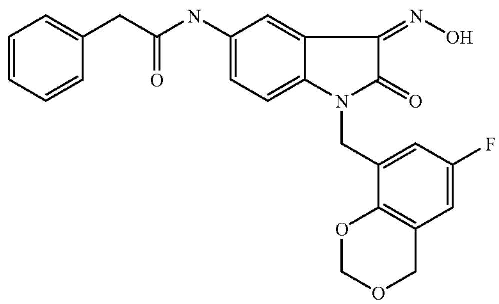 | ND |
| 128 | 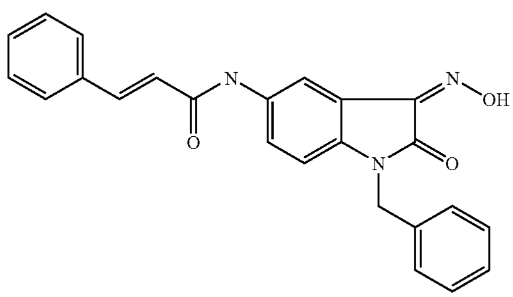 | ND |
| 129 | 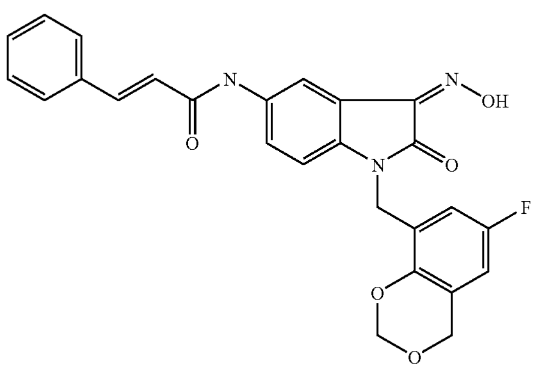 | ND |
| 130 | 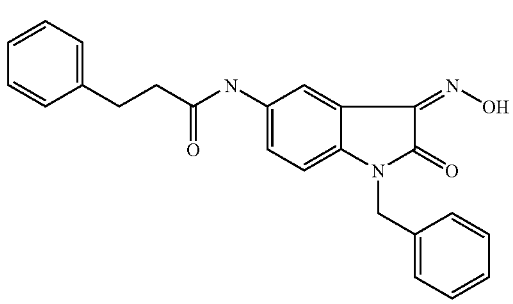 | ND |

TABLE 1-continued

| Cmpd | Structure | Ki |
|------|-----------|-----|
| 131 | 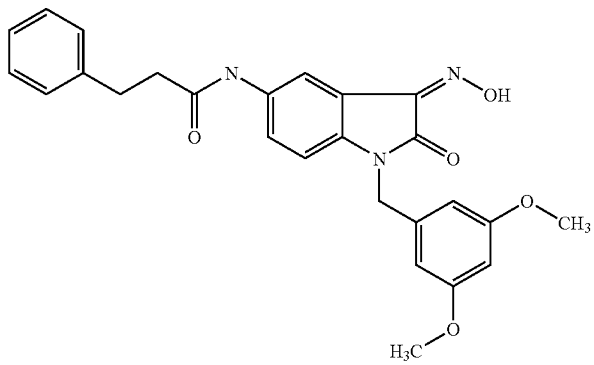 | + |
| 132 | 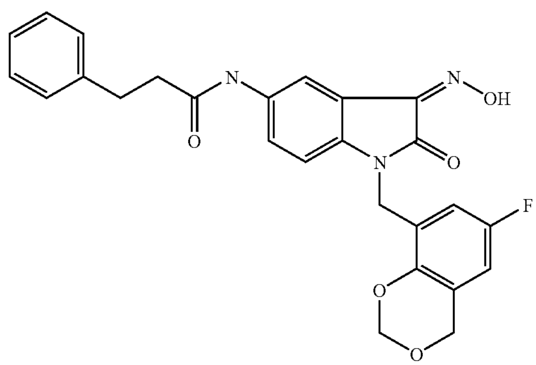 | ND |
| 133 | 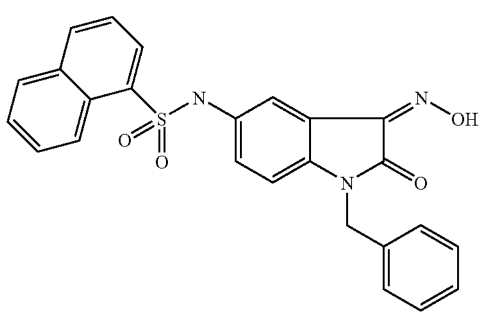 | ND |
| 134 | 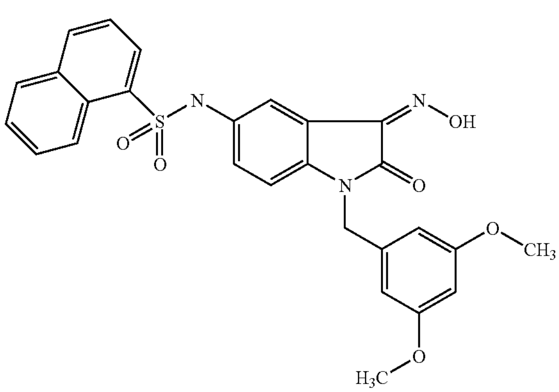 | ND |

TABLE 1-continued
| Cmpd | Structure | Ki |
|---|---|---|
| 135 | 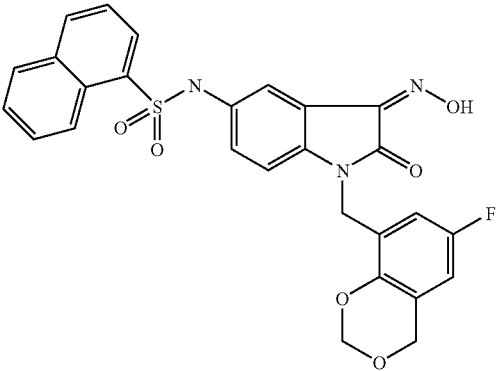 | ND |
| 136 | 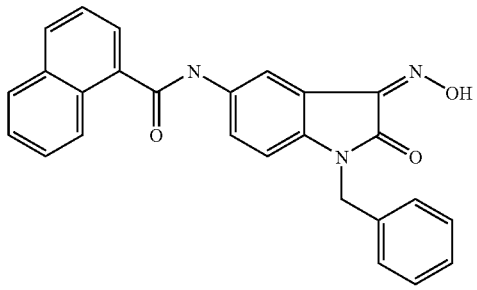 | + |
| 137 | 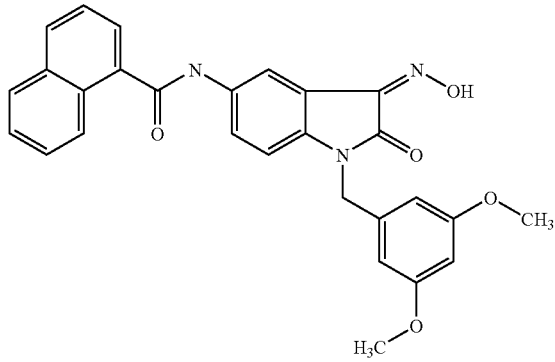 | ND |
| 138 | 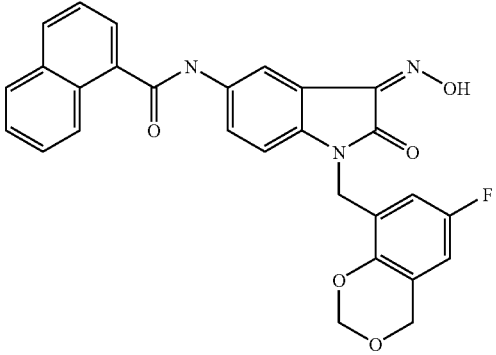 | ND |

TABLE 1-continued

| Cmpd | Structure | Ki |
|---|---|---|
| 139 | 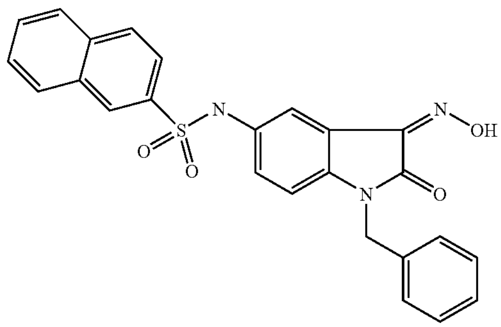 | ND |
| 140 | 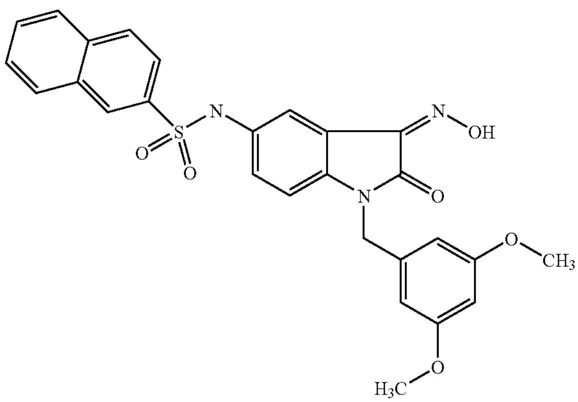 | ND |
| 141 | 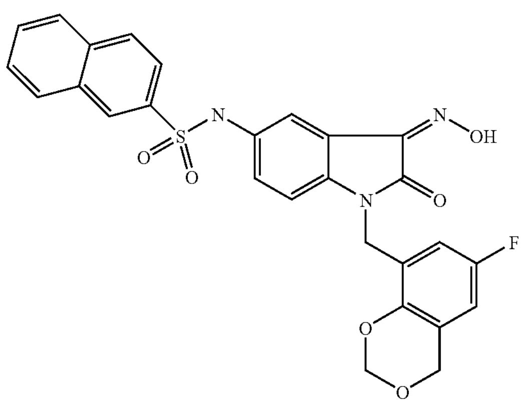 | ND |
| 142 | 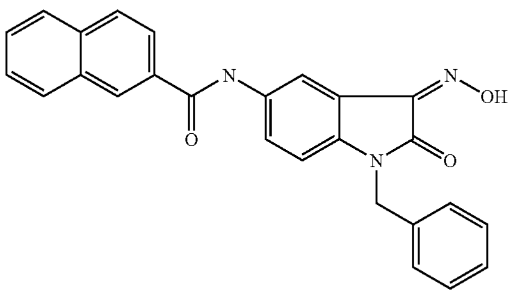 | ND |

TABLE 1-continued

| Cmpd | Structure | Ki |
|------|-----------|-----|
| 143 | 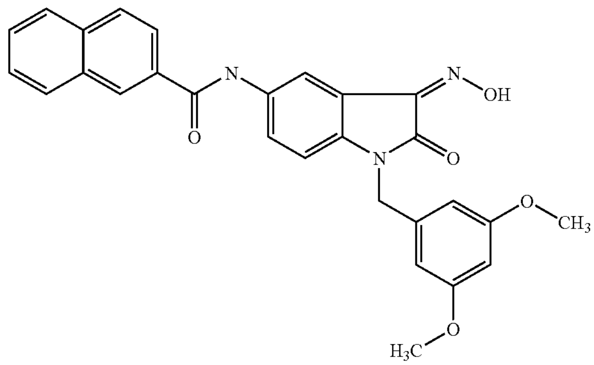 | ND |
| 144 | 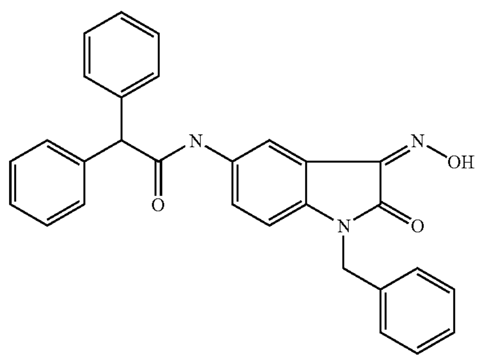 | ND |
| 145 | 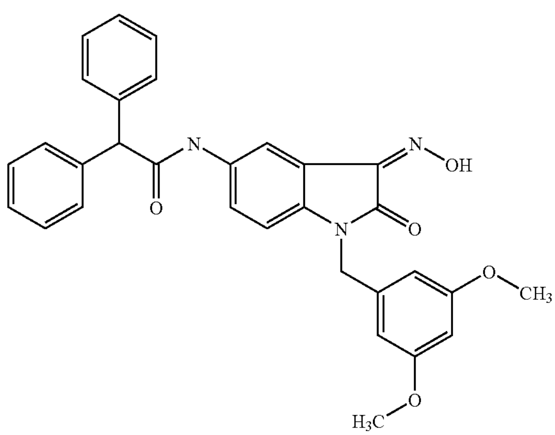 | ND |
| 146 | 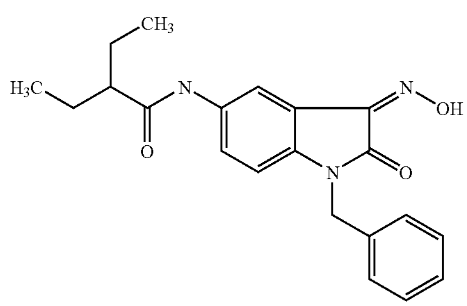 | ND |

TABLE 1-continued

| Cmpd | Structure | Ki |
|------|-----------|-----|
| 147 | 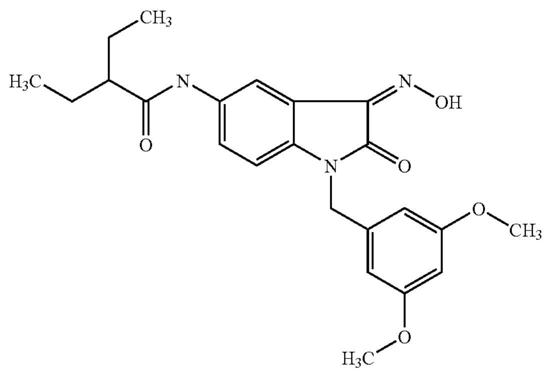 | ND |
| 148 | 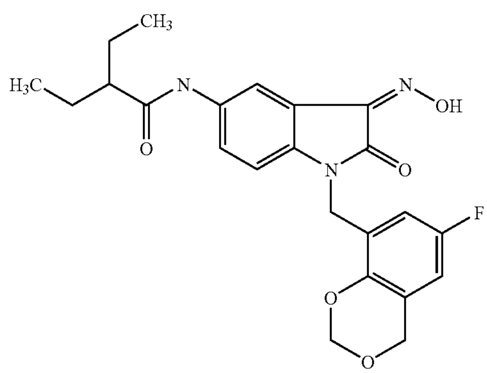 | ND |
| 149 | 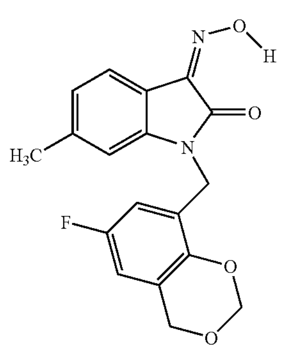 | ++ |
| 150 | 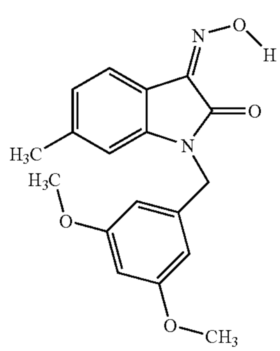 | ++ |

TABLE 1-continued
| Cmpd | Structure | Ki |
|---|---|---|
| 151 | 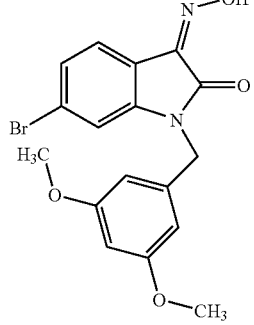 | ++ |
| 152 | 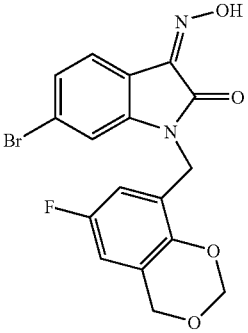 | ++ |
| 153 | 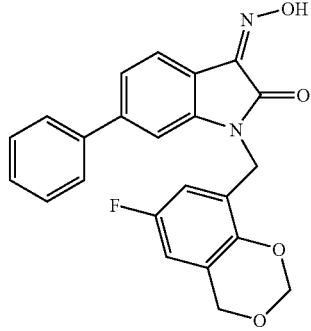 | ++ |
| 154 | 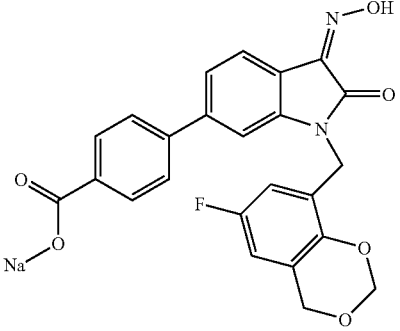 | ++ |

TABLE 1-continued

| Cmpd | Structure | Ki |
|------|-----------|-----|
| 155 | 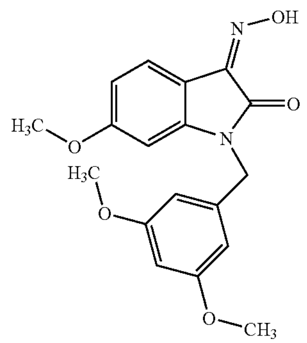 | ++ |
| 156 | 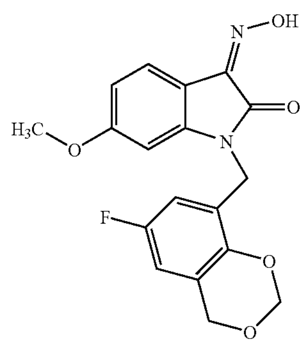 | ++ |
| 157 | 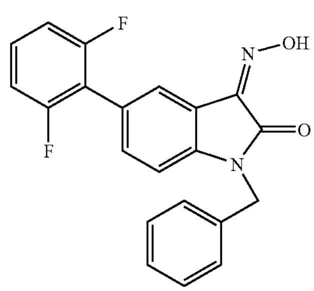 | + |
| 158 | 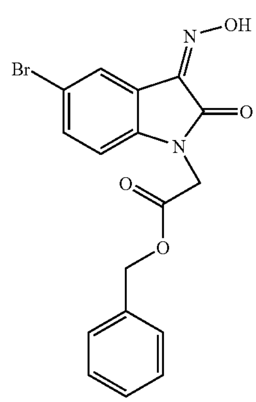 | + |

TABLE 1-continued

| Cmpd | Structure | Ki |
|------|-----------|-----|
| 159 | 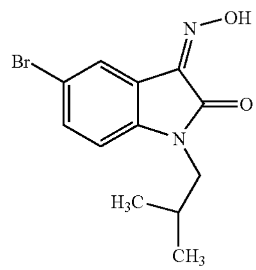 | + |
| 160 | 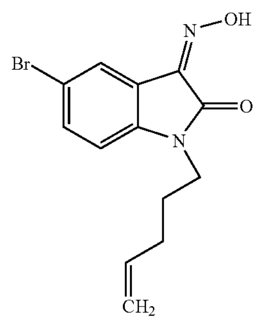 | + |
| 161 | 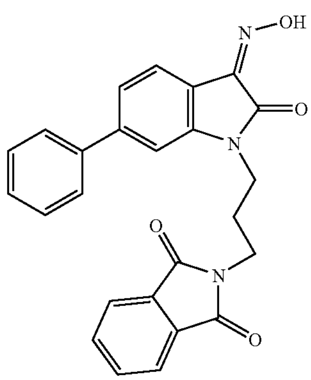 | + |
| 162 | 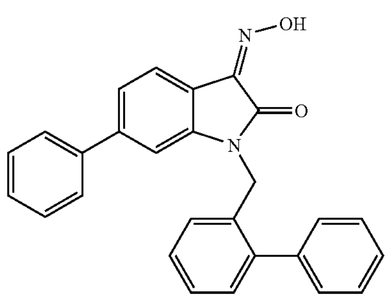 | + |
| 163 | 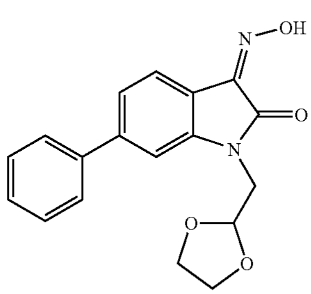 | + |

TABLE 1-continued

| Cmpd | Structure | Ki |
|------|-----------|-----|
| 164 | 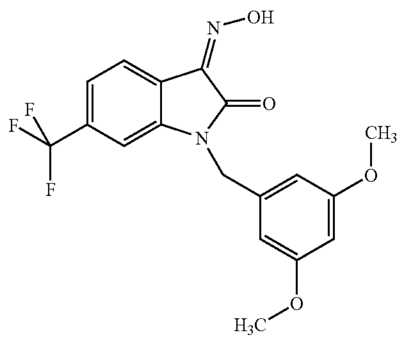 | ++ |
| 165 | 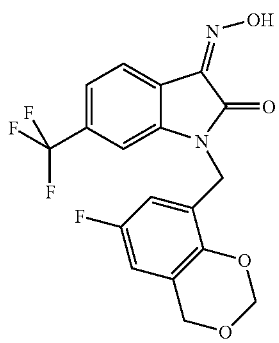 | ++ |
| 166 | 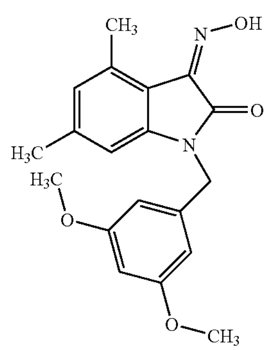 | ++ |
| 167 | 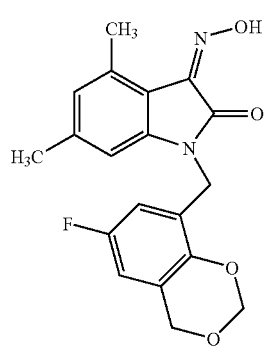 | ++ |

TABLE 1-continued

| Cmpd | Structure | Ki |
|------|-----------|-----|
| 168 | 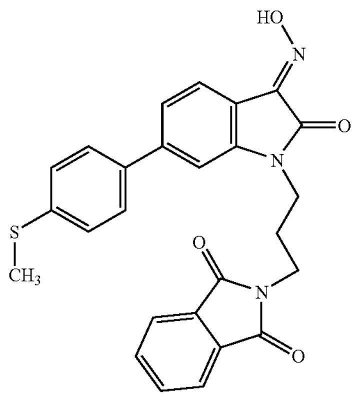 | ND |
| 169 | 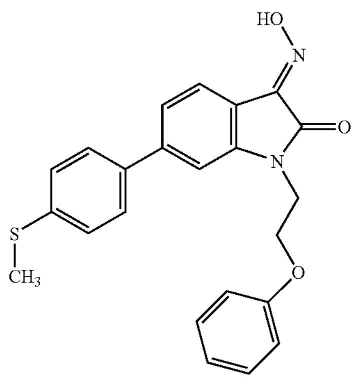 | ND |
| 170 | 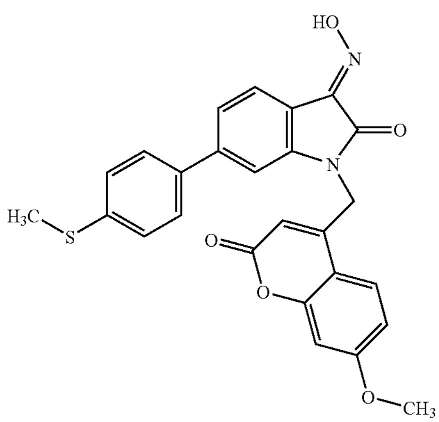 | ND |
| 171 | 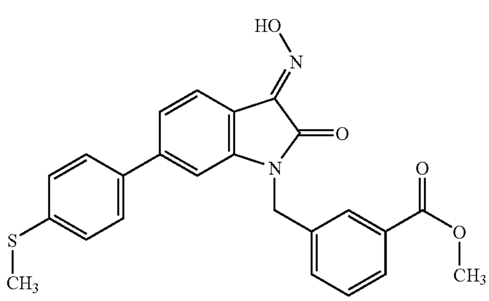 | ND |

TABLE 1-continued

| Cmpd | Structure | Ki |
|---|---|---|
| 172 | 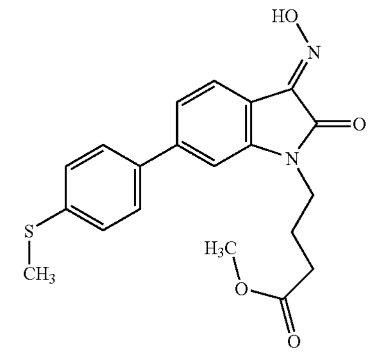 | ND |
| 173 | 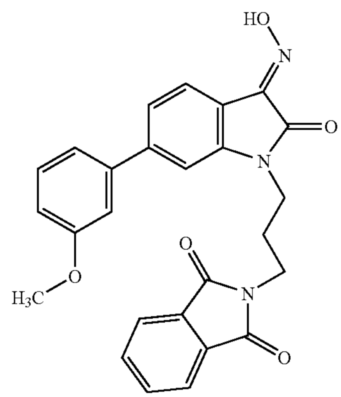 | ND |
| 174 | 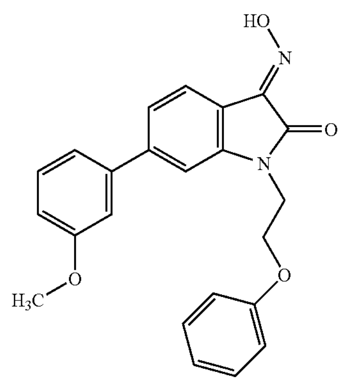 | ND |
| 175 | 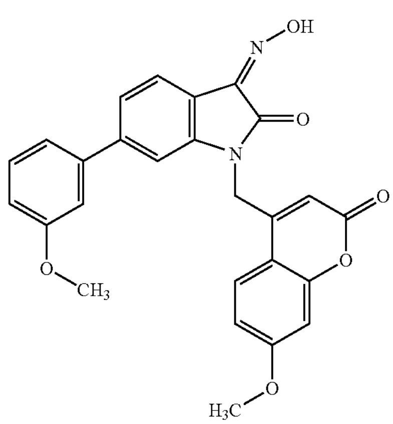 | + |

TABLE 1-continued

| Cmpd | Structure | Ki |
|------|-----------|-----|
| 176 | 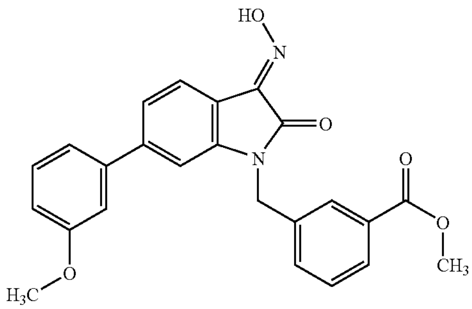 | + |
| 177 | 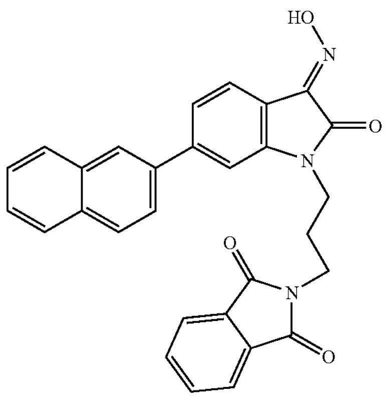 | ND |
| 178 | 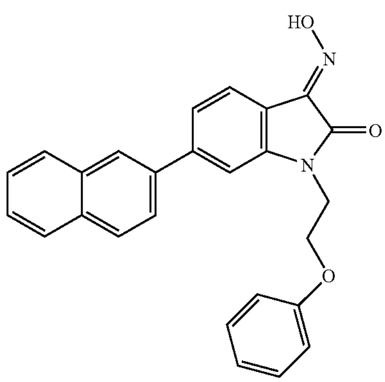 | ND |
| 179 | 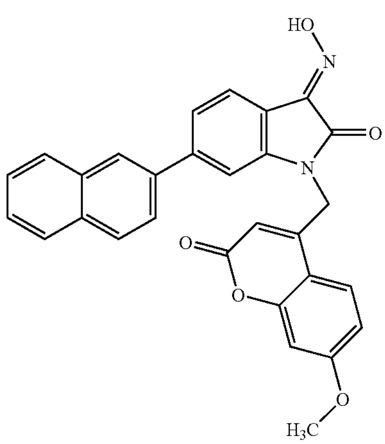 | ND |

TABLE 1-continued
| Cmpd | Structure | Ki |
|---|---|---|
| 180 | 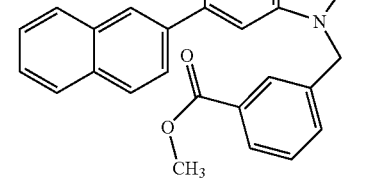 | ND |
| 181 | 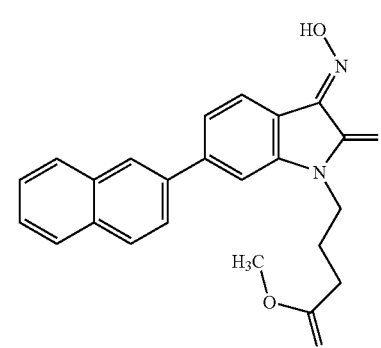 | ND |
| 182 | 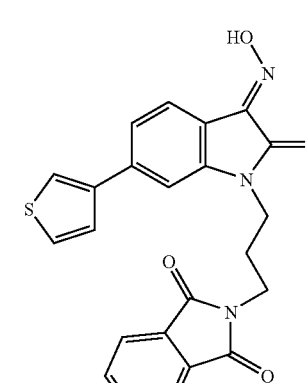 | ND |
| 183 | 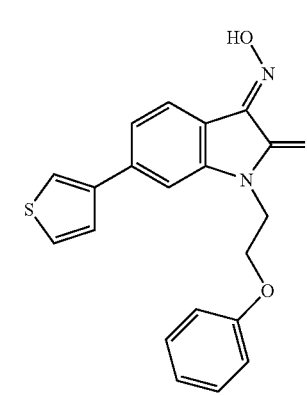 | + |

TABLE 1-continued

| Cmpd | Structure | Ki |
|---|---|---|
| 184 | 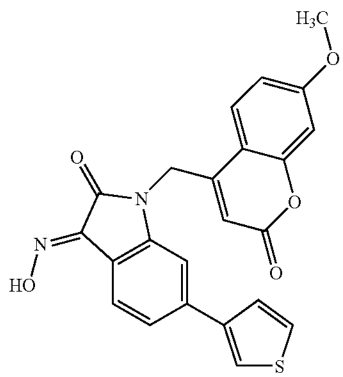 | + |
| 185 | 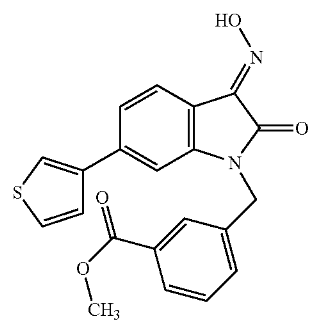 | + |
| 186 | 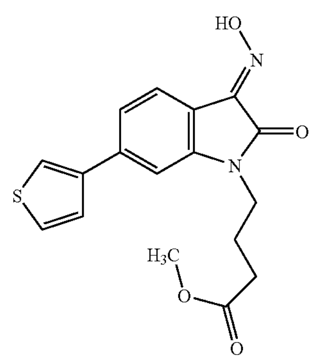 | + |
| 187 | 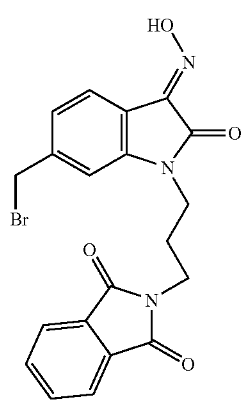 | + |

TABLE 1-continued

| Cmpd | Structure | Ki |
|---|---|---|
| 188 | 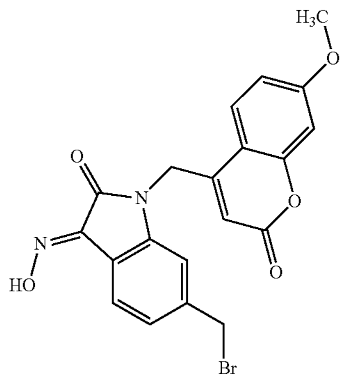 | + |
| 189 | 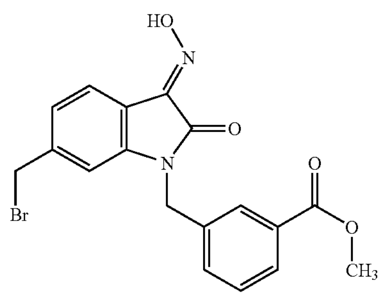 | ++ |
| 190 | 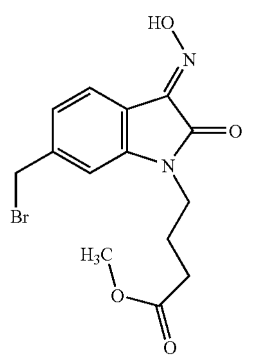 | + |
| 191 | 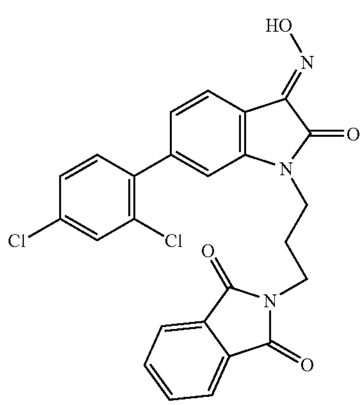 | ND |

TABLE 1-continued
| Cmpd | Structure | Ki |
|---|---|---|
| 192 | 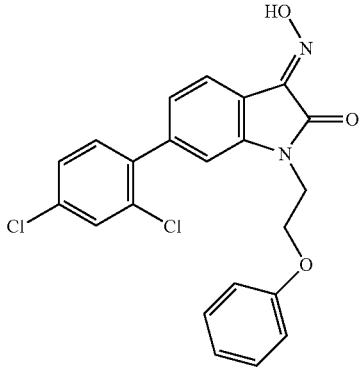 | ND |
| 193 | 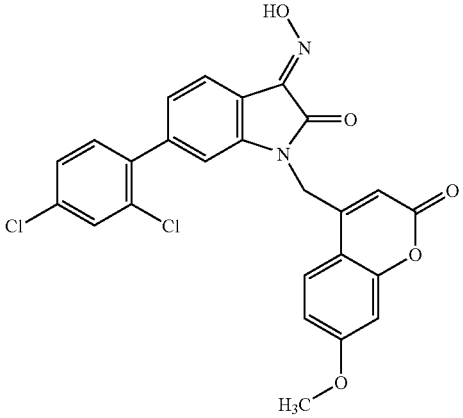 | ND |
| 194 | 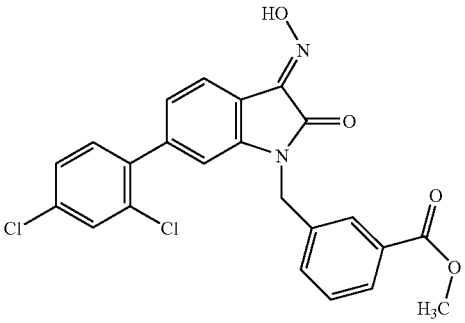 | ND |
| 195 | 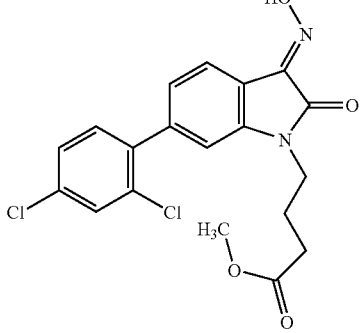 | ND |

TABLE 1-continued
| Cmpd | Structure | Ki |
|---|---|---|
| 196 | 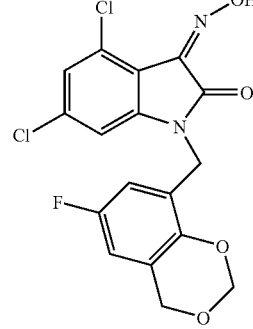 | ++ |
| 197 | 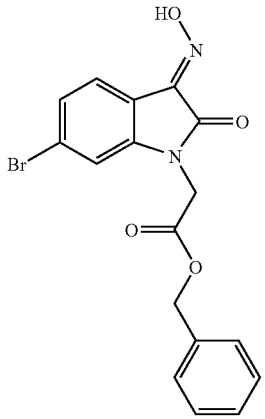 | ND |
| 198 | 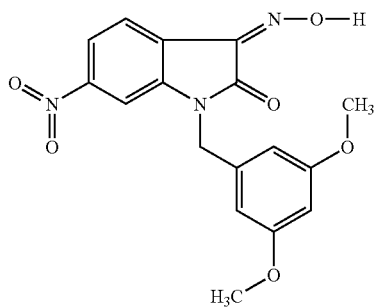 | + |
| 199 | 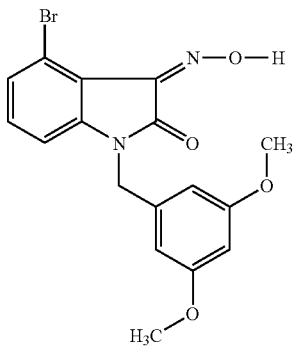 | ++ |

TABLE 1-continued

| Cmpd | Structure | Ki |
|---|---|---|
| 200 | 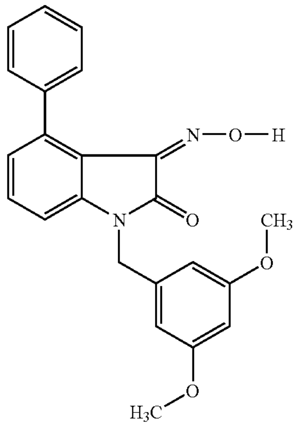 | + |
| 201 | 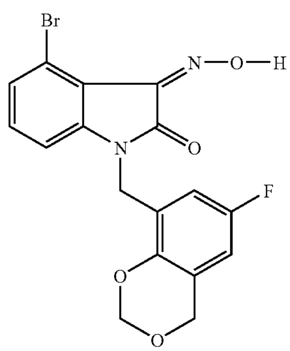 | ++ |
| 202 | 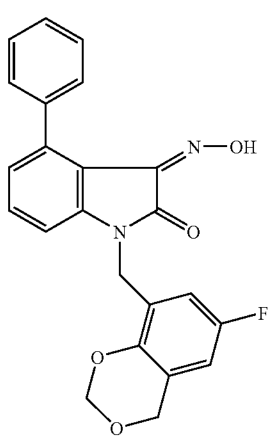 | + |

TABLE 1-continued
| Cmpd | Structure | Ki |
|---|---|---|
| 203 | 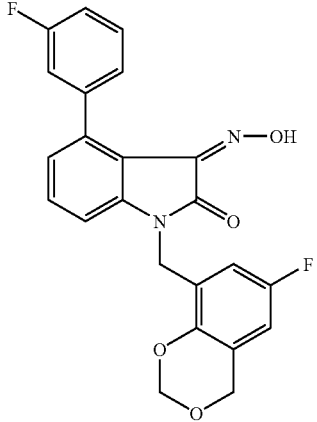 | + |
| 204 | 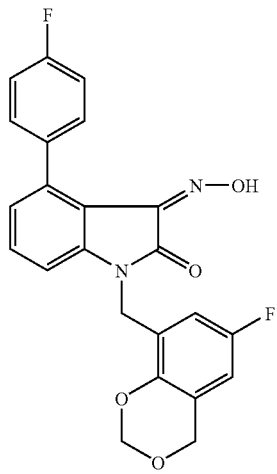 | + |
| 205 | 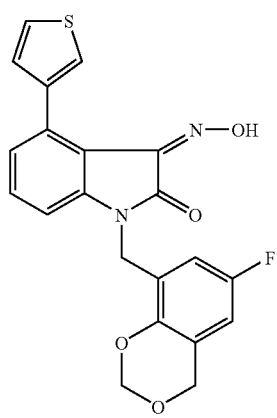 | + |

TABLE 1-continued

| Cmpd | Structure | Ki |
|---|---|---|
| 206 | 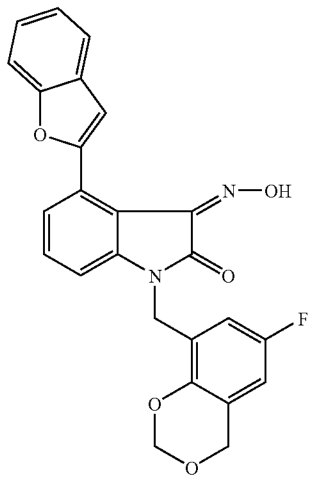 | + |
| 207 | 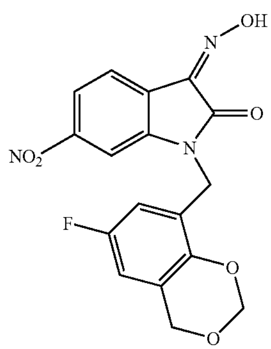 | ++ |
| 208 | 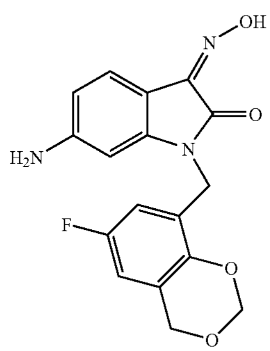 | ++ |
| 209 | 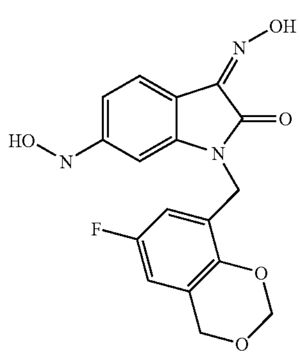 | ++ |

TABLE 1-continued

| Cmpd | Structure | Ki |
|------|-----------|-----|
| 210 | 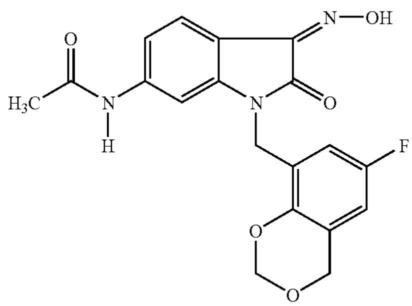 | ++ |
| 211 | 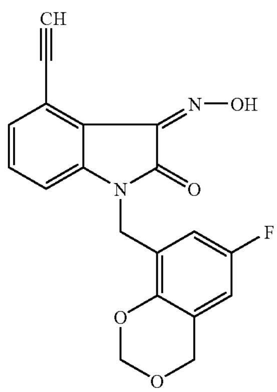 | ND |
| 212 | 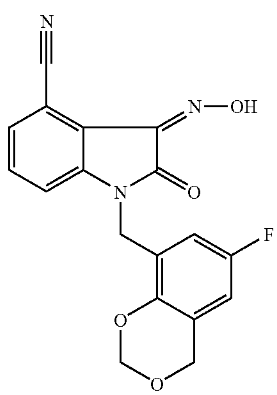 | + |
| 213 | 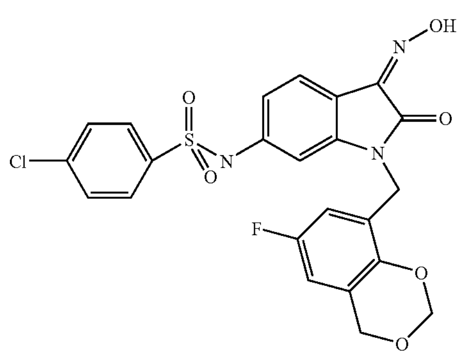 | + |

TABLE 1-continued

| Cmpd | Structure | Ki |
|------|-----------|-----|
| 214 | 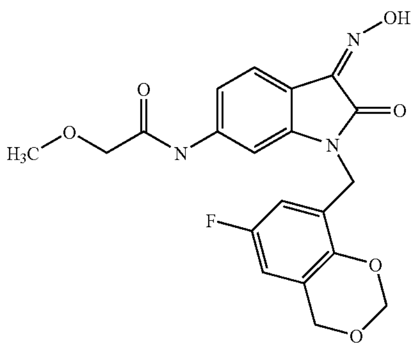 | ++ |
| 215 | 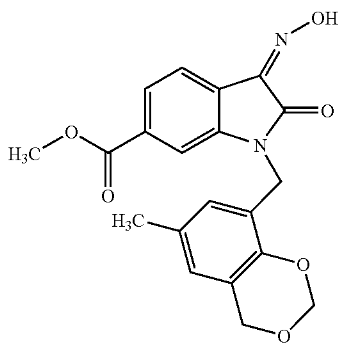 | ++ |
| 216 | 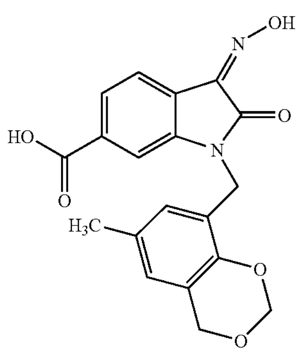 | ++ |
| 217 | 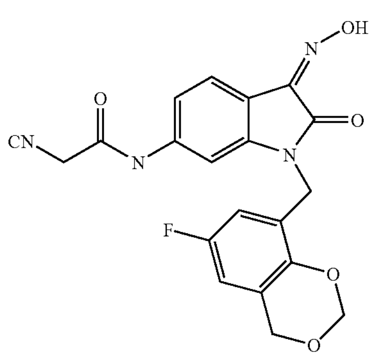 | ++ |

TABLE 1-continued

| Cmpd | Structure | Ki |
|---|---|---|
| 218 | 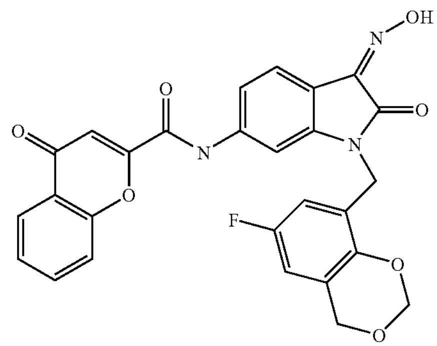 | + |
| 219 | 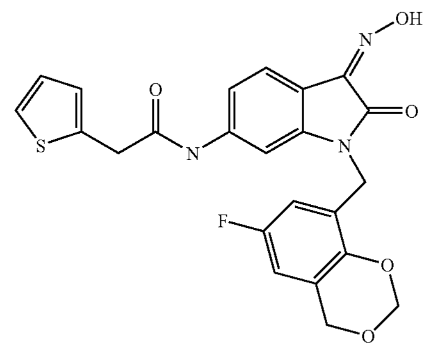 | ++ |
| 220 | 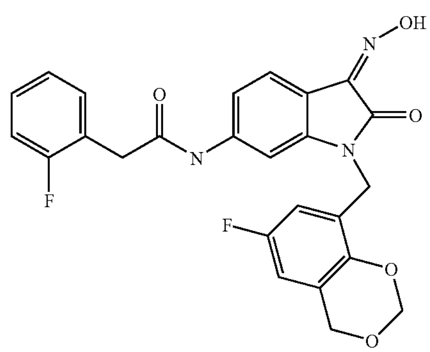 | ++ |
| 221 | 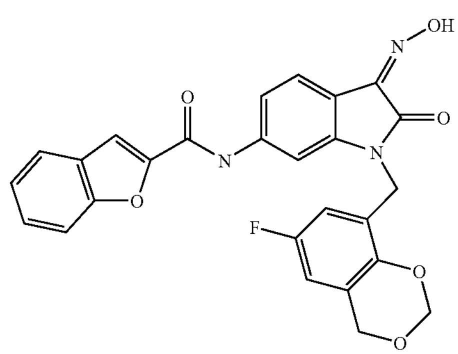 | ++ |

TABLE 1-continued
| Cmpd | Structure | Ki |
|------|-----------|-----|
| 222 | 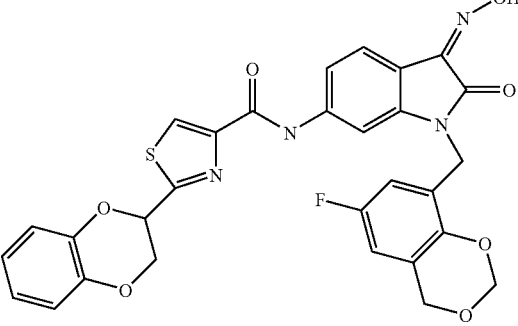 | + |
| 223 | 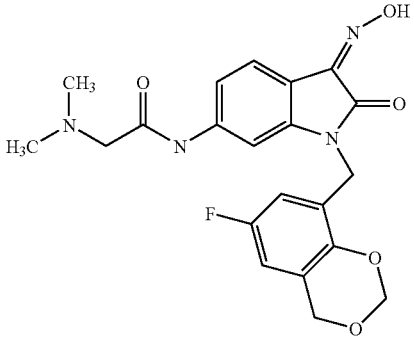 | + |
| 224 | 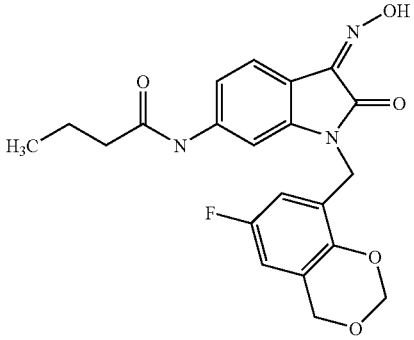 | ++ |
| 225 | 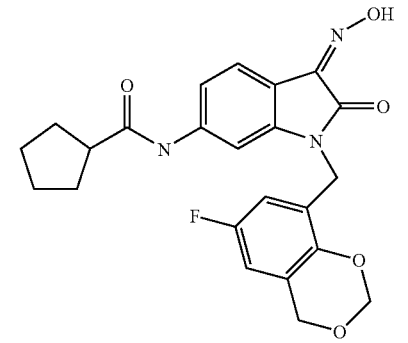 | ++ |

TABLE 1-continued

| Cmpd | Structure | Ki |
|---|---|---|
| 226 | 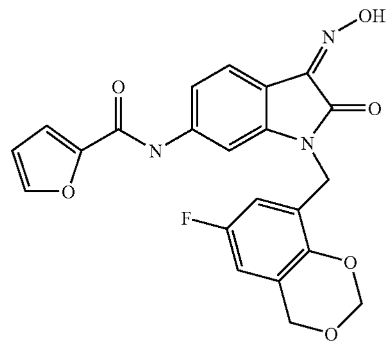 | ++ |
| 227 | 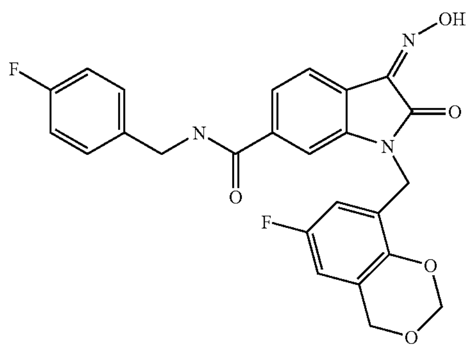 | ++ |
| 228 | 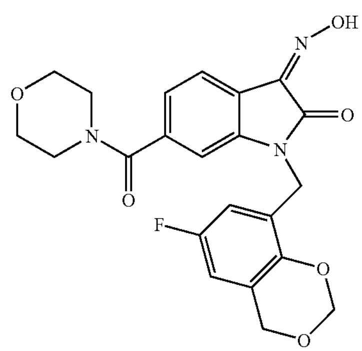 | + |
| 229 | 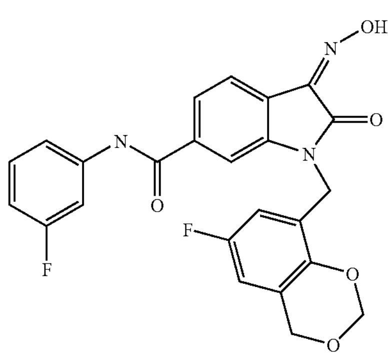 | + |

TABLE 1-continued

| Cmpd | Structure | Ki |
|------|-----------|-----|
| 230 | 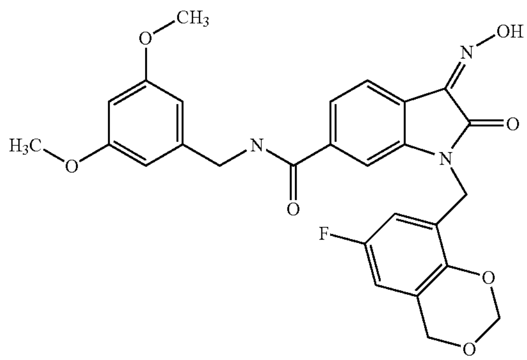 | + |
| 231 | 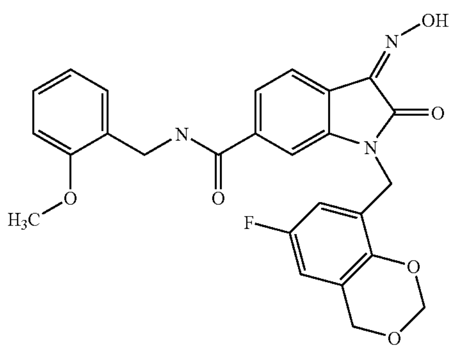 | + |
| 232 | 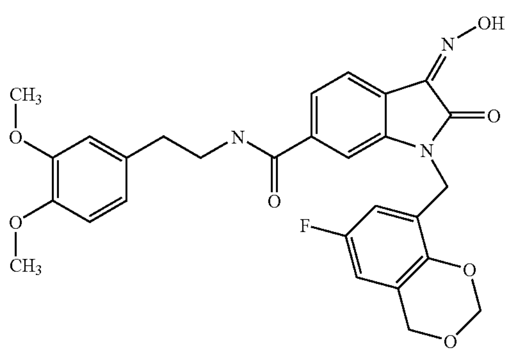 | + |
| 233 | 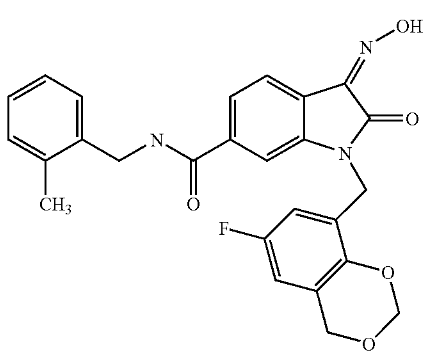 | + |

TABLE 1-continued

| Cmpd | Structure | Ki |
|------|-----------|-----|
| 234 | 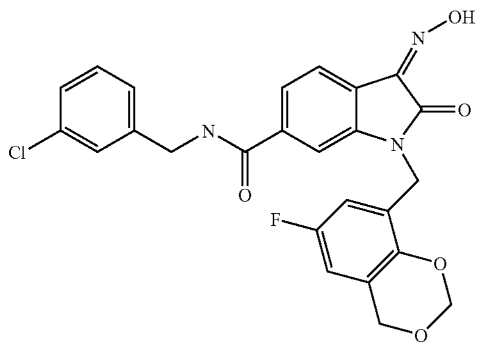 | + |
| 235 | 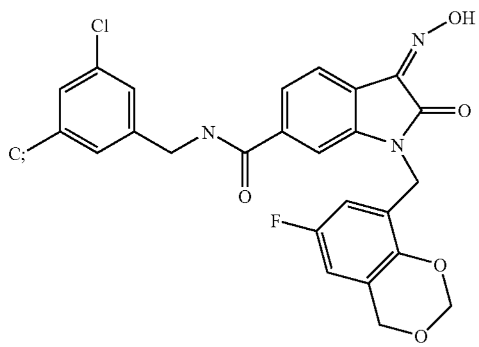 | + |
| 236 | 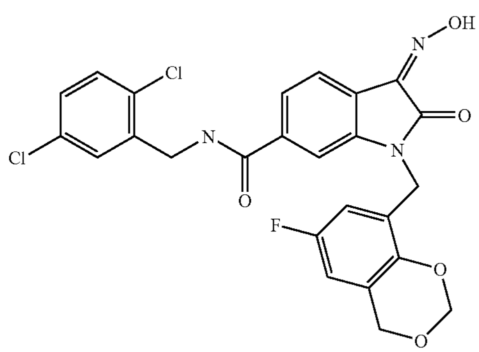 | + |
| 237 | 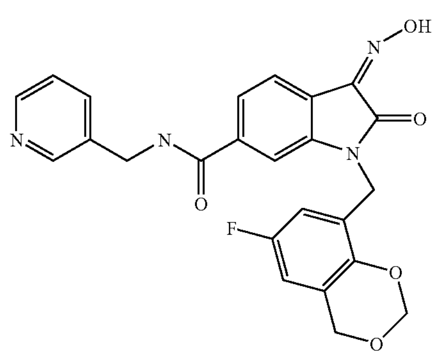 | + |

TABLE 1-continued

| Cmpd | Structure | Ki |
|---|---|---|
| 238 | 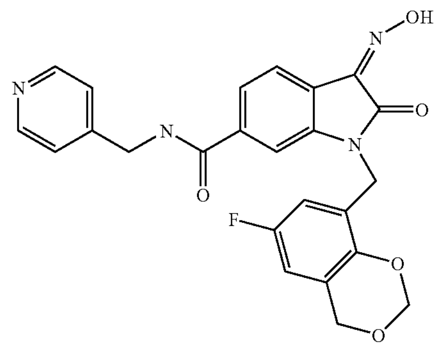 | + |
| 239 | 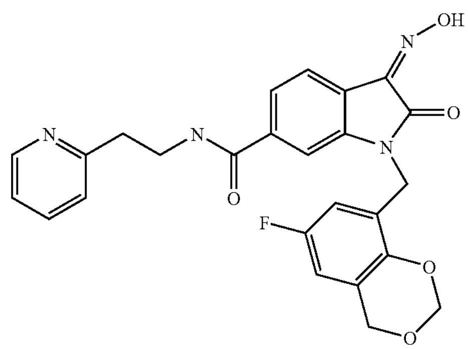 | + |
| 240 | 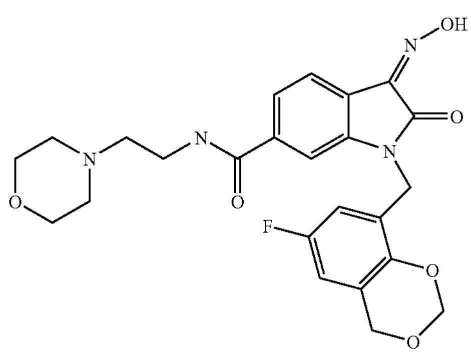 | + |
| 241 | 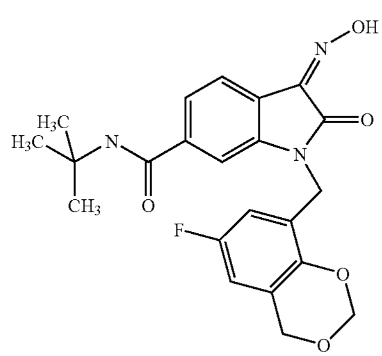 | + |

TABLE 1-continued

| Cmpd | Structure | Ki |
|---|---|---|
| 242 | 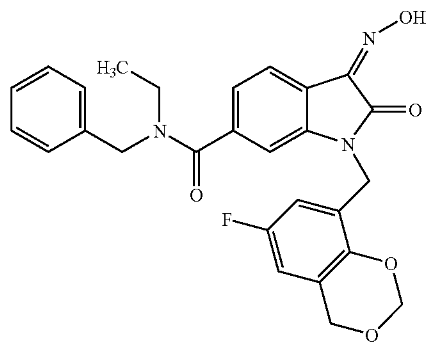 | + |
| 243 | 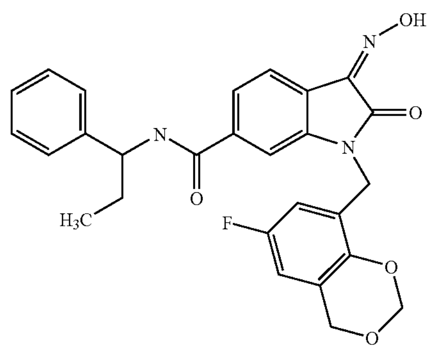 | + |
| 244 | 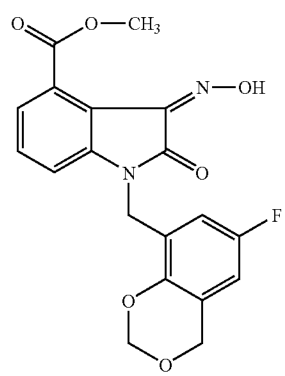 | + |
| 245 | 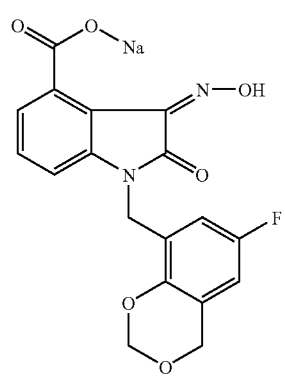 | + |

TABLE 1-continued
| Cmpd | Structure | Ki |
|---|---|---|
| 246 | 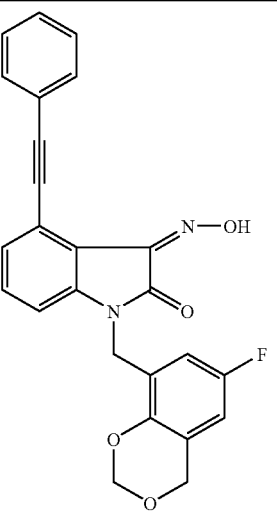 | + |
| 247 | 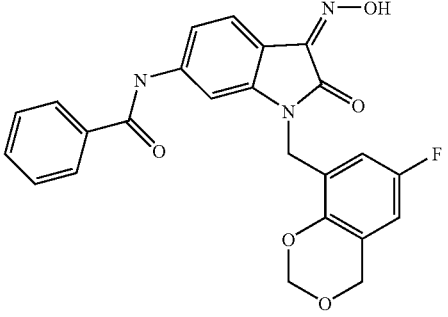 | ++ |
| 248 | 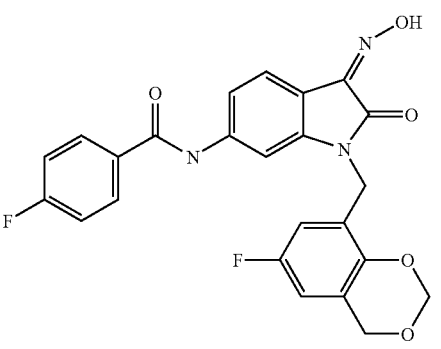 | ++ |
| 249 | 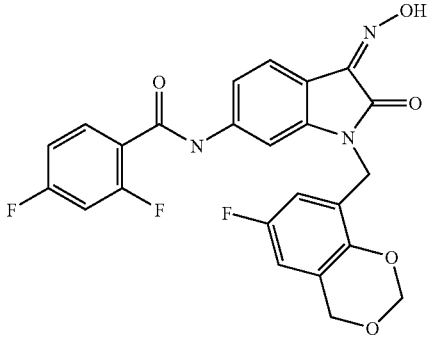 | ++ |

TABLE 1-continued

| Cmpd | Structure | Ki |
|---|---|---|
| 250 | 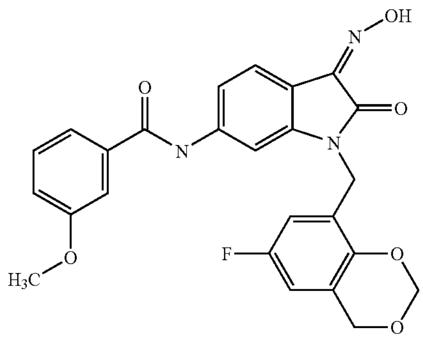 | ++ |
| 251 | 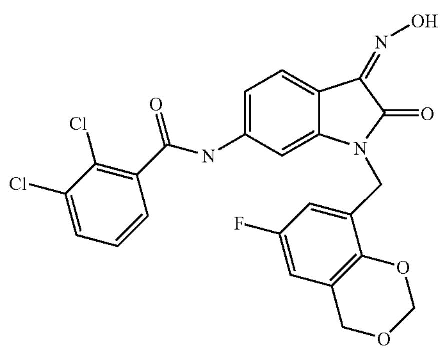 | ++ |
| 252 | 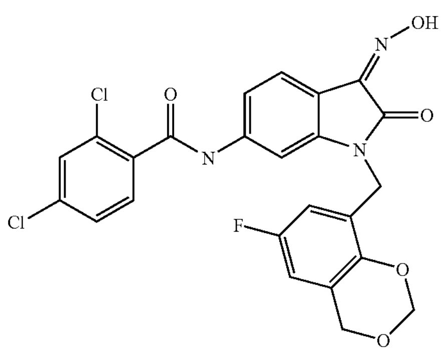 | + |
| 253 | 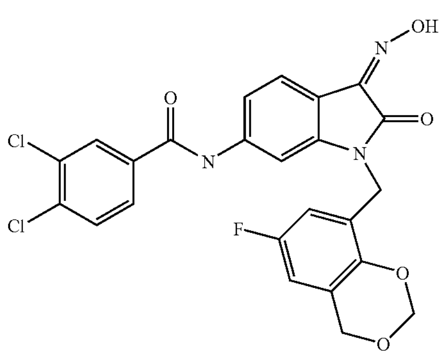 | + |

TABLE 1-continued

| Cmpd | Structure | Ki |
|---|---|---|
| 254 | 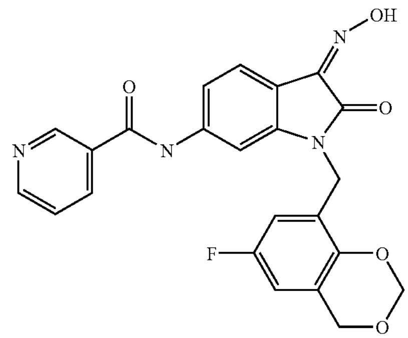 | ++ |
| 255 | 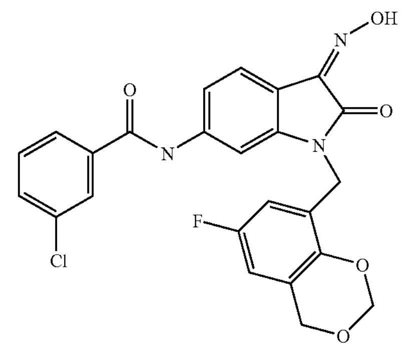 | ++ |
| 256 | 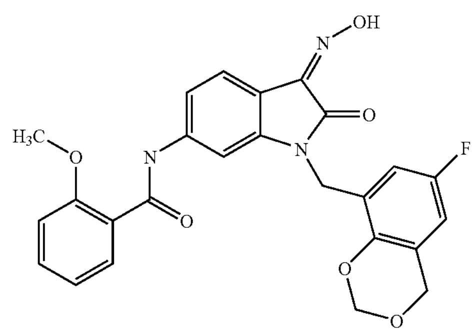 | ++ |
| 257 | 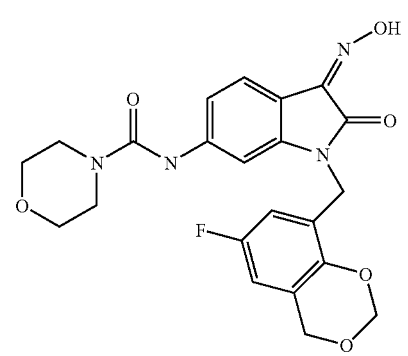 | + |

TABLE 1-continued

| Cmpd | Structure | Ki |
|------|-----------|----|
| 258 | 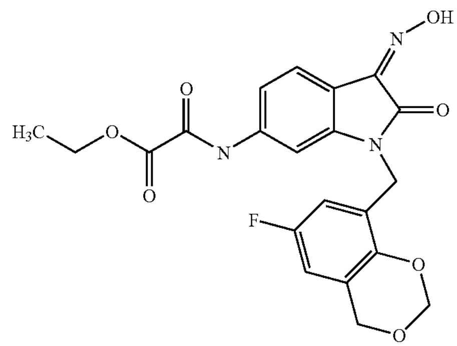 | ++ |
| 259 | 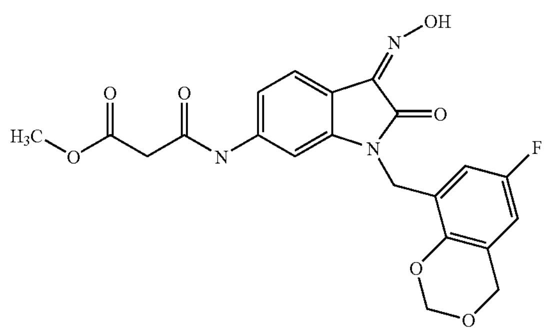 | ++ |
| 260 | 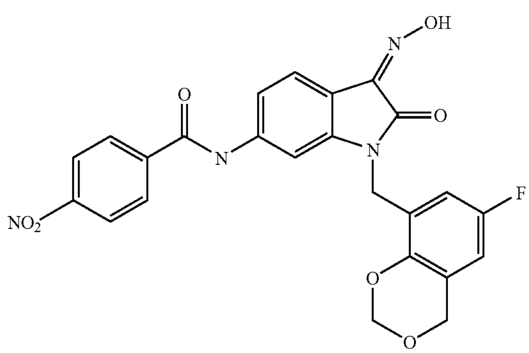 | ++ |
| 261 | 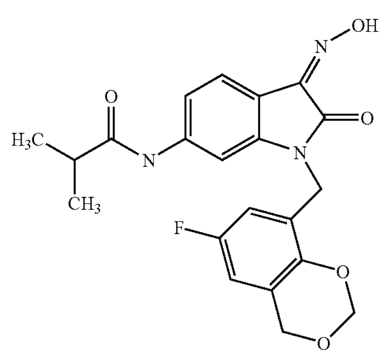 | ++ |

TABLE 1-continued

| Cmpd | Structure | Ki |
|------|-----------|-----|
| 262 | 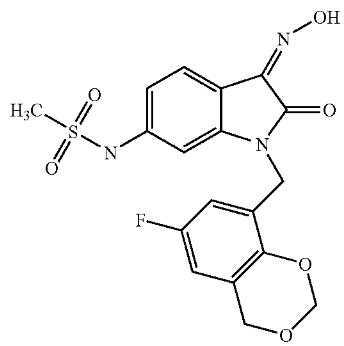 | ++ |
| 263 | 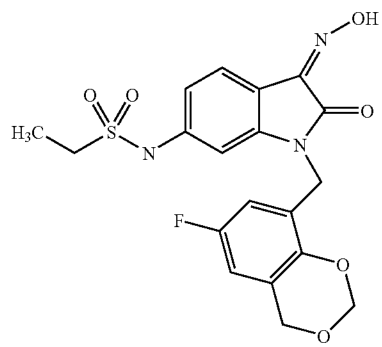 | ++ |
| 264 | 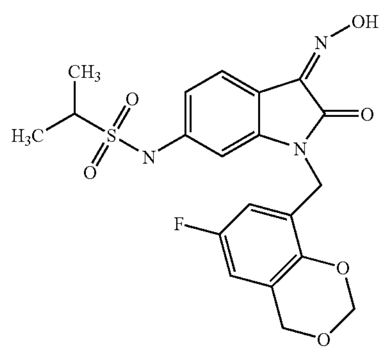 | + |
| 265 | 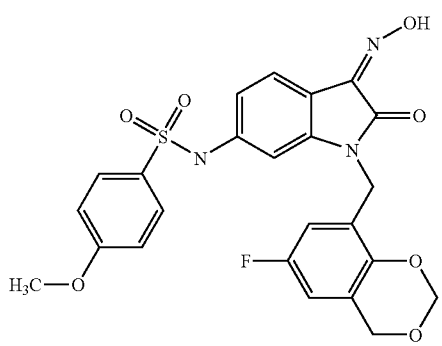 | + |

TABLE 1-continued

| Cmpd | Structure | Ki |
|---|---|---|
| 266 | 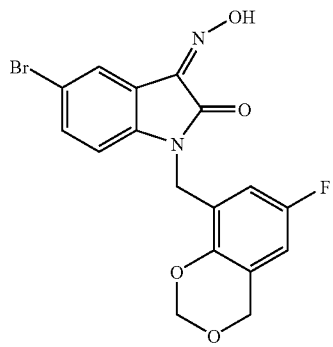 | ND |
| 267 | 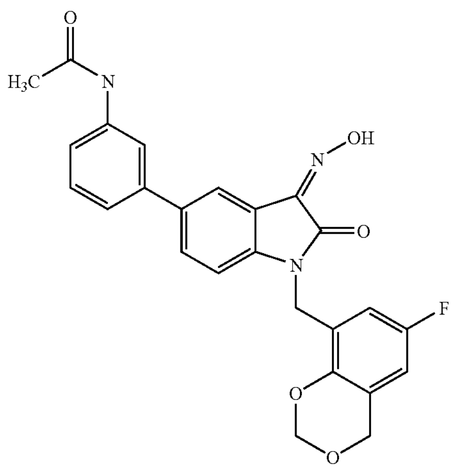 | ND |
| 268 | 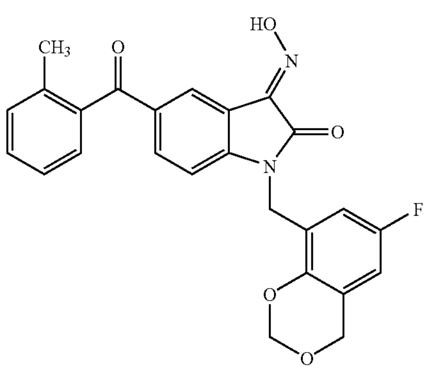 | ++ |
| 269 | 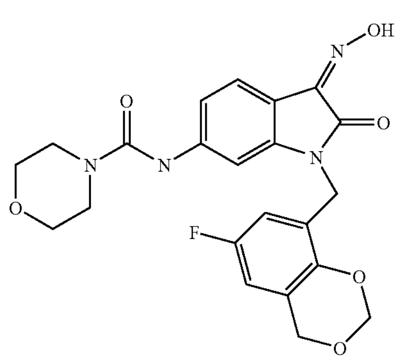 | ++ |

TABLE 1-continued

| Cmpd | Structure | Ki |
|---|---|---|
| 270 | 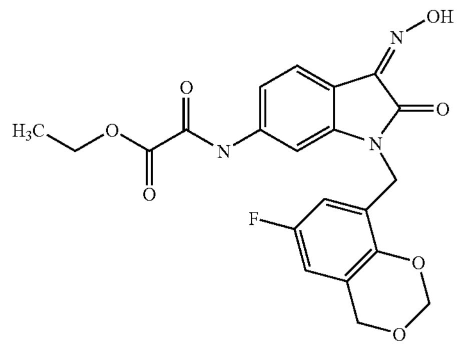 | ++ |
| 271 | 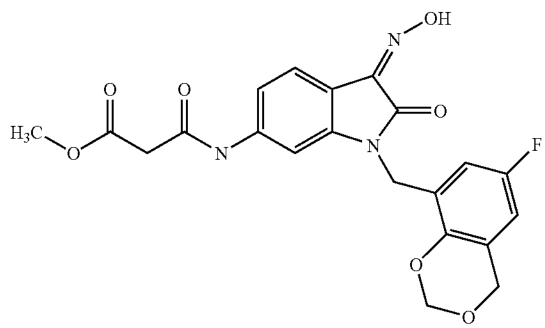 | ++ |
| 272 | 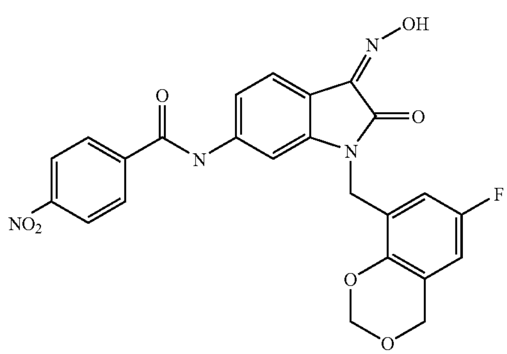 | ++ |
| 273 | 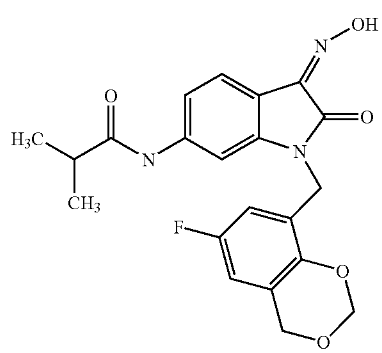 | ++ |

TABLE 1-continued

| Cmpd | Structure | Ki |
|------|-----------|-----|
| 274 | 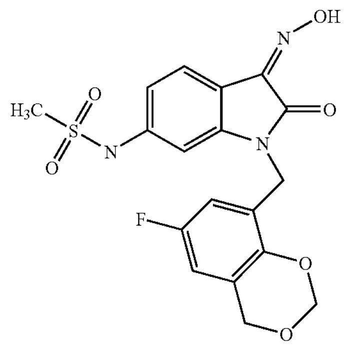 | ++ |
| 275 | 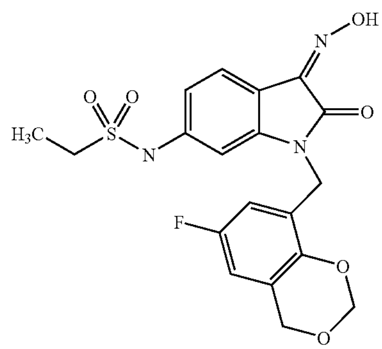 | ++ |
| 276 | 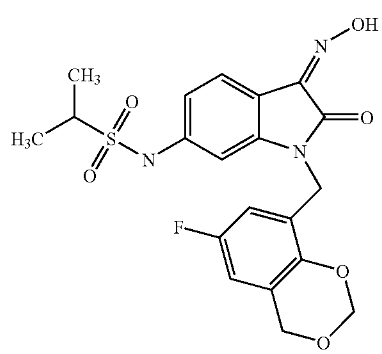 | + |
| 277 | 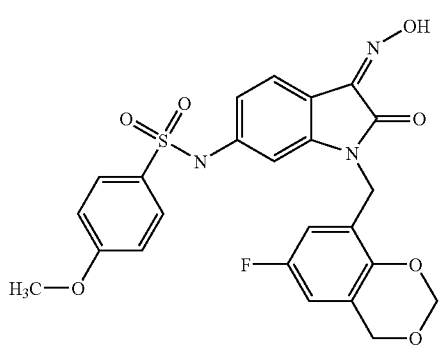 | + |

TABLE 1-continued

| Cmpd | Structure | Ki |
|------|-----------|-----|
| 278 | 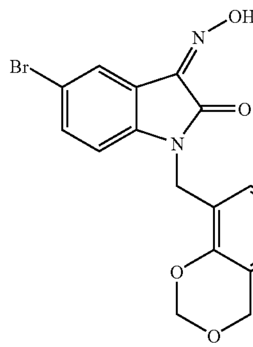 | ++ |
| 279 | 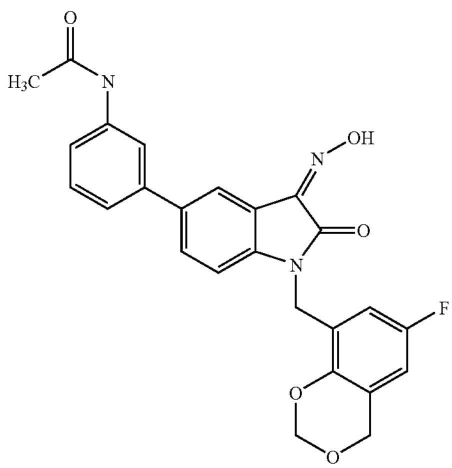 | + |
| 280 | 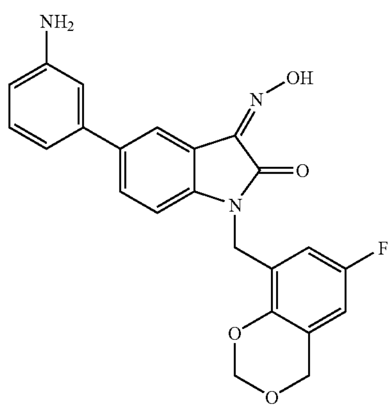 | + |
| 281 | 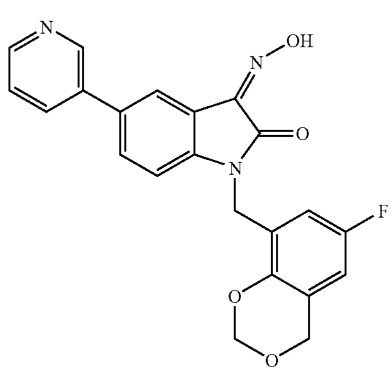 | + |

TABLE 1-continued
| Cmpd | Structure | Ki |
|---|---|---|
| 282 | 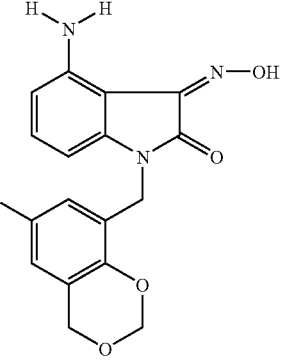 | + |
| 283 | 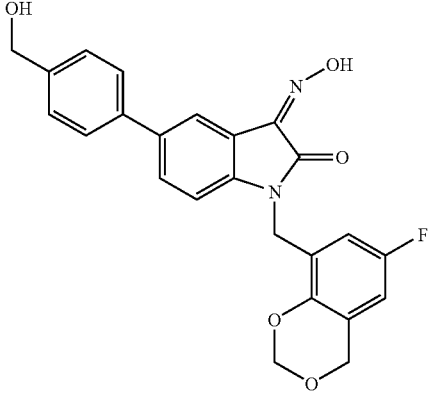 | + |
| 284 | 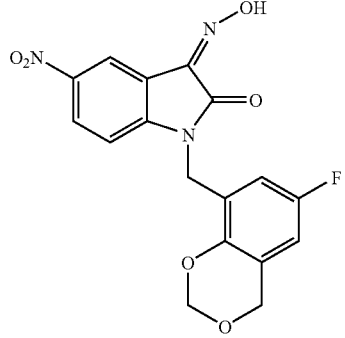 | + |
| 285 | 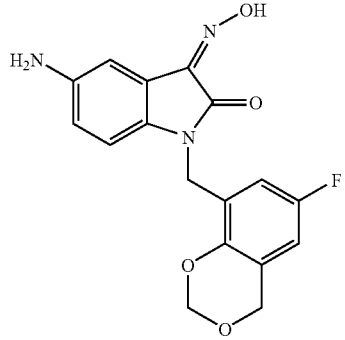 | + |

TABLE 1-continued

| Cmpd | Structure | Ki |
|---|---|---|
| 286 | 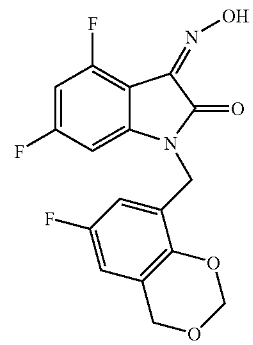 | ++ |
| 287 | 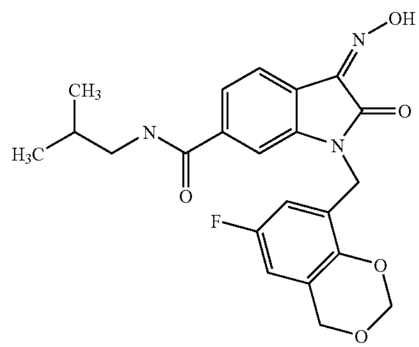 | + |
| 288 | 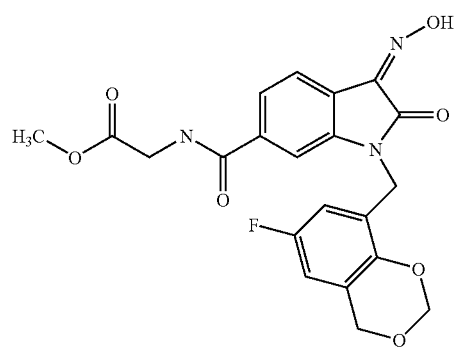 | + |
| 289 | 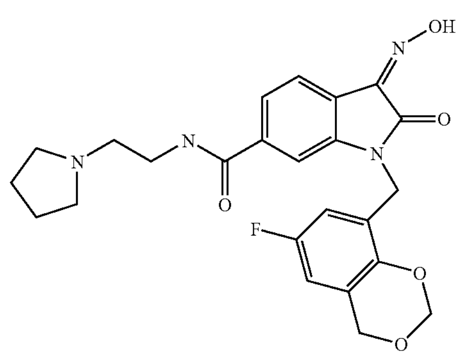 | + |

TABLE 1-continued
| Cmpd | Structure | Ki |
|---|---|---|
| 290 | 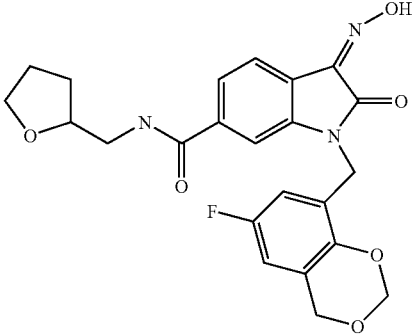 | + |
| 291 | 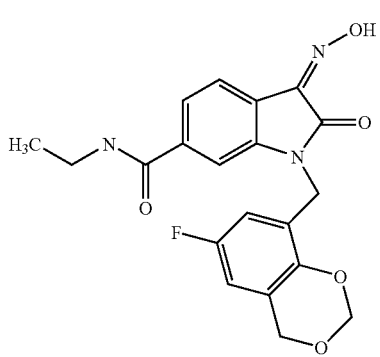 | + |
| 292 | 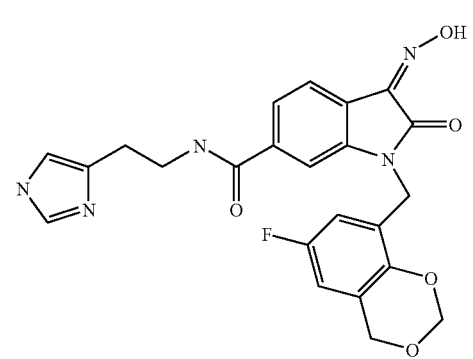 | + |
| 293 | 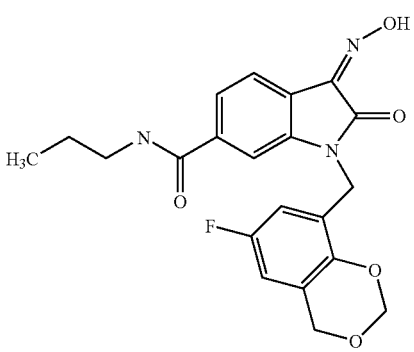 | + |

TABLE 1-continued

| Cmpd | Structure | Ki |
|------|-----------|-----|
| 294 | 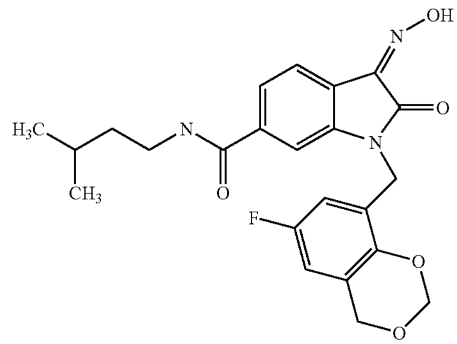 | + |
| 295 | 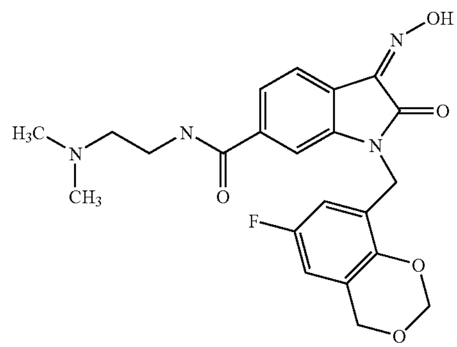 | + |
| 296 | 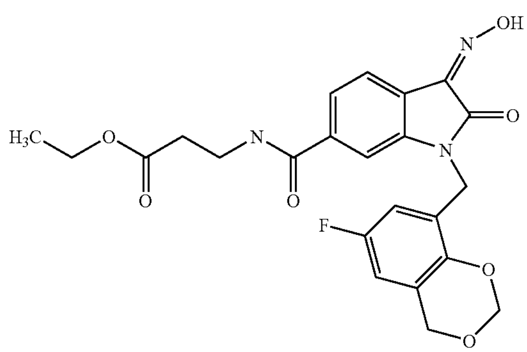 | + |
| 297 | 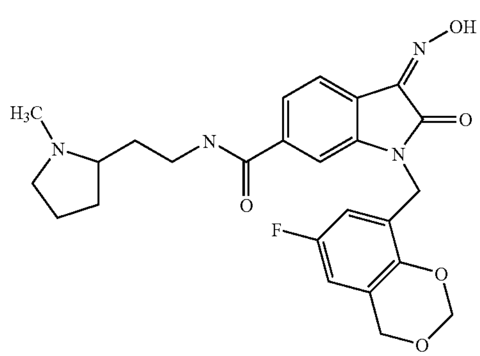 | + |

TABLE 1-continued
| Cmpd | Structure | Ki |
|---|---|---|
| 298 | 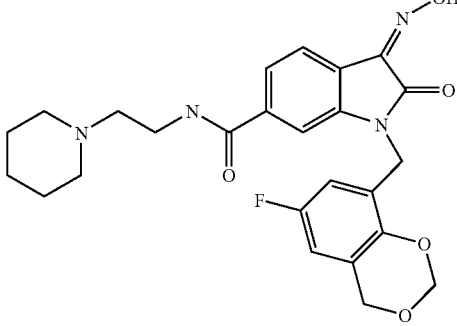 | + |
| 299 | 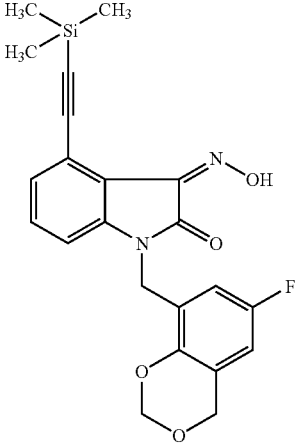 | + |
| 300 | 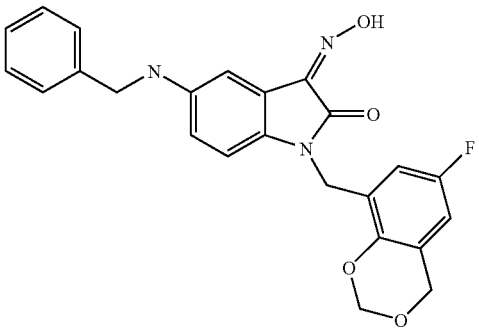 | + |
| 301 | 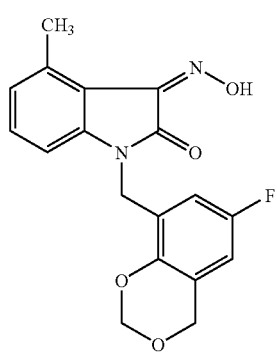 | ++ |

TABLE 1-continued
| Cmpd | Structure | Ki |
|------|-----------|-----|
| 302 | 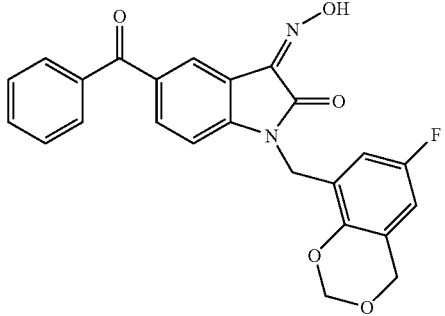 | + |
| 303 | 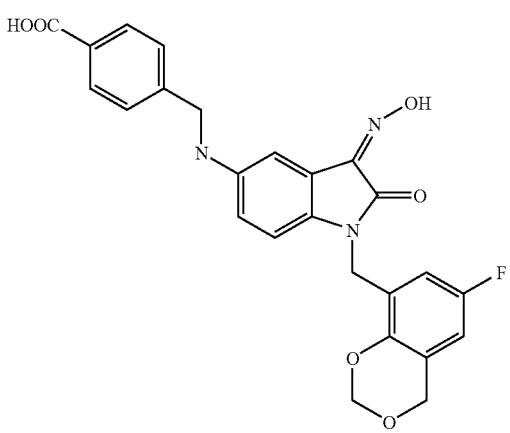 | + |
| 304 | 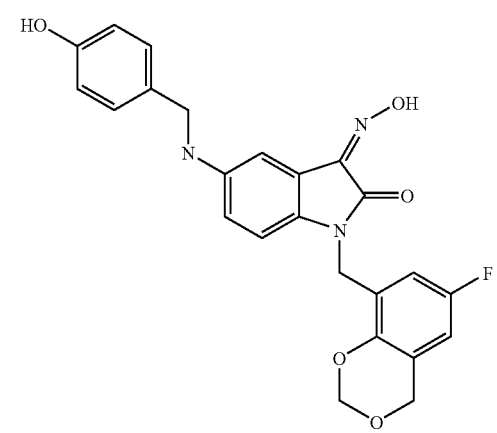 | + |

TABLE 1-continued
| Cmpd | Structure | Ki |
|---|---|---|
| 305 | 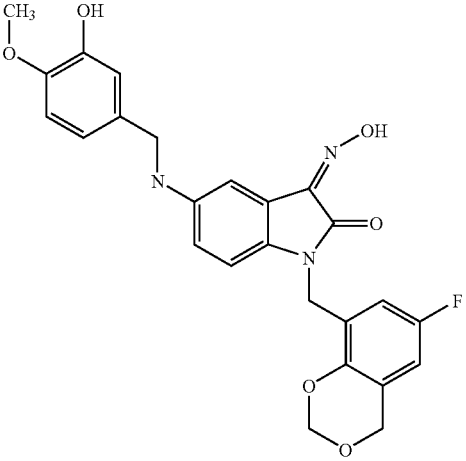 | + |
| 306 | 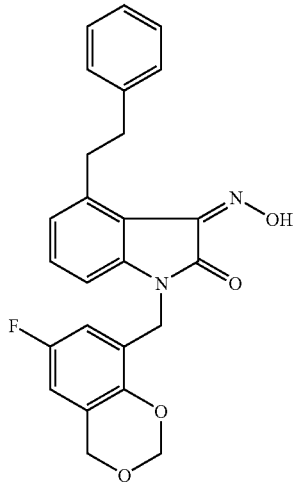 | + |
| 307 | 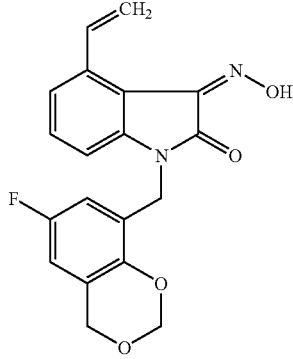 | ++ |

TABLE 1-continued
| Cmpd | Structure | Ki |
|------|-----------|-----|
| 308 | 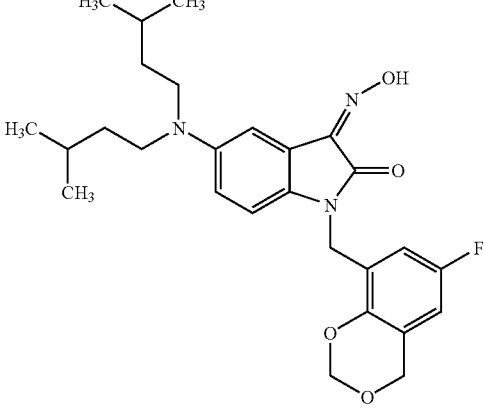 | + |
| 309 | 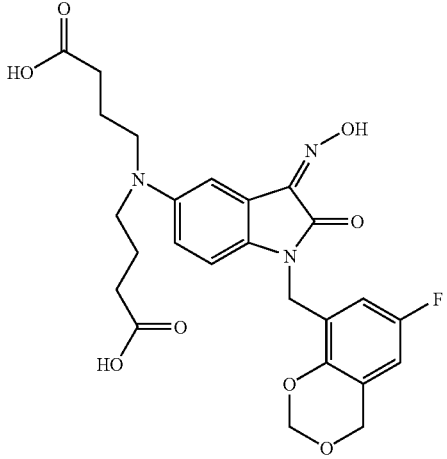 | + |
| 310 | 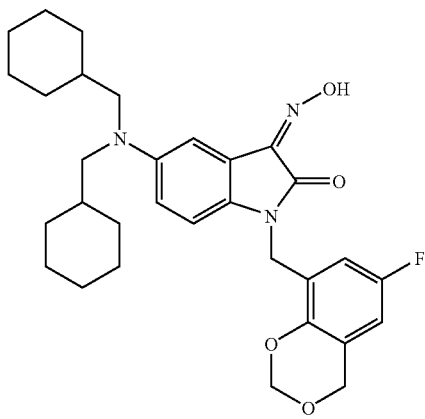 | + |

TABLE 1-continued

| Cmpd | Structure | Ki |
|------|-----------|-----|
| 311 | 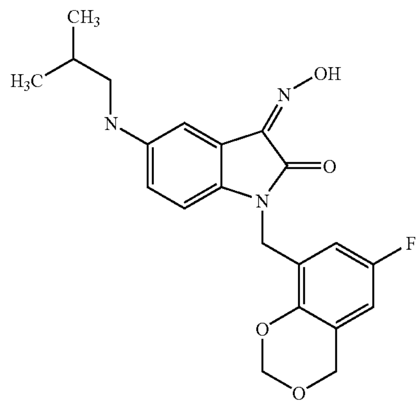 | + |
| 312 | 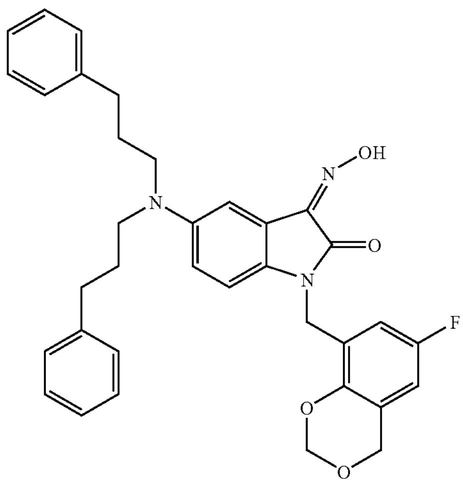 | + |
| 313 | 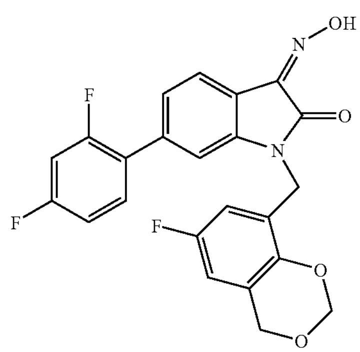 | ++ |
| 314 | 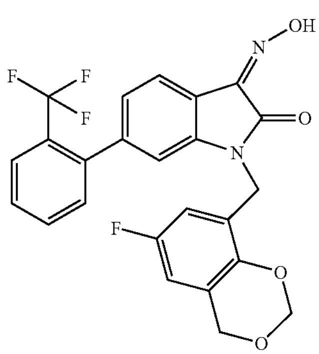 | + |

TABLE 1-continued

| Cmpd | Structure | Ki |
|------|-----------|-----|
| 315 | 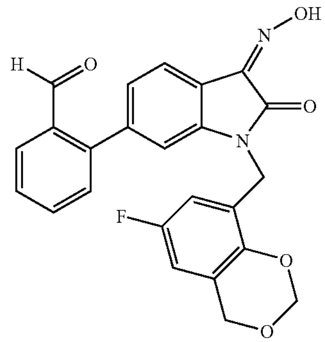 | ++ |
| 316 | 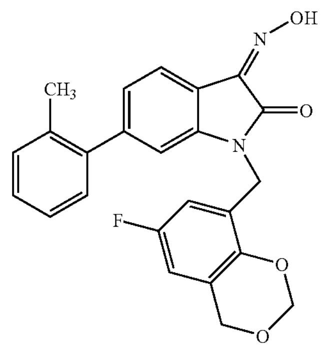 | ++ |
| 317 | 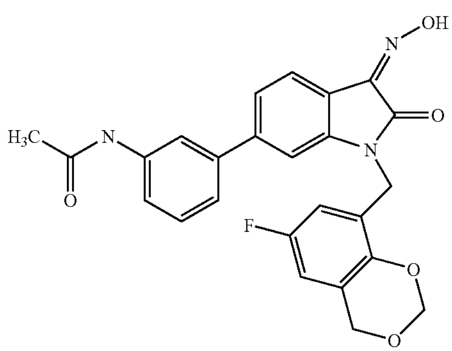 | ++ |
| 318 | 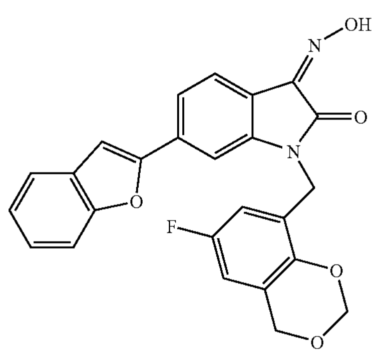 | ++ |

TABLE 1-continued
| Cmpd | Structure | Ki |
|------|-----------|-----|
| 319 | 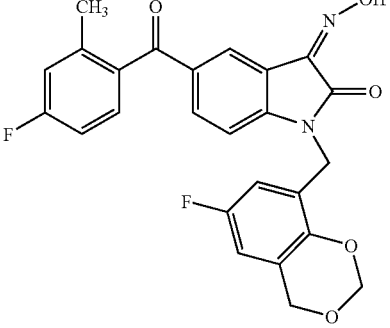 | ++ |
| 320 | 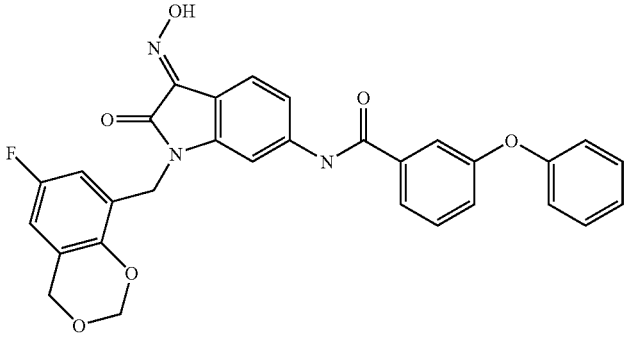 | + |
| 321 | 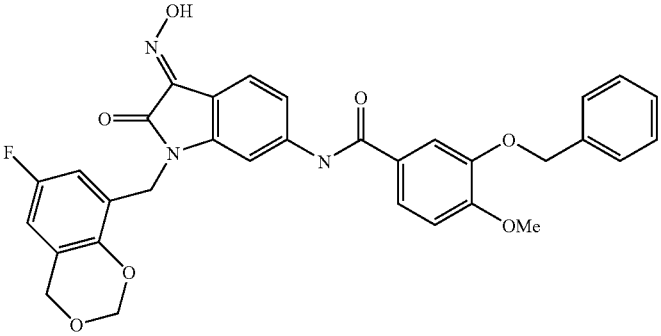 | ++ |
| 322 | 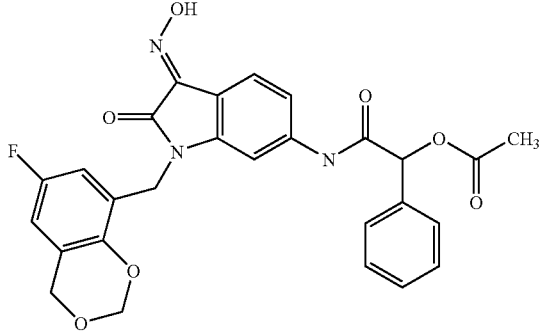 | + |

TABLE 1-continued

| Cmpd | Structure | Ki |
|---|---|---|
| 323 | 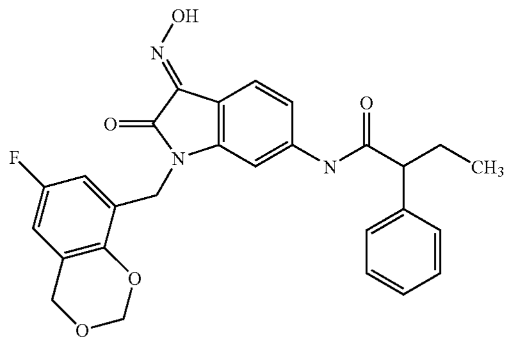 | ++ |
| 324 | 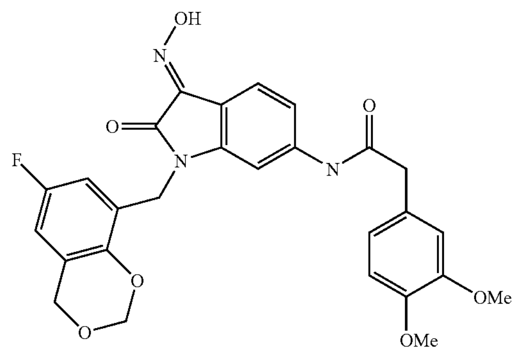 | + |
| 325 | 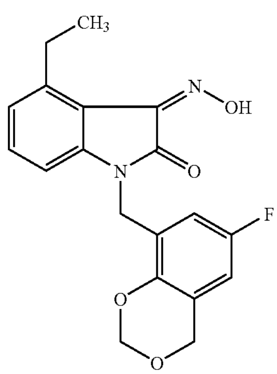 | + |
| 326 | 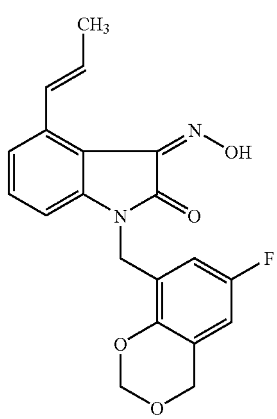 | ++ |

TABLE 1-continued

| Cmpd | Structure | Ki |
|------|-----------|-----|
| 327 | 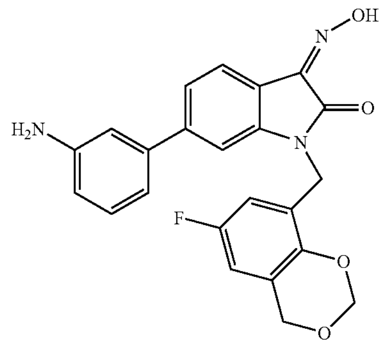 | ++ |
| 328 | 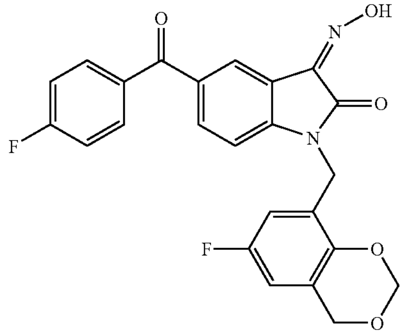 | + |
| 329 | 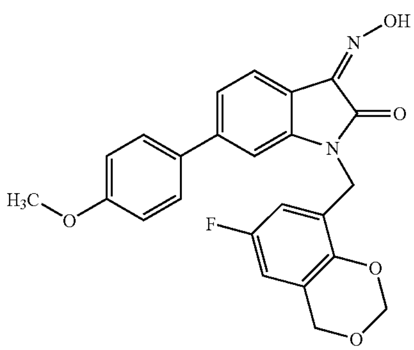 | + |
| 330 | 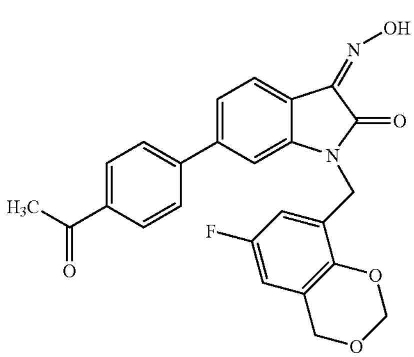 | ++ |

TABLE 1-continued

| Cmpd | Structure | Ki |
|------|-----------|-----|
| 331 | 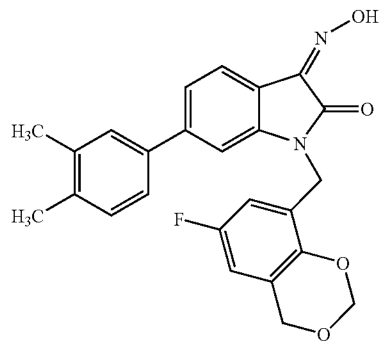 | ++ |
| 332 | 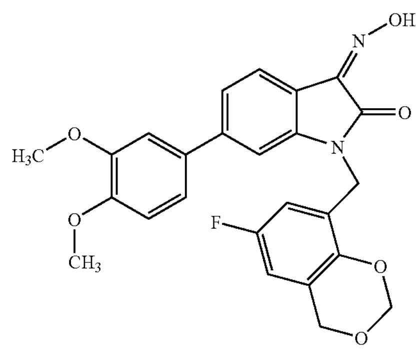 | ++ |
| 333 | 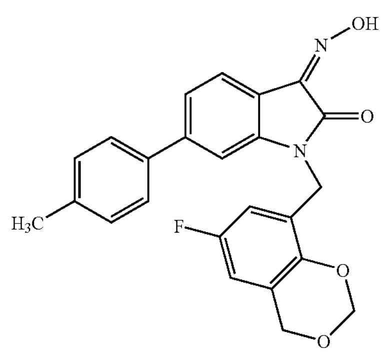 | + |
| 334 | 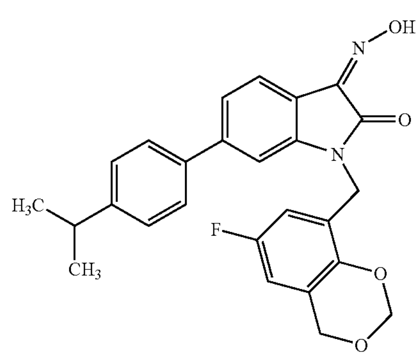 | + |

TABLE 1-continued
| Cmpd | Structure | Ki |
|------|-----------|-----|
| 335 | 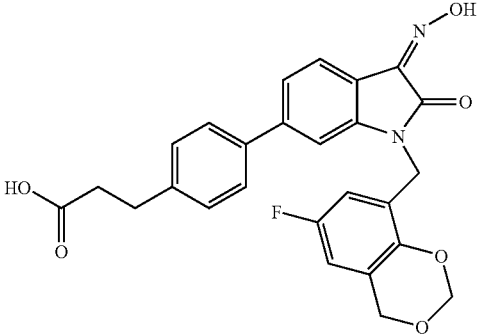 | ++ |
| 336 | 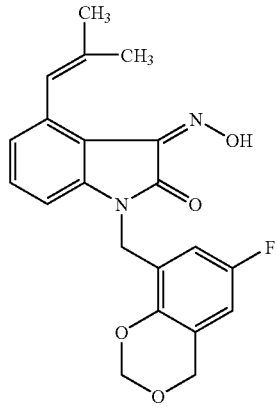 | ++ |
| 337 | 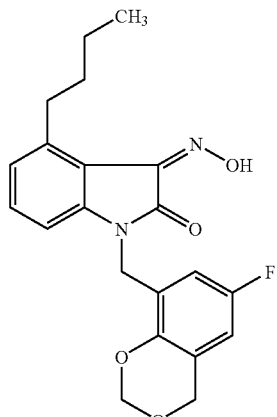 | ++ |
| 338 | 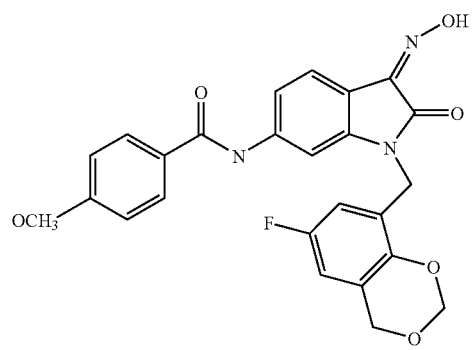 | + |

TABLE 1-continued

| Cmpd | Structure | Ki |
|------|-----------|-----|
| 339 | 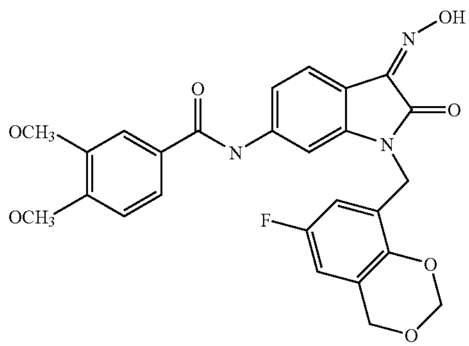 | + |
| 340 | 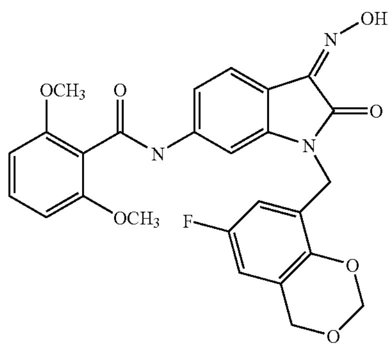 | + |
| 341 | 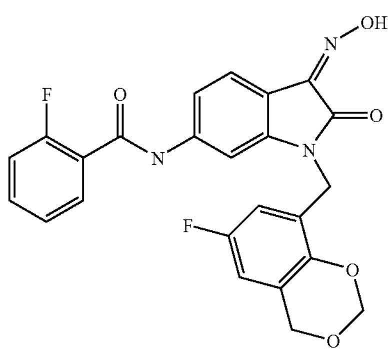 | ++ |
| 342 | 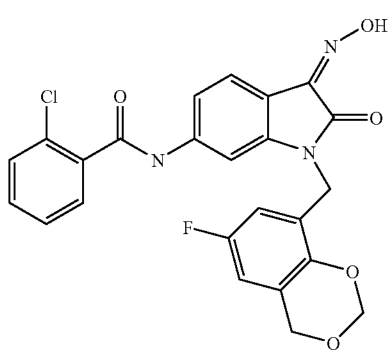 | ++ |

TABLE 1-continued

| Cmpd | Structure | Ki |
|------|-----------|-----|
| 343 | 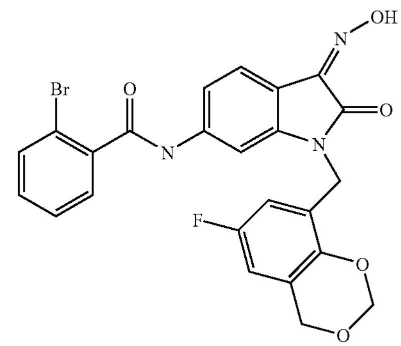 | ++ |
| 344 | 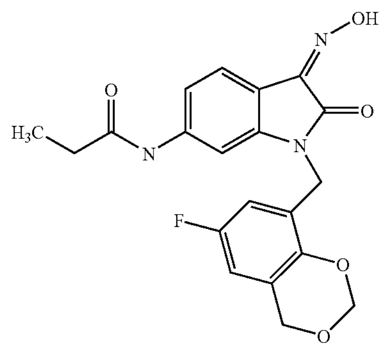 | ++ |
| 345 | 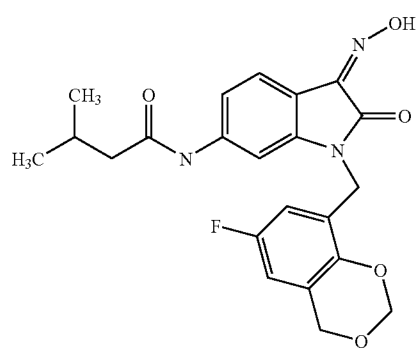 | ++ |
| 346 | 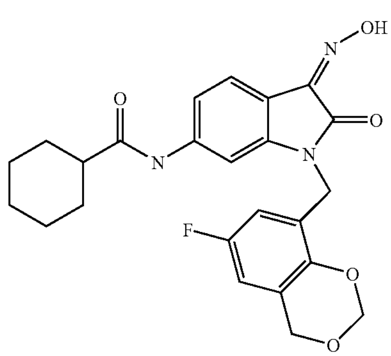 | + |

TABLE 1-continued

| Cmpd | Structure | Ki |
|---|---|---|
| 347 | 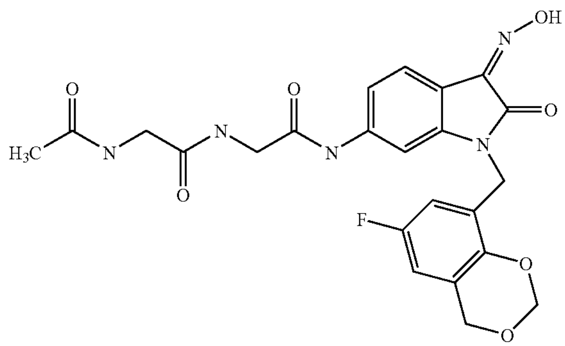 | + |
| 348 | 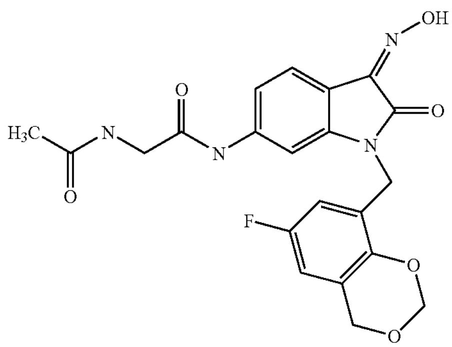 | + |
| 349 | 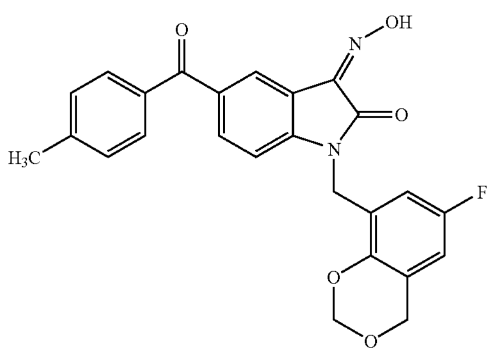 | + |
| 350 | 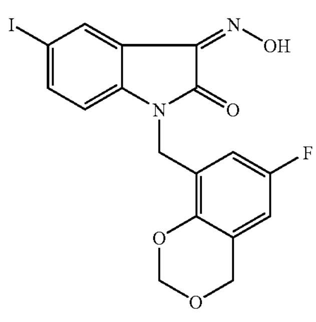 | ND |

TABLE 1-continued

| Cmpd | Structure | Ki |
|------|-----------|-----|
| 351 | 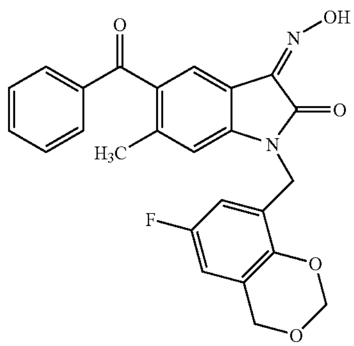 | + |
| 352 | 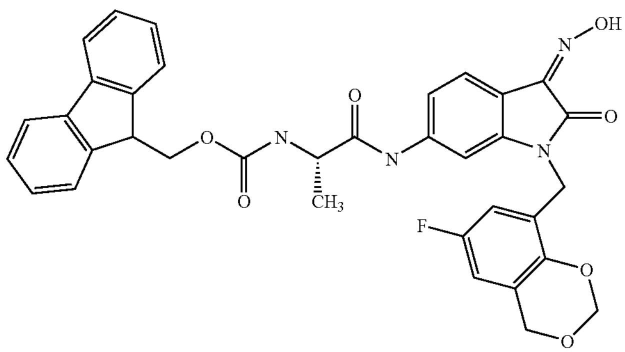 | + |
| 353 | 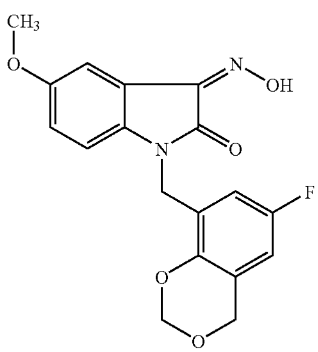 | ND |
| 354 | 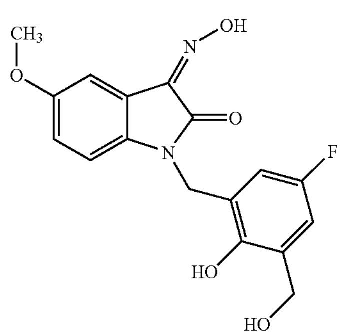 | ND |

TABLE 1-continued

| Cmpd | Structure | Ki |
|---|---|---|
| 355 | 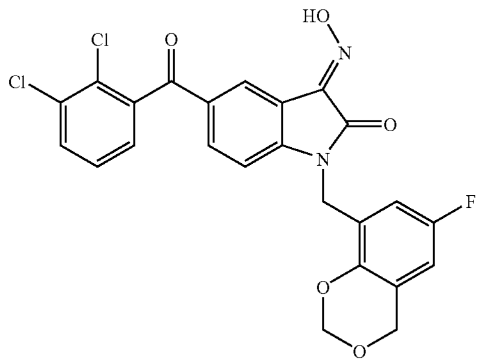 | ++ |
| 356 | 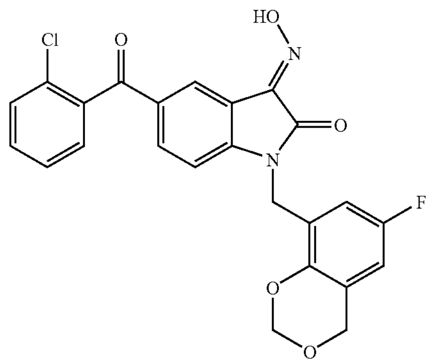 | ++ |

According to another embodiment, the present invention provides methods of producing JNK inhibitors of the formulae I and II. Synthesis schemes for specific compounds are described in Examples 1 and 2.

Compounds of formula I, wherein W is N, may be prepared by standard synthetic methods, such as those described in Examples 1 and 2. Skilled practitioners would realize that these syntheses could be modified to provide other compound of formula I, wherein W is N.

Compounds of formula I, wherein W is C, may be prepared by standard synthetic methods, including the methods of Examples 1 and 2. Reaction of an appropriate oxindole in the presence of a compound of formula $R_8C(O)OCH_2CH_3$ and a base, such as sodium ethoxide, in an appropriate solvent, such as ethanol would provide a substituted oxindole. Such a substituted oxindole could be subsequently reacted to form compounds of formula I, wherein W is C and $R_8$ is $R_7$ by, for example, the methods described in Examples 1 and 2.

Compounds of formula II, wherein Z is C may be prepared by standard synthetic methods. For example, compounds of formula I, wherein Z is C may be prepared from an oxindole compound, such as compound B in Example 1. Reaction of an oxindole compound in the presence of ammonia, a reagent such as phosgene, an appropriate base, and an appropriate solvent would provide a compound that could be subsequently reacted to form compounds of formula I, wherein Z is C.

Compounds of formula II, wherein Z is N may be prepared as described in Example 3.

According to another embodiment of the invention, the activity of the JNK inhibitors of this invention may be assayed in vitro, in vivo or in a cell line. In vitro assays include assays that determine inhibition of either the kinase activity or ATPase activity of activated JNK. For example, see Examples 3-5. Alternate in vitro assays quantitate the ability of the inhibitor to bind to JNK and may be measured either by radiolabelling the inhibitor prior to binding, isolating the inhibitor/JNK complex and determining the amount of radiolabel bound, or by running a competition experiment where new inhibitors are incubated with JNK bound to known radioligands. One may use any type or isoform of JNK, depending upon which JNK type or isoform is to be inhibited.

The JNK inhibitors or pharmaceutical salts thereof may be formulated into pharmaceutical compositions for administration to animals or humans. These pharmaceutical compositions, which comprise an amount of JNK inhibitor effective to treat or prevent a JNK-mediated condition and a pharmaceutically acceptable carrier, are another embodiment of the present invention.

The term "JNK-mediated condition", as used herein means any disease or other deleterious condition in which JNK is known to play a role. Such conditions include, without limitation, inflammatory diseases, autoimmune diseases, destructive bone disorders, proliferative disorders, cancer, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

Inflammatory diseases which may be treated or prevented by the compounds of this invention include, but are not limited to, acute pancreatitis, chronic pancreatitis, asthma, allergies, and adult respiratory distress syndrome.

Autoimmune diseases which may be treated or prevented by the compounds of this invention include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented by the compounds of this invention include, but are not limited to, osteoporosis, osteoarthritis and multiple myeloma-related bone disorder.

Proliferative diseases which may be treated or prevented by the compounds of this invention include, but are not limited to, acute myelogenous leukemia, chronic myelogenous leukemia, metastatic melanoma, Kaposi's sarcoma, multiple myeloma and HTLV-1 mediated tumorigenesis.

Angiogenic disorders which may be treated or prevented by the compounds of this invention include solid tumors, ocular neovasculization, infantile haemangiomas. Infectious diseases which may be treated or prevented by the compounds of this invention include, but are not limited to, sepsis, septic shock, and Shigellosis.

Viral diseases which may be treated or prevented by the compounds of this invention include, but are not limited to, acute hepatitis infection (including hepatitis A, hepatitis B and hepatitis C), HIV infection and CMV retinitis.

Neurodegenerative diseases which may be treated or prevented by the compounds of this invention include, but are not limited to, Alzheimer's disease, Parkinson's disease, amyotrophic lateral sclerosis (ALS), epilepsy, seizures, Huntington's disease, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity.

"JNK-mediated conditions" also include ischemia/reperfusion in stroke, heart attacks, myocardial ischemia, organ hypoxia, vascular hyperplasia, cardiac hypertrophy, hepatic ischemia, liver disease, congestive heart failure, pathologic immune responses such as that caused by T cell activation and thrombin-induced platelet aggregation.

In addition, JNK inhibitors of the instant invention may be capable of inhibiting the expression of inducible pro-inflammatory proteins. Therefore, other "JNK-mediated conditions" which may be treated by the compounds of this invention include edema, analgesia, fever and pain, such as neuromuscular pain, headache, cancer pain, dental pain and arthritis pain.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium and potassium), alkaline earth metal (e.g., magnesium), ammonium and N—(C1-4 alkyl)4+ salts. This invention also envisions the quaternization of any basic nitrogen-containing groups of the compounds disclosed herein. Water or oil-soluble or dispersible products may be obtained by such quaternization.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of JNK inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a JNK-mediated condition comprising the step of administering to a patient one of the above-described pharmaceutical compositions. The term "patient", as used herein, means an animal, preferably a human.

Preferably, that method is used to treat or prevent a condition selected from inflammatory diseases, autoimmune diseases, destructive bone disorders, proliferative disorders, infectious diseases, degenerative diseases, neurodegenerative diseases, allergies, reperfusion/ischemia in stroke, heart attacks, angiogenic disorders, organ hypoxia, vascular hyperplasia, cardiac hypertrophy, and thrombin-induced platelet aggregation, or any specific disease or disorder described above.

Depending upon the particular JNK-mediated condition to be treated or prevented, additional drugs, which are normally administered to treat or prevent that condition, may be administered together with the inhibitors of this invention. For example, chemotherapeutic agents or other anti-proliferative agents may be combined with the JNK inhibitors of this invention to treat proliferative diseases.

Those additional agents may be administered separately, as part of a multiple dosage regimen, from the JNK inhibitor-containing composition. Alternatively, those agents may be part of a single dosage form, mixed together with the JNK inhibitor in a single composition.

In order that the invention described herein may be more fully understood, the following examples are set forth. It should be understood that these examples are for illustrative purposes only and are not to be construed as limiting this invention in any manner.

EXAMPLE 1

Synthesis of JNK Inhibitor Compound 152

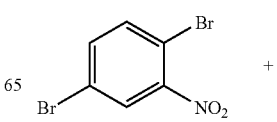

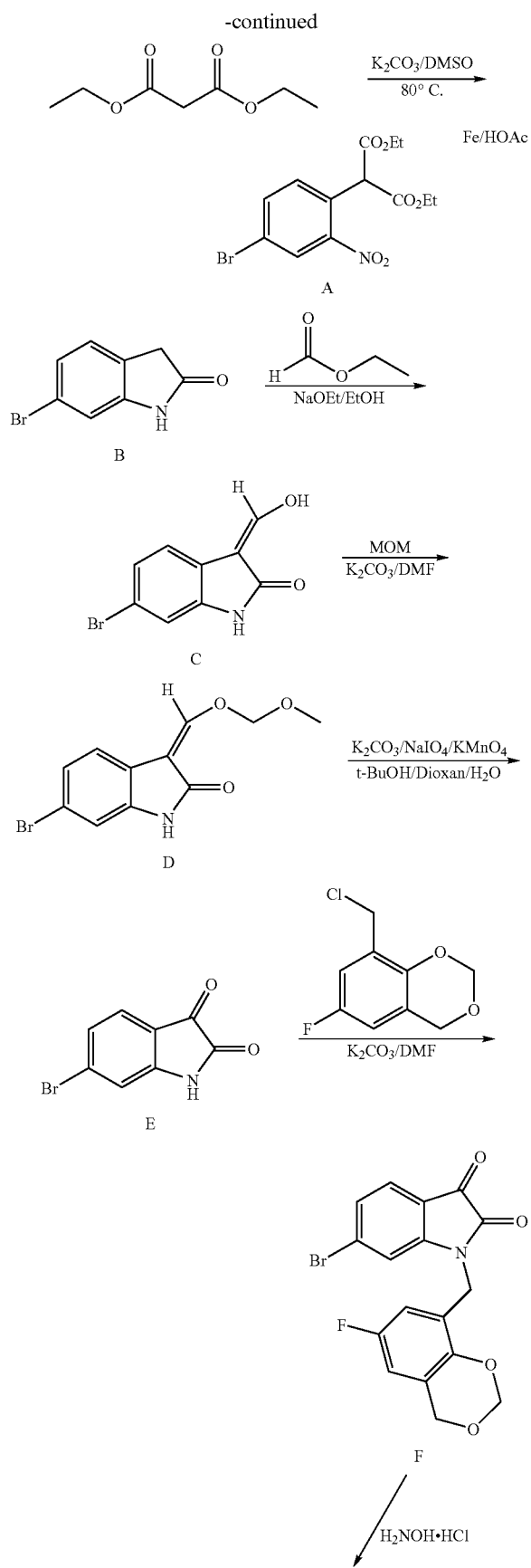

One equivalent of 2-nitro-4-bromobenzenbromide, 1.1 equivalents of diethyl malonate and 2.2 equivalents of sodium hydroxide was suspended in dimethyl sulfoxide (DMSO) and stirred at 80° C. for 24 hours (h). Thin layer chromatography (TLC) was use to indicate that the reaction was complete. The reaction mixture was then cooled to room temperature, acidified with 2N HCl, then extracted with ethyl acetate. The organic phase was washed with saturated NaCl 3 times and dried with $MgSO_4$. The solvent was removed under reduced pressure. Compound A was purified by chromatography. The yield was 78%.

One equivalent of compound A and 3 equivalents of Fe were refluxed in acetic acid for 3 h, then the reaction mixture was cooled to room temperature. Saturated NaCl and ethyl acetate was added to the reaction mixture, the organic phase was washed with saturated NaCl 3 times, dried with $MgSO_4$, and the solvent was removed under reduced pressure. Compound B was purified by chromatography. The yield was 90%.

To one equivalent of compound B, 1.4 equivalents of sodium ethoxide in ethyl alcohol was added at room temperature. The reaction mixture was stirred at 60° C. for 1 h, then 3.7 equivalents of ethylformate was added to the mixture. The mixture was stirred at 60° C. for 30 minutes, during which time a large amount of precipitate was formed. TLC indicated that the reaction was complete. The reaction mixture was cooled to room temperature. 1N HCl was added to the reaction mixture. The reaction mixture was then filtered to yield a filtration cake, which was compound C. The yield was great than 95%.

To one equivalent of compound C, 1.2 equivalents of a $K_2CO_3$/DMF suspension was added. 1.2 equivalents of methoxy-O-methyl chloride (MOMCl) was added at room temperature slowly until TLC indicated that there was no more compound C present. Saturated NaCl and ethyl acetate was added to the reaction mixture. The organic phase was washed with saturated NaCl 3 times and then was dried with $MgSO_4$. The solvent was removed under reduced pressure. Compound D was purified by chromatography. The yield was 80%.

One equivalent of Compound D was dissolved in a 4 to 1 ratio of tert-butanol (t-BuOH)/dioxane solution. Three equivalents of a saturated aqueous $K_2CO_3$ solution was added to the reaction mixture, followed by 16 equivalents of a $NaIO_4$ saturated solution and 0.25 equivalents of a $KMnO_4$ saturated solution. The reaction mixture was stirred at room temperature for 1 h. TLC indicated the reaction was completed. Ethyl acetate and H₂O was added to the reaction mixture, the organic phase was washed with saturated NaCl 3 times, dried with MgSO₄ and the solvent was removed under reduced pressure. The residue was compound E. The yield was 88%.

One equivalent of Compound E was mixed with 1.2 equivalents of 8-(chloromethyl)-6-fluorobenzo-1,3-dioxan and 1.2 equivalents of K₂CO₃ in a DMF suspension and stirred at room temperature overnight. TLC indicated the reaction was complete. Saturated NaCl and ethyl acetate was added to the reaction mixture, the organic phase was washed with saturated NaCl 3 times, dried with MgSO₄, and the solvent was removed under reduced pressure. Compound F was purified by chromatography. The yield was 80%.

One equivalent of Compound F, 1.3 equivalents of hydroxylamine hydrochloride and 2.6 equivalents of K₂CO₃ in a DMF suspension were stirred together at room temperature overnight. TLC indicated the reaction was complete. Saturated NaCl and ethyl acetate was added to the reaction mixture, the organic phase was washed with saturated NaCl 3 times, dried with MgSO₄, and the solvent was removed under reduced pressure. Compound 152 was purified by chromatography.

EXAMPLE 2

Synthesis of JNK Inhibitor Compound 153

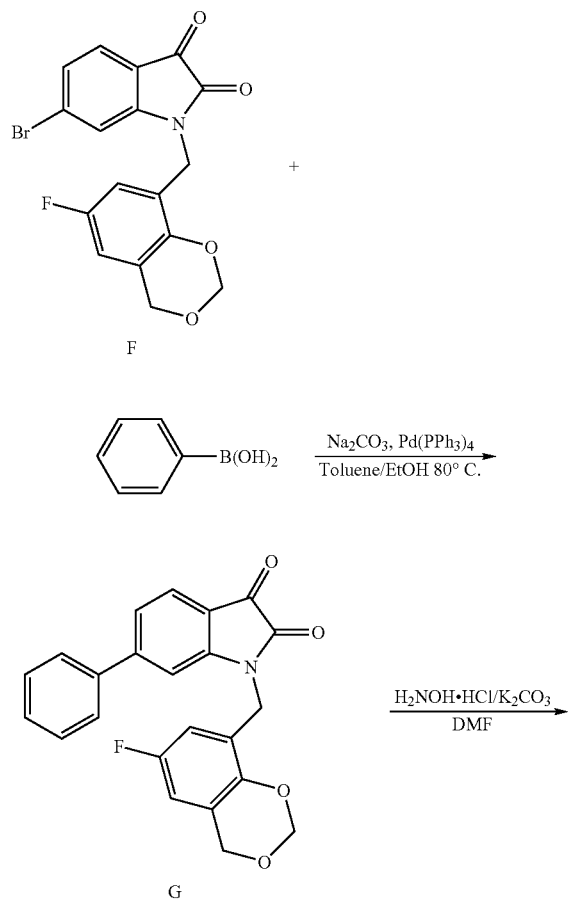

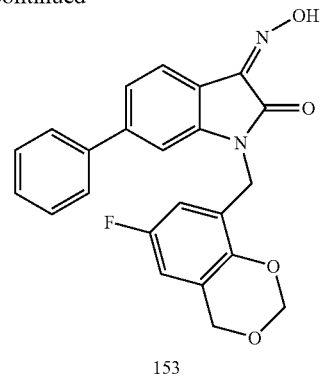

153

One equivalent of Compound F (prepared as in Example 1), 1.2 eq of phenyl boronic acid, Na₂CO₃, and a catalytical amount of tetrakis triphenylphosphine palladium toluene was suspended in water and stirred at 80° C. overnight. Saturated NaCl and ethyl acetate was added to the reaction mixture, the organic phase was dried with MgSO₄, and the solvent was removed under reduced pressure. Compound G was purified by chromatography. The yield was 64%.

One equivalent of Compound G, 1.3 equivalents of hydroxylamine hydrochloride and 2.6 equivalents of K₂CO₃ in a DMF suspension were stirred together at room temperature overnight. TLC indicated the reaction was complete. Saturated NaCl and ethyl acetate was added to the reaction mixture, the organic phase was washed with saturated NaCl 3 times, dried with MgSO₄, and the solvent was removed under reduced pressure. Compound 153 was purified by chromatography.

EXAMPLE 3

Solid Phase Synthesis of JNK Inhibitors of Formula II, wherein Z is N

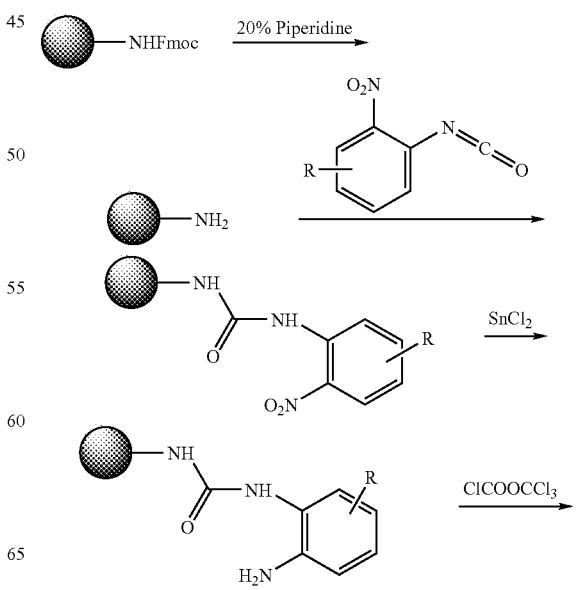

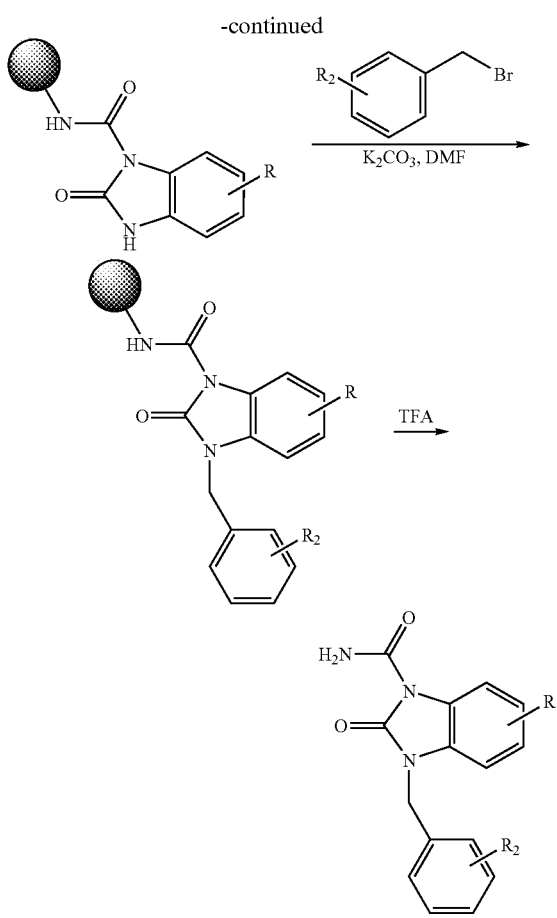

Compound of formula II, wherein Z is N, may be prepared as shown in the above synthetic scheme. The synthetic scheme may be modified to provide other compounds of formula II, wherein Z is N.

EXAMPLE 4

Cloning, Expression and Purification of JNK3 Protein

A BLAST search of the EST database using the published JNK3α1 cDNA as a query identified an EST clone (#632588) that contained the entire coding sequence for human JNK3α1. Polymerase chain reactions (PCR) using pfu polymerase (Strategene) were used to introduce restriction sites into the cDNA for cloning into the pET-15B expression vector at the NcoI and BamHI sites. The protein was expressed in E. coli. Due to the poor solubility of the expressed full-length protein (Met 1-Gln 422), an N-terminally truncated protein starting at Ser residue at position 40 (Ser 40) was produced. This truncation corresponds to Ser 2 of JNK1 and JNK2 proteins, and is preceded by a methionine (initiation) and a glycine residue. The glycine residue was added in order to introduce an NcoI site for cloning into the expression vector. In addition, systematic C-terminal truncations were performed by PCR to identify a construct that give rise to diffraction-quality crystals. One such construct encodes amino acid residues Ser40-Glu402 of JNK3α1 and is preceded by Met and Gly residues.

The construct was prepared by PCR using deoxyoligonucleotides 5' GCTCTAGAGCTCC ATGGGCAGCAAAAGCAAAGTTGACAA 3' (forward primer with initiation codon underlined) and 5' TAGCG-GATCCTCATTCTGAATTCATTACTTCCTTGTA 3' (reverse primer with stop codon underlined) as primers and was confirmed by DNA sequencing. Control experiments indicated that the truncated JNK3 protein had an equivalent kinase activity towards myelin basic protein when activated with an upstream kinase MKK7 in vitro.

E.coli strain BL21 (DE3) (Novagen) was transformed with the JNK3 expression construct and grown at 30° C. in LB supplemented with 100 μg/ml carbenicillin in shaker flasks until the cells were in log phase ($OD_{600}$~0.8). Isopropylthio-β-D-galactosidase (IPTG) was added to a final concentration of 0.8 mM and the cells were harvested 2 hours later by centrifugation.

E. coli cell paste containing JNK3 was resuspended in 10 volumes/g lysis buffer (50 mM HEPES, pH 7.2, containing 10% glycerol (v/v), 100 mM NaCl, 2 mM DTT, 0.1 mM PMSF, 2 μg/ml Pepstatin, 1 μg/ml each of E-64 and Leupeptin). Cells were lysed on ice using a microfluidizer and centrifuged at 100,000×g for 30 min at 4° C. The 100,000×g supernatant was diluted 1:5 with Buffer A (20 mM HEPES, pH 7.0, 10% glycerol (v/v), 2 mM DTT) and purified by SP-Sepharose (Pharmacia) cation-exchange chromatography (column dimensions: 2.6×20 cm) at 4° C. The resin was washed with 5 column volumes of Buffer A, followed by 5 column volumes of Buffer A containing 50 mM NaCl. Bound JNK3 was eluted with a 7.5 column volume linear-gradient of 50-300 mM NaCl. JNK3 eluted between 150-200 mM NaCl.

EXAMPLE 5

Activation of JNK3

5 mg of JNK3 was diluted to 0.5 mg/ml in 50 mM HEPES buffer, pH 7.5, containing 100 mM NaCl, 5 mM DTT, 20 mM $MgCl_2$ and 1 mM ATP. GST-MKK7(DD) was added at a molar ratio of 1:2.5 GST-MKK7:JNK3. After incubation for 30 minutes at 25° C., the reaction mixture was concentrated 5-fold by ultrafiltration in a Centriprep-30 (Amicon, Beverly, Mass.), diluted to 10 ml and an additional 1 mM ATP added. This procedure was repeated three times to remove ADP and replenish ATP. The final addition of ATP was 5 mM and the mixture incubated overnight at 4° C.

The activated JNK3/GST-MKK7(DD) reaction mixture was exchanged into 50 mM HEPES buffer, pH 7.5, containing 5 mM DTT and 5% glycerol (w/v) by dialysis or ultrafiltration. The reaction mixture was adjusted to 1.1 M potassium phosphate, pH 7.5, and purified by hydrophobic interaction chromatography (at 25° C.) using a Rainin Hydropore column. GST-MKK7 and unactivated JNK3 do not bind under these conditions such that when a 1.1 to 0.05 M potassium phosphate gradient is developed over 60 minutes at a flow rate of 1 ml/minute, doubly phosphorylated JNK3 is separated from singly phosphorylated JNK. Activated JNK3 (i.e. doubly phosphorylated JNK3) was stored at −70° C. at 0.25-1 mg/ml.

EXAMPLE 6

JNK Inhibition Assays

Compounds were assayed for the inhibition of JNK3 by a spectrophotometric coupled-enzyme assay. In this assay, a fixed concentration of activated JNK3 (10 nM) was incubated with various concentrations of a potential inhibitor dissolved in DMSO for 10 minutes at 30° C. in a buffer containing 0.1 M HEPES buffer, pH 7.5, containing 10 mM $MgCl_2$, 2.5 mM phosphoenolpyruvate, 200 μM NADH, 150 μg/mL pyruvate kinase, 50 μg/mL lactate dehydrogenase, and 200 μM EGF receptor peptide. The EGF receptor peptide has the sequence KRELVEPLTPSGEAPNQALLR, and is a phosphoryl acceptor in the JNK3-catalyzed kinase reaction. The reaction was initiated by the addition of 10 μM ATP and the assay plate is inserted into the spectrophotometer's assay plate compartment that was maintained at 30° C. The decrease of absorbance at 340 nm was monitored as a function of time. The rate data as a function of inhibitor concentration was fitted to competitive inhibition kinetic model to determine the $K_i$.

We claim:

1. A compound of the formula:

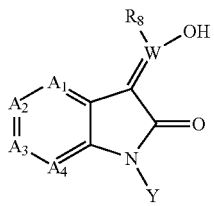

I or a pharmaceutically acceptable salt thereof; wherein
Y is selected from —$(CH_2)$-$Q_1$; —(CO)-$Q_1$; —(CO)NH-$Q_1$; —(CO)—O-$Q_1$; —$(SO_2)$-$Q_1$ or —$(SO_2)$NH-$Q_1$;
$Q_1$ is a $C_1$-$C_6$ straight chain or branched alkyl or alkenyl group; a 5-7 membered aromatic or non-aromatic heterocyclic ring; or a 9-14 membered bicyclic or tricyclic aromatic or non-aromatic carbocyclic or heterocyclic ring system, wherein said alkyl, alkenyl, ring or ring system is optionally substituted with one to four substituents, each of which is independently selected from $NH_2$, NH—R, $N(R)_2$, $NO_2$, OH, OR, $CF_3$, halo, CN, $CO_2H$, C(O)—$NH_2$, C(O)—NH—R, C(O)—$N(R)_2$, C(O)—R, SR, S(O)—R, $S(O)_2$—R, $S(O)_2$—NH—R or —R;
W is N;
$R^8$ is a lone pair of electrons;
$A_1$ is $CR^1$;
$A_2$ is $CR^2$;
$A_3$ is $CR^3$;
$A_4$ is $CR^4$;
$R^1$ is —$NHR^5$, —$OR^5$, —$SR^5$, or —$R^5$;
$R^2$, $R^3$, and $R^4$ are independently selected from —(CO)$NH_2$, —(CO)NHR, —(CO)$N(R)_2$, —$NHR^5$, —$NHCH_2R^5$, —$OR^5$, —$SR^5$, —$R^5$, —NH(CO)—$R^6$, —NH(CO)—$NHR^6$, —NH(CO)—NH(CO)$R^6$, —NH(CO)—$OR^6$, —$NH(SO_2)$—$R^6$, —$NH(SO_2)$—$NHR^6$, —C(O)OH, —C(O)OR, —(CO)-$Q_1$, —(CO)NH-$Q_1$, —(CO)NR-$Q_1$, —(CO)—O-$Q_1$, —$(SO_2)$-$Q_1$ or —$(SO_2)NH$-$Q_1$;
$R^5$ and $R^6$ are each independently selected from H; $N(R)_2$, NHOH, $NO_2$, C(O)OR or halo; a $C_1$-$C_6$ straight chain or branched alkyl, alkenyl or alkynyl group; a 5-7 membered aromatic or non-aromatic carbocyclic or heterocyclic ring; or a 9-14 membered bicyclic or tricyclic aromatic or non-aromatic carbocyclic or heterocyclic ring; wherein said alkyl, alkenyl, ring or ring system is optionally substituted with one to four substituents, each of which is independently selected from $NH_2$, NHR, NHC(O)OR, $N(R)_2$, $NO_2$, OH, OR, $CF_3$, halo, CN, $Si(R)_3$, $CO_2H$, COOR, $CONH_2$, CONHR, $CON(R)_2$, COR, SR, S(O)R, $S(O)_2R$, $S(O)_2NHR$ or R;
R is a $C_1$-$C_6$ straight chain or branched alkyl or alkenyl group, a 5-7 membered aromatic or non-aromatic carbocyclic or heterocyclic ring, or a 9-10 membered bicyclic aromatic or non-aromatic carbocyclic or heterocyclic ring system.

2. The compound of claim 1, wherein Y is —$(CH_2)$-$Q_1$ and $Q_1$ is optionally substituted benzodioxanyl.

3. The compound of claim 1, wherein $R^1$ is $R^5$.

4. The compound of claim 1, wherein $R^1$ is H, methyl, halo, optionally substituted phenyl, a monocyclic or bicyclic heterocycle, optionally substituted alkyl, alkenyl or alkynyl, or COOR.

5. The compound of claim 1, wherein $R^2$ is $R^5$, NH(CO)—$R^6$, $NH(SO_2)$—$R^6$, —$NHCH_2R^5$, CO-$Q_1$ or CONH-$Q_1$.

6. The compound of claim 1, wherein $R^2$ is H, halo, $NO_2$, $NH_2$, methyl, $OCF_3$, —$N(R)_2$, or substituted phenyl.

7. The compound of claim 1, wherein $R^3$ is $R^5$, NH(CO)—$R^6$, $NH(SO_2)$—$R^6$, or CONH-$Q_1$.

8. The compound of claim 1, wherein $R^3$ is H, halo, methyl, $CF_3$, optionally substituted phenyl, a heterocyclic ring, a bicyclic ring, $NO_2$ or $NH_2$.

9. The compound of claim 1, wherein $R^4$ is $R^5$.

10. The compound of claim 1, wherein $R^4$ is H or methyl.

11. The compound according to claim 1, wherein said compound is selected from the group consisting of:

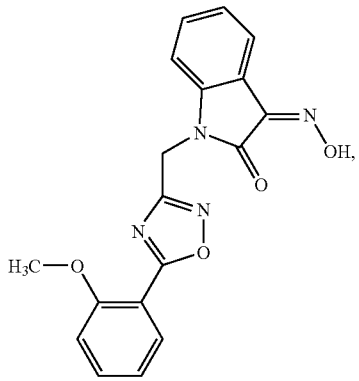

64

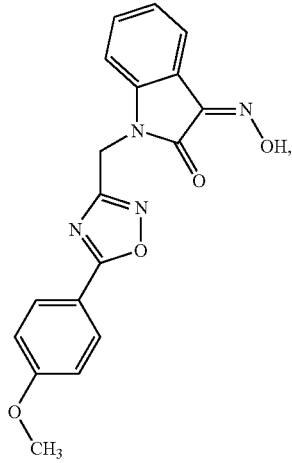

65

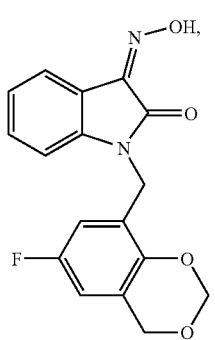
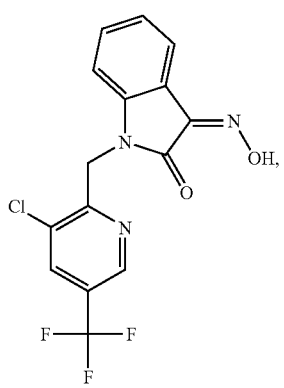
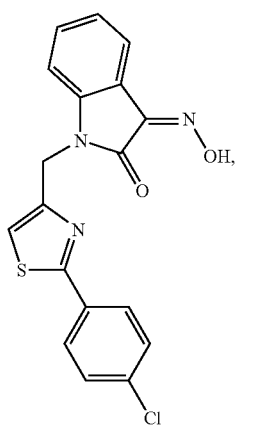
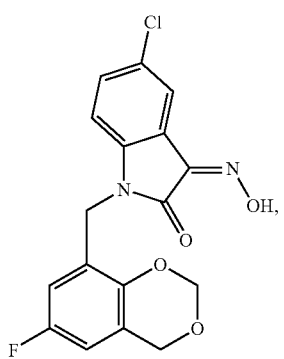
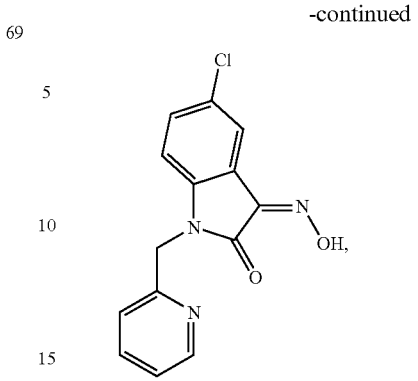
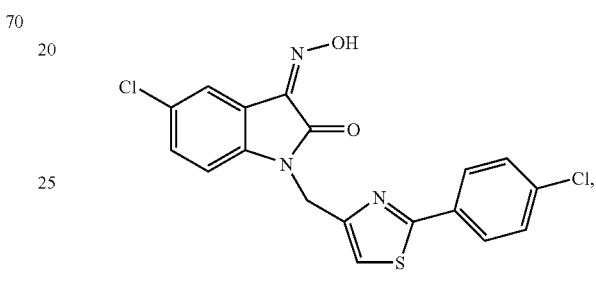
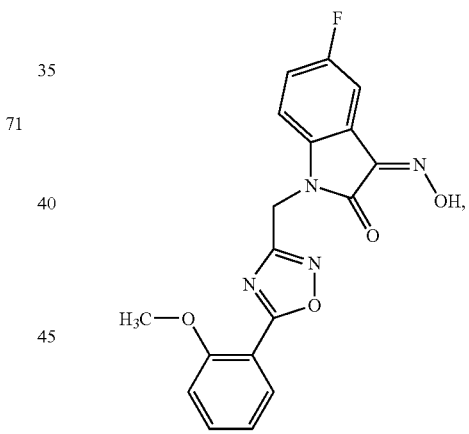
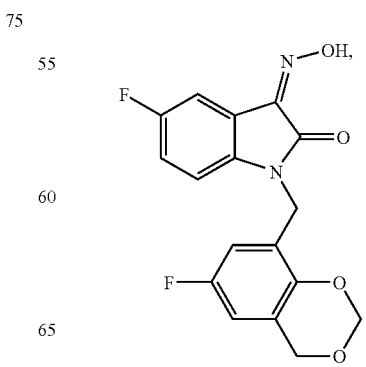

-continued
86
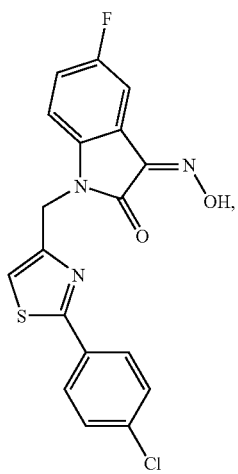
90
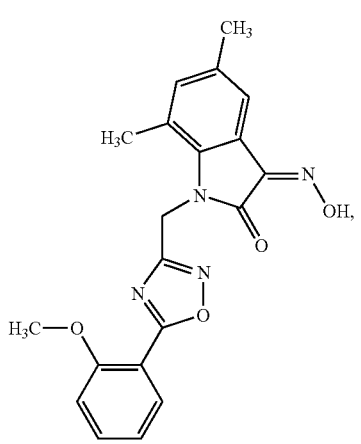
91
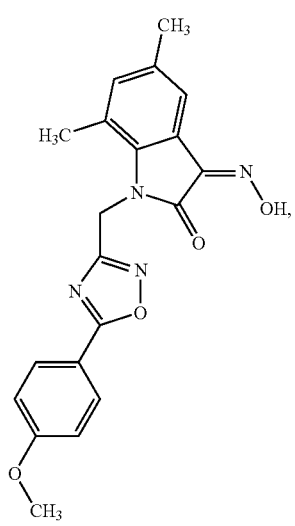
-continued
95
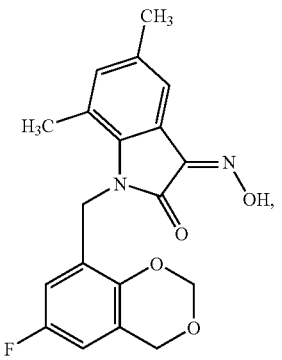
96
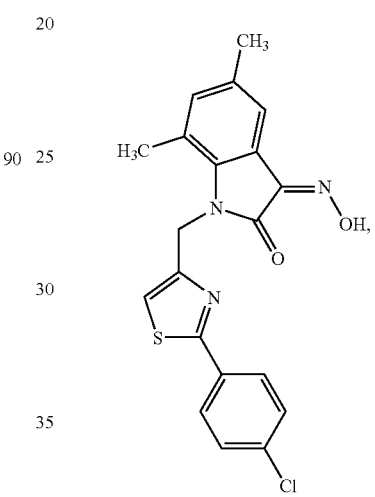
103
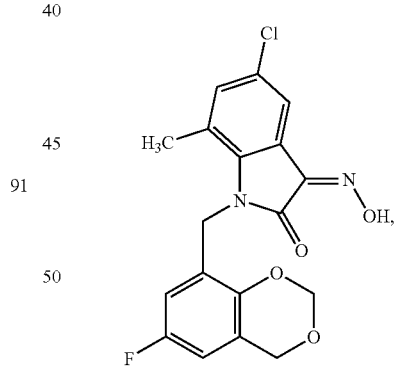
104
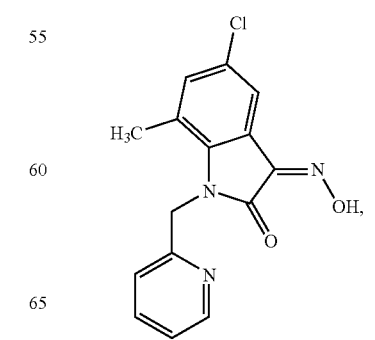

-continued
108 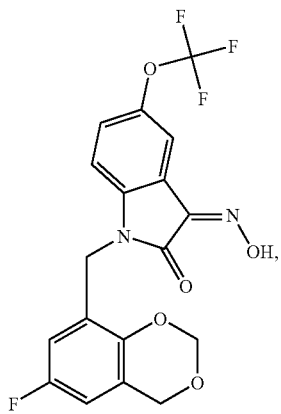
109 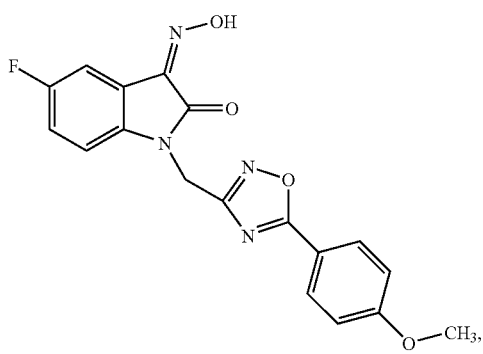
110 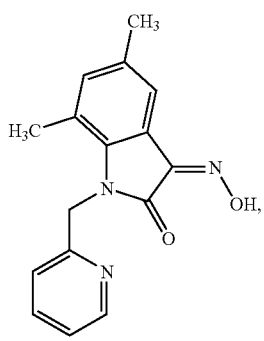
111 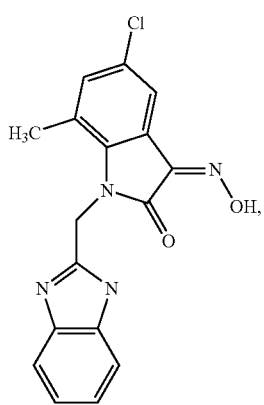
-continued
112 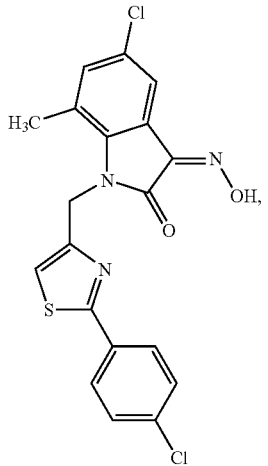
113 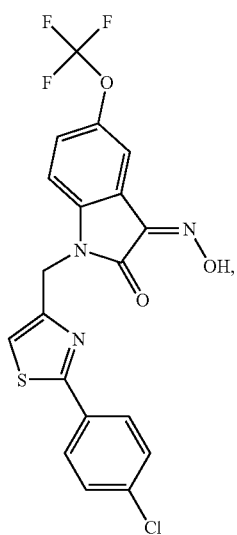
118 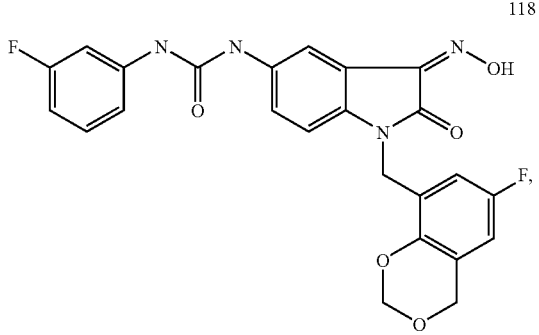

-continued
122
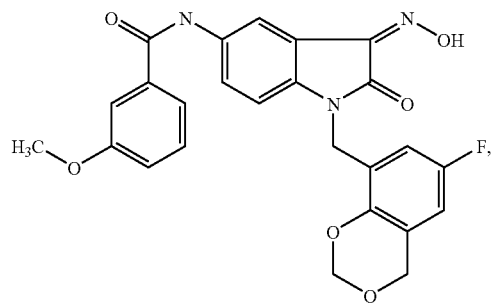
132
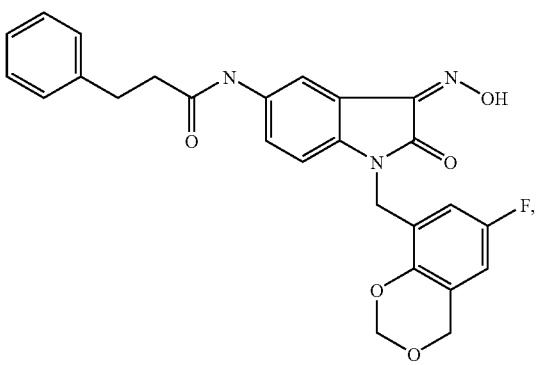
124
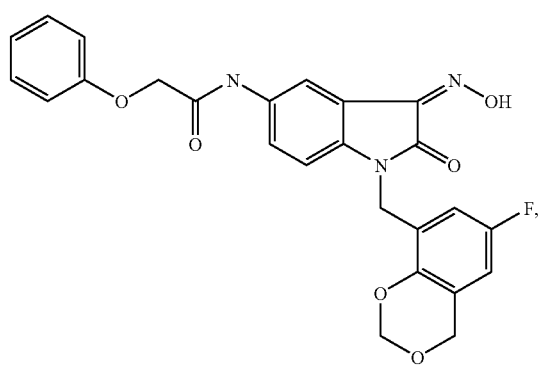
135
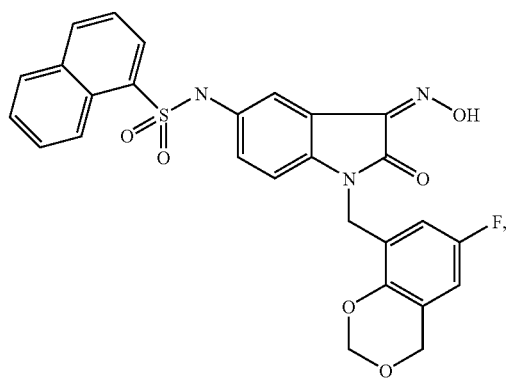
127
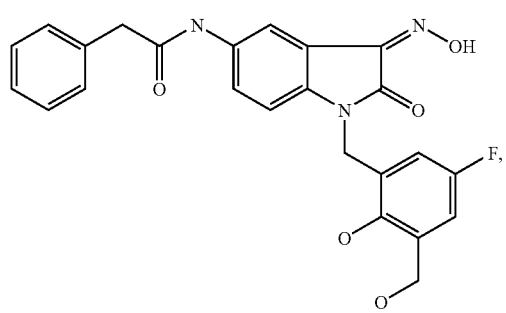
138
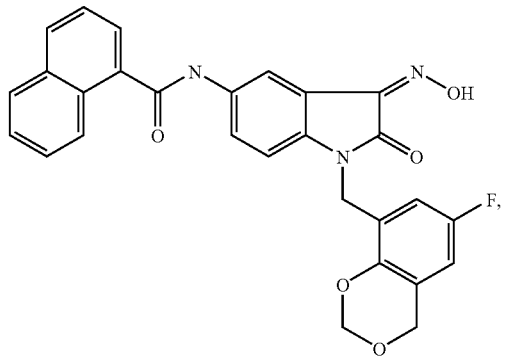
129
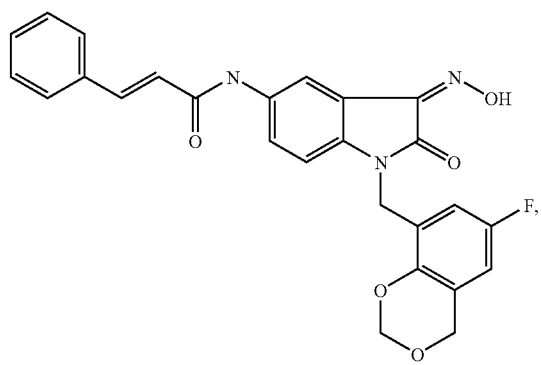
141
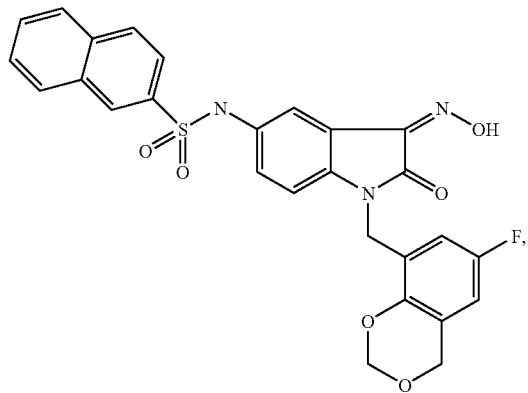

-continued
148
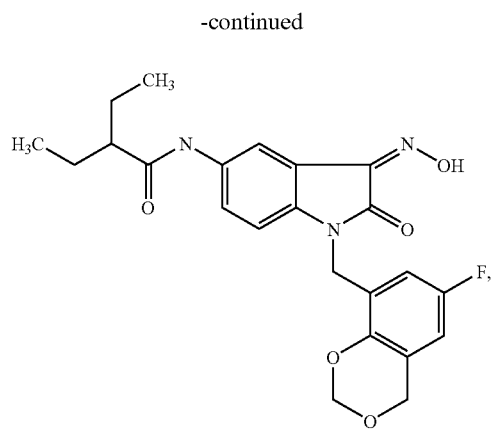
149
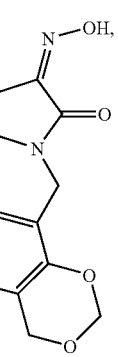
152
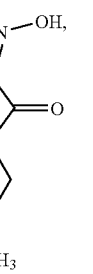
153
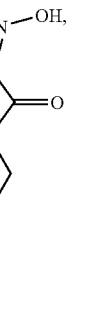
-continued
154
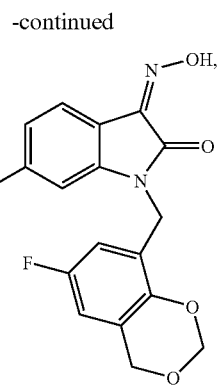
156
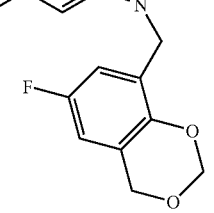
159

161 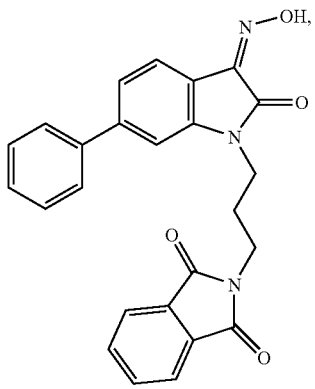
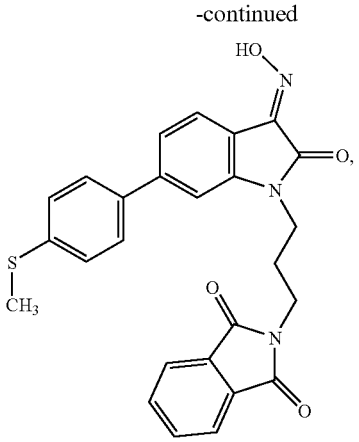 168
163 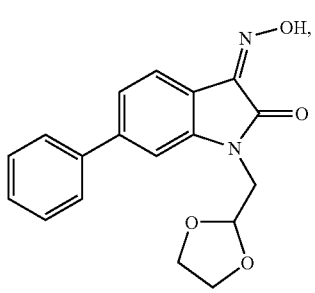
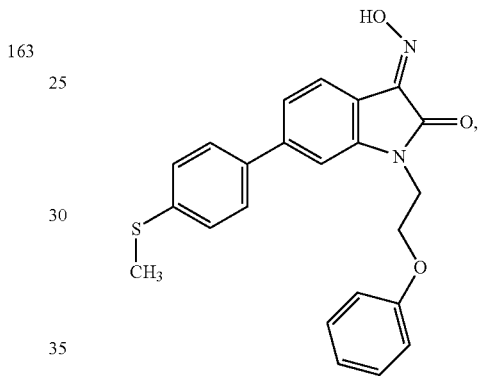 169
165 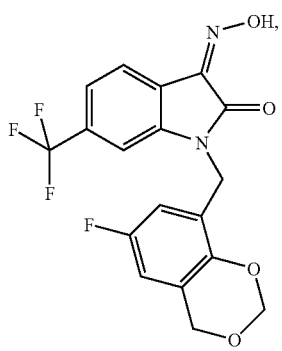
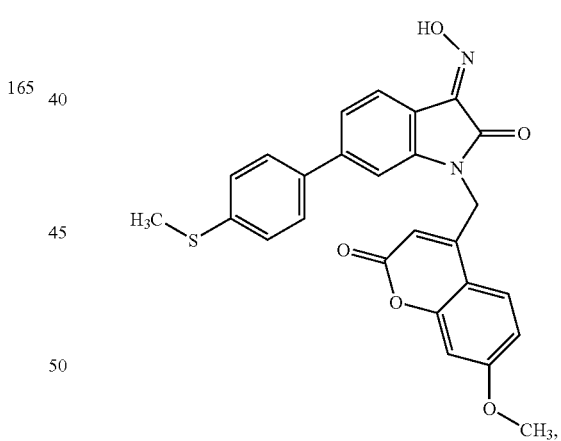 170
167 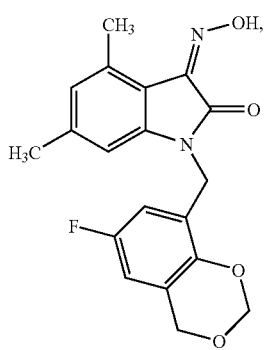
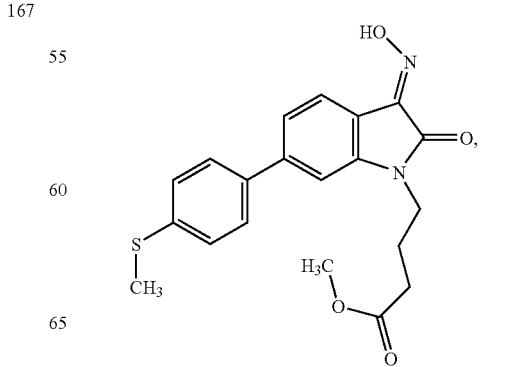 172

-continued
173 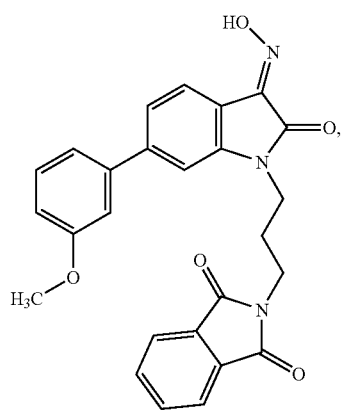
174 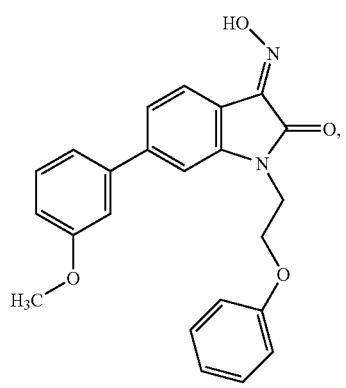
175 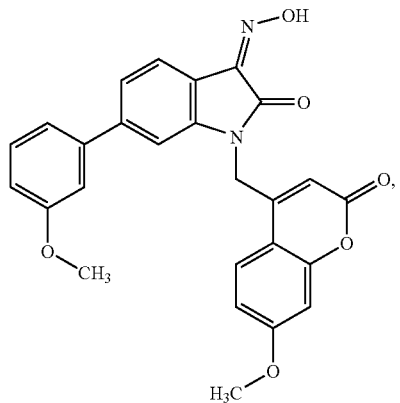
177 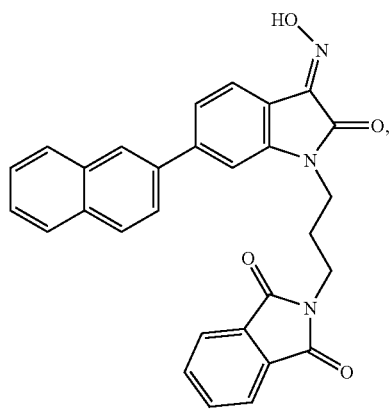
-continued
178 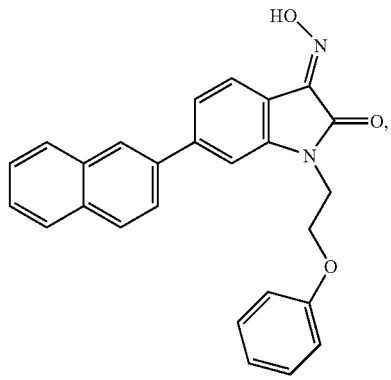
179 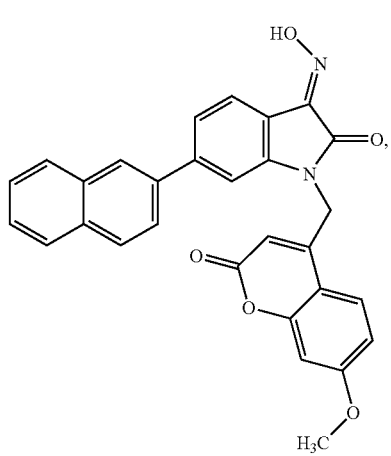
181 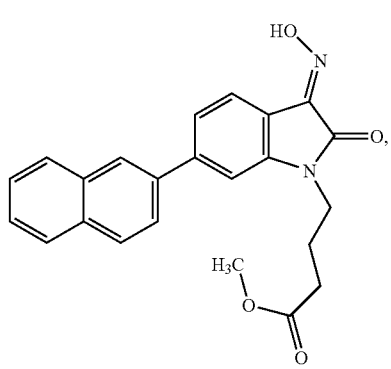
182 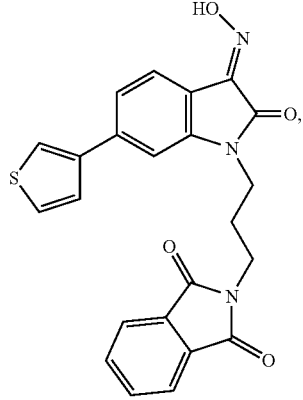

-continued
183 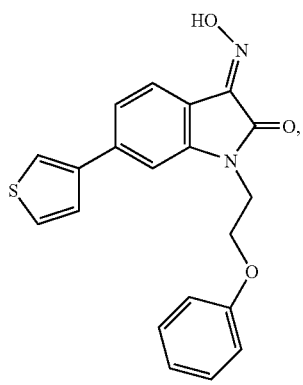
184 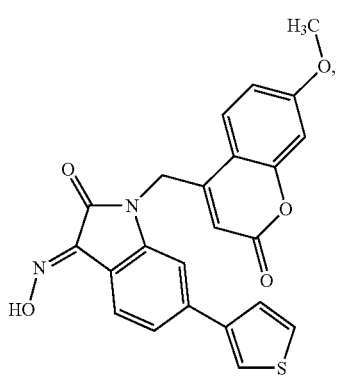
186 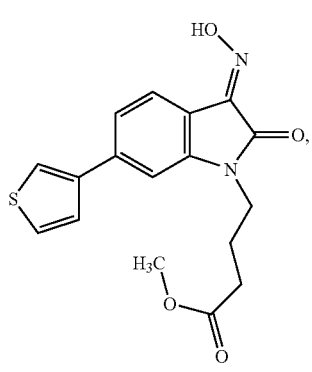
187 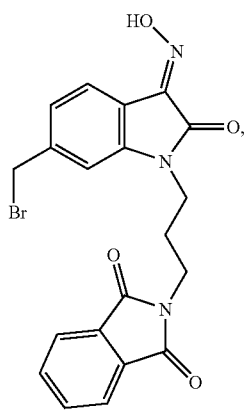
-continued
188 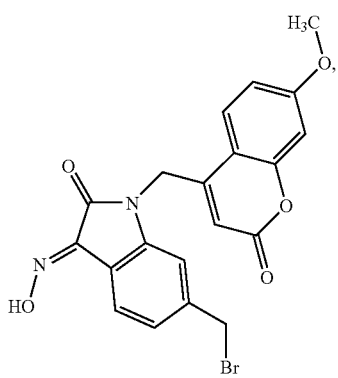
190 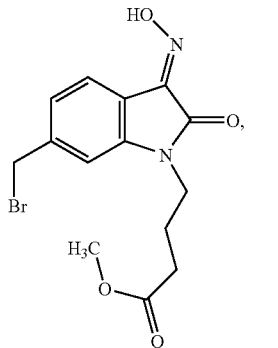
191 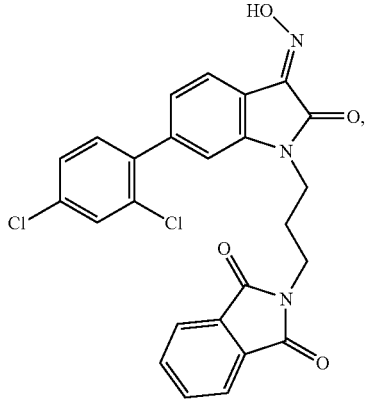
192 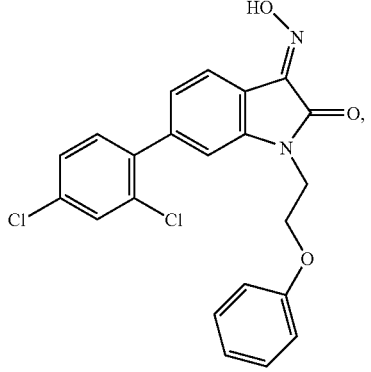

-continued
193 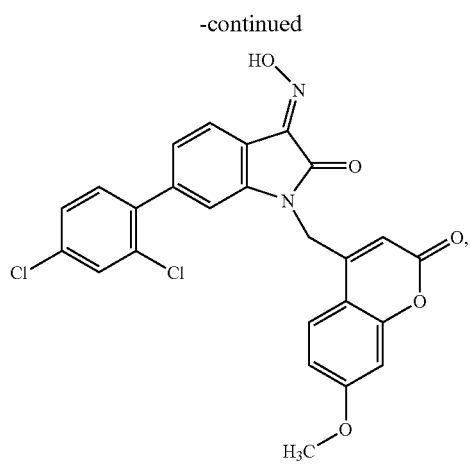
195 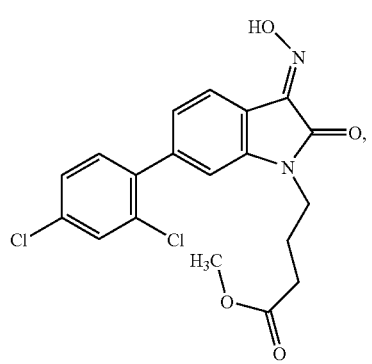
196 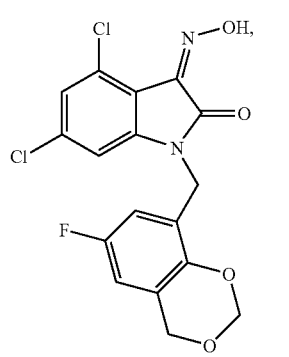
201 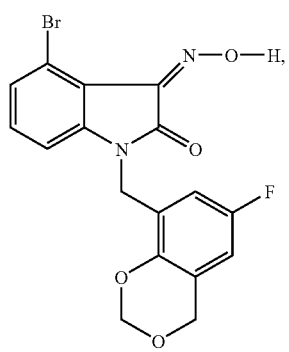
-continued
202 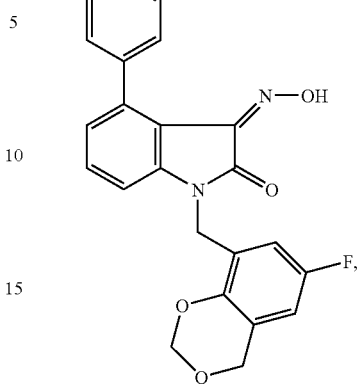
203 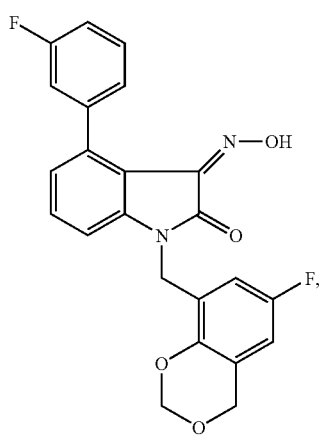
204 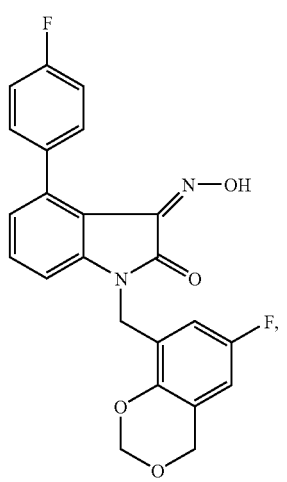

205 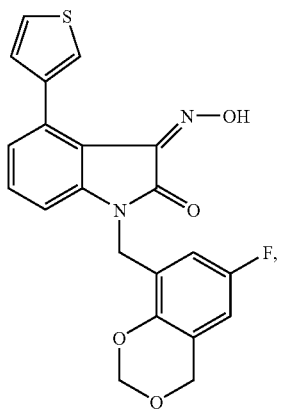
209 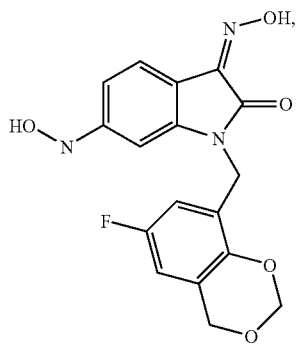
206 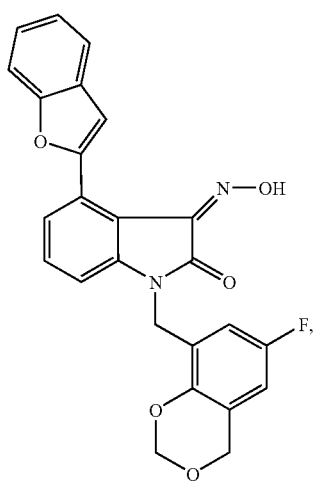
210 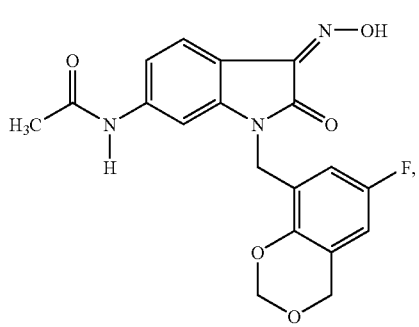
207 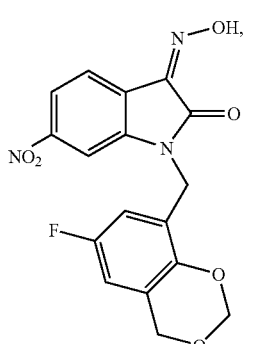
211 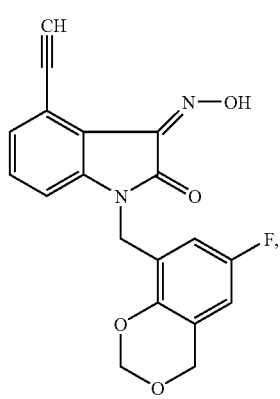
208 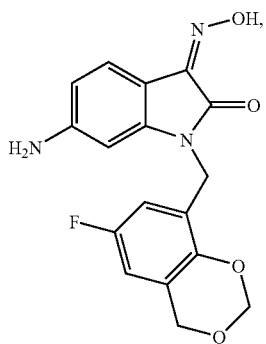
212 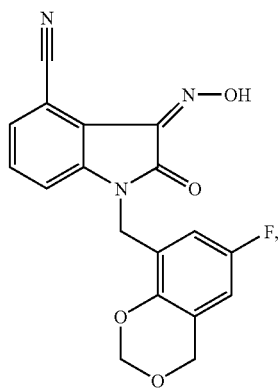

-continued
213
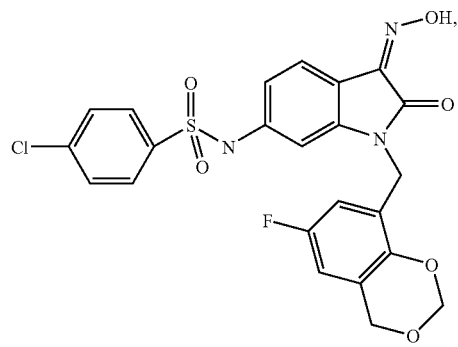
214
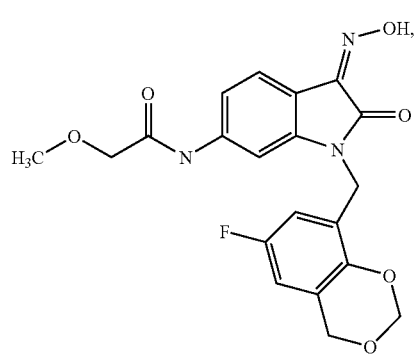
215
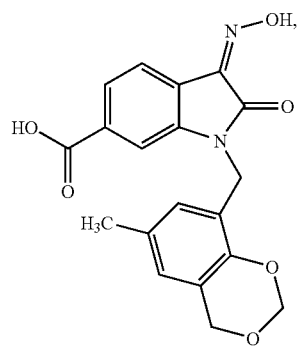
216
-continued
217
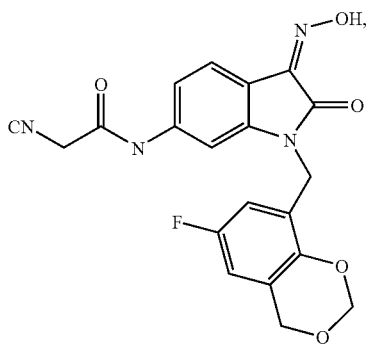
218
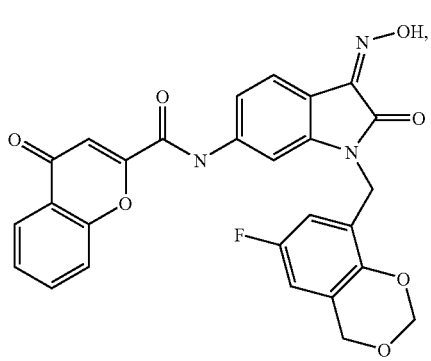
219
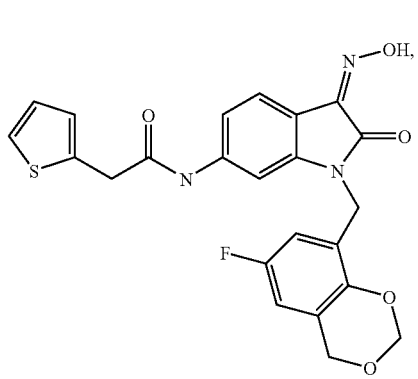
220
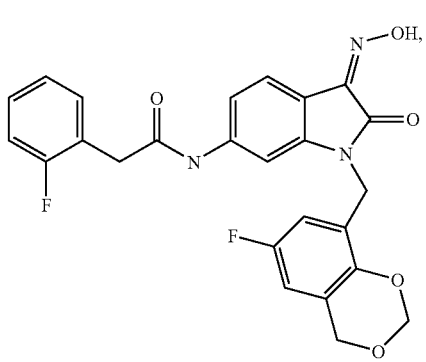

-continued
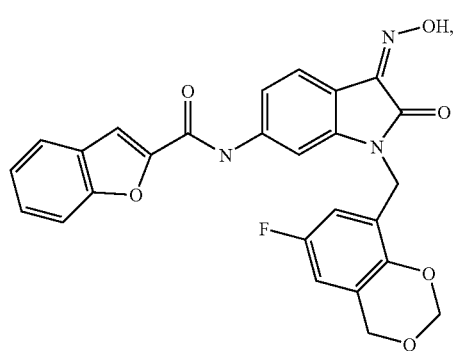
221
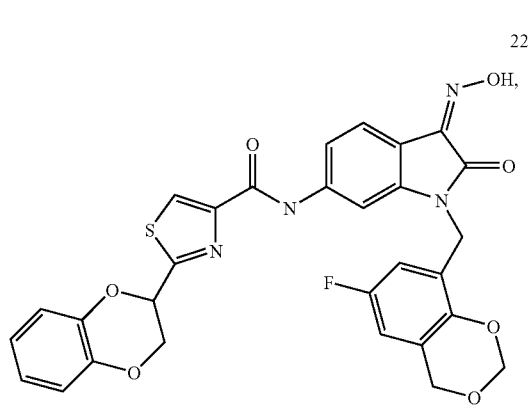
222
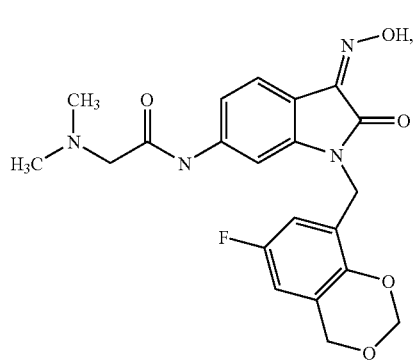
223
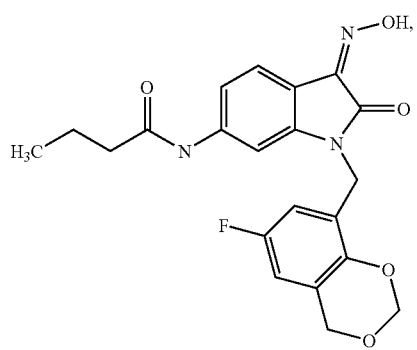
224
-continued
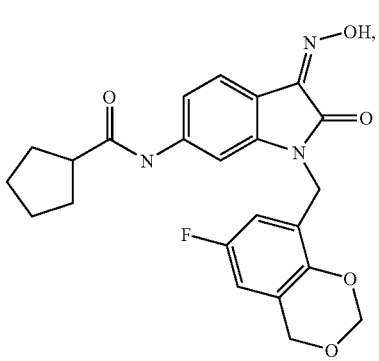
225
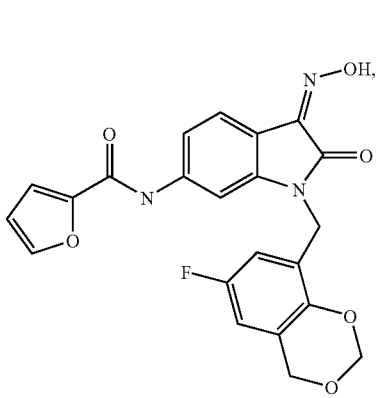
226
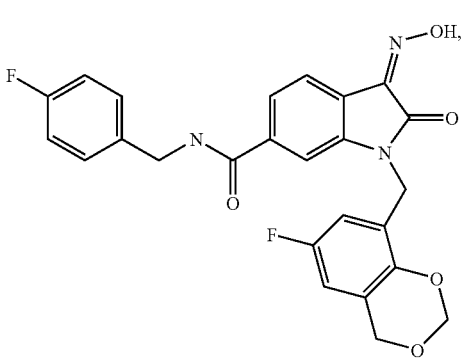
227
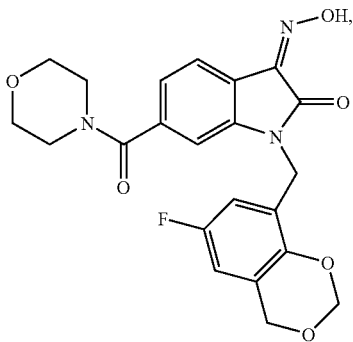
228

-continued
229
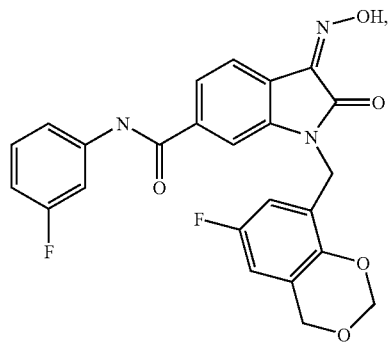
230
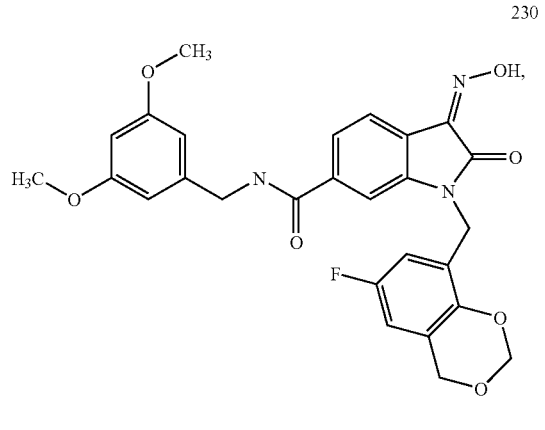
231
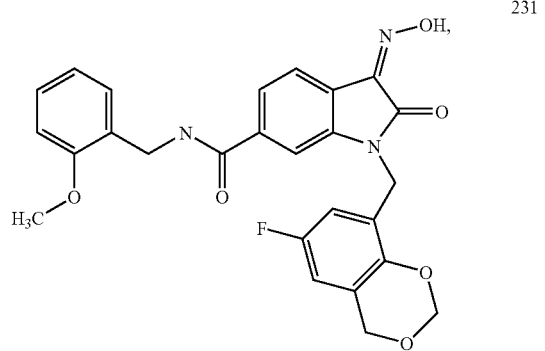
232
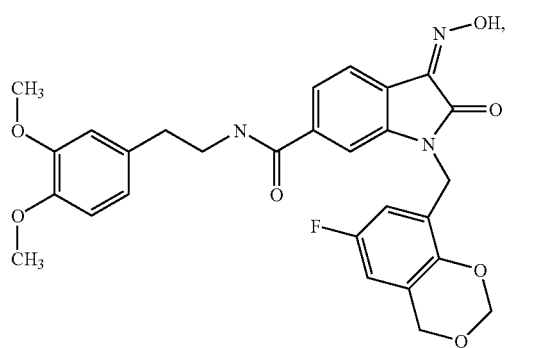
-continued
233
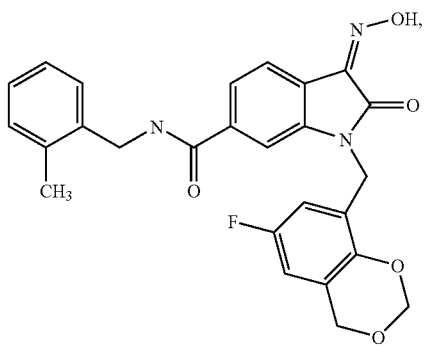
234
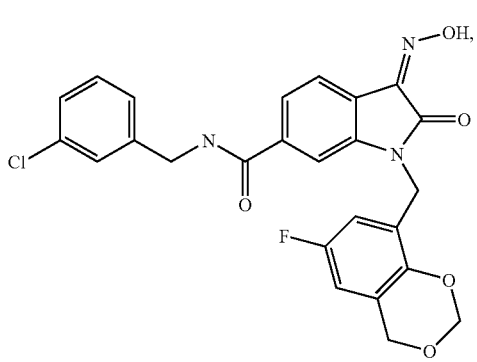
235
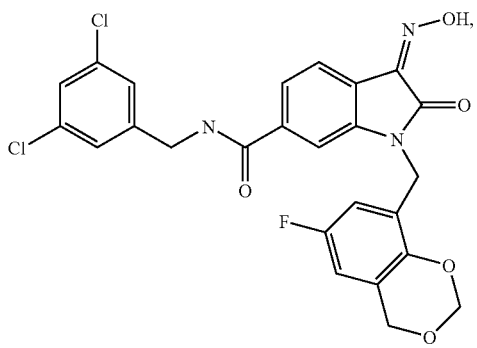
236
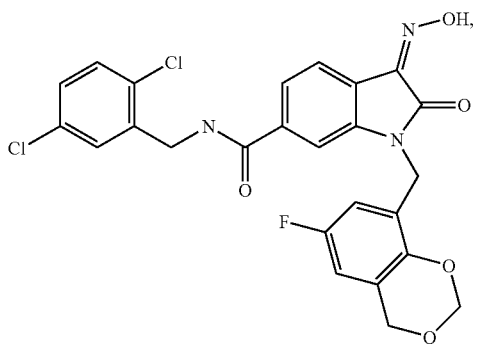

-continued
237
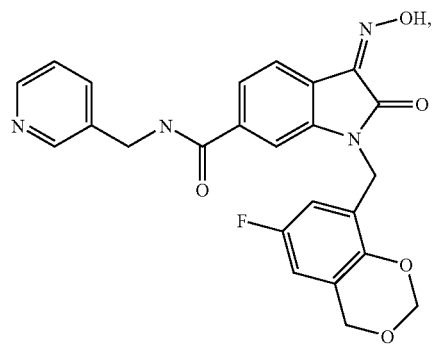
238
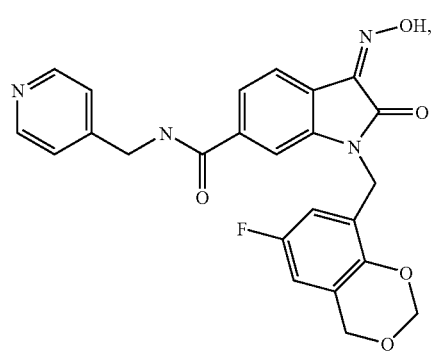
239
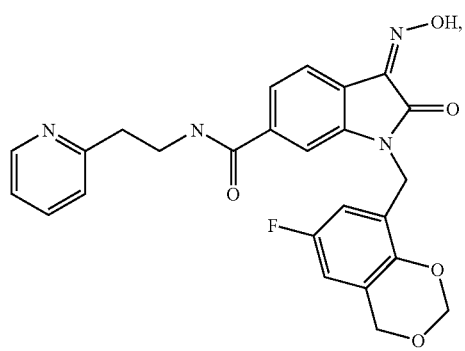
240
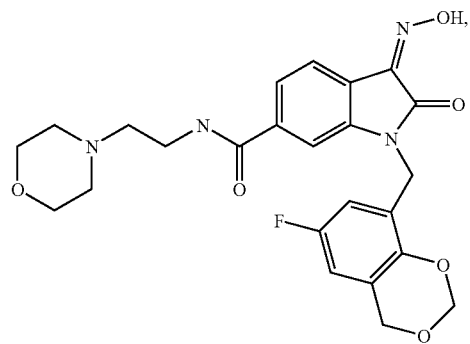
-continued
241
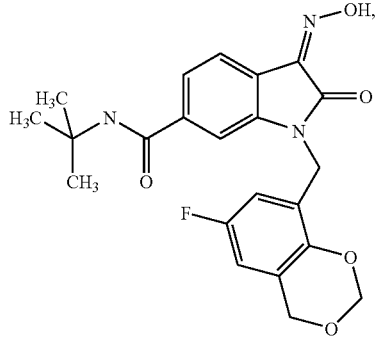
242
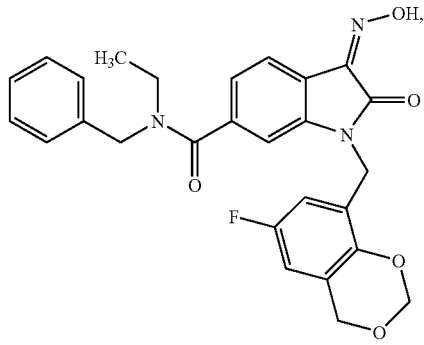
243
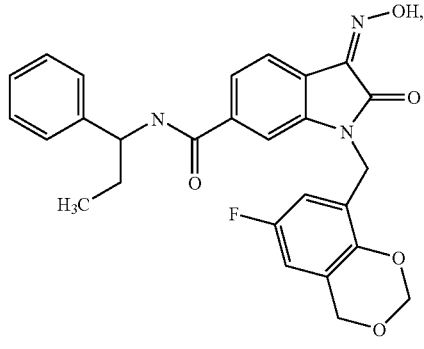
244
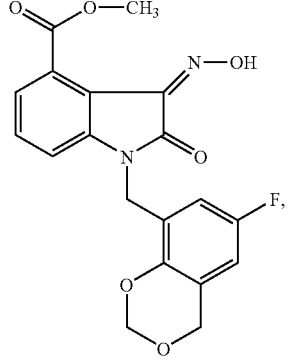

246
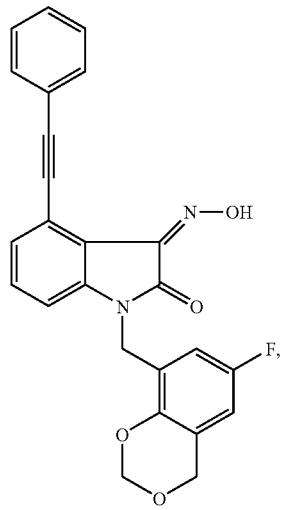
247
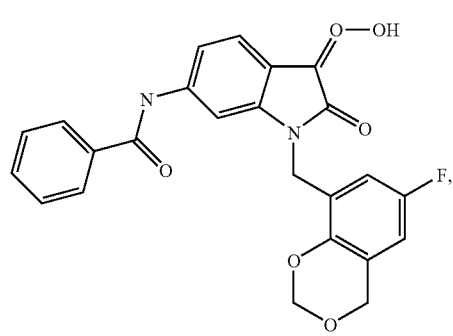
248
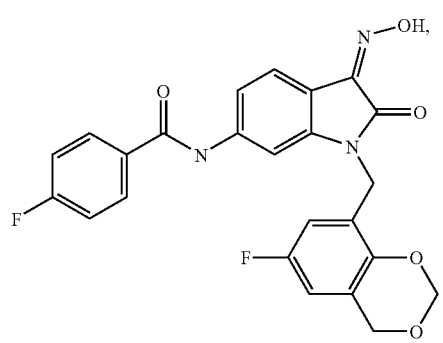
249
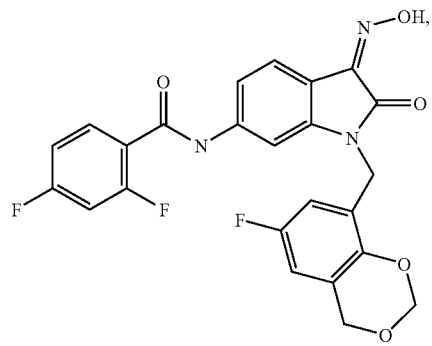
250
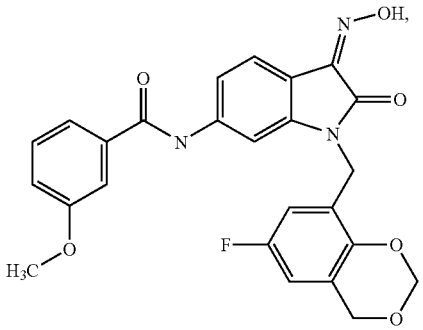
251
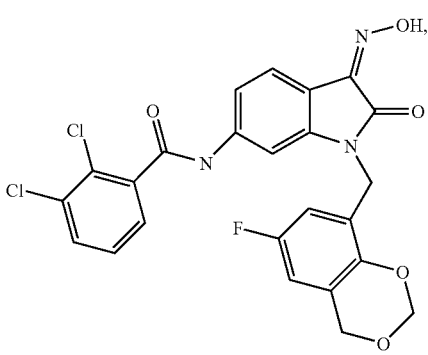
252
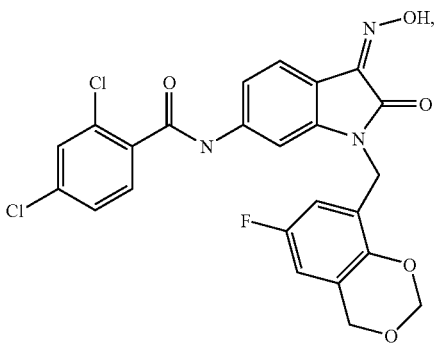
253
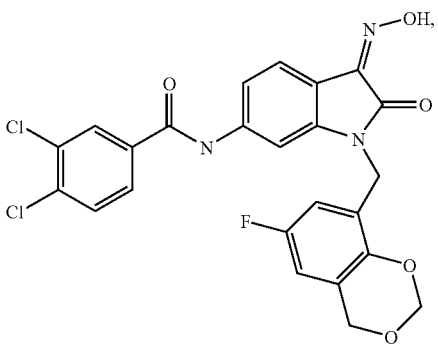

-continued
254
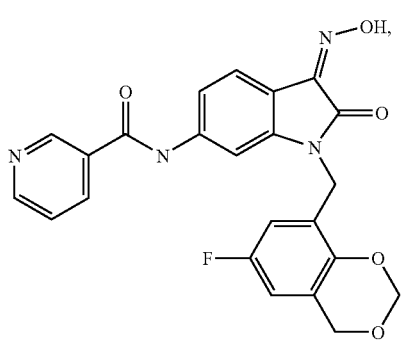
255
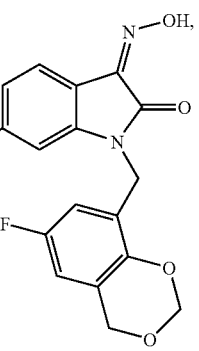
256
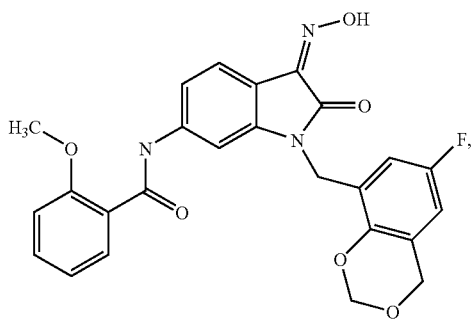
257
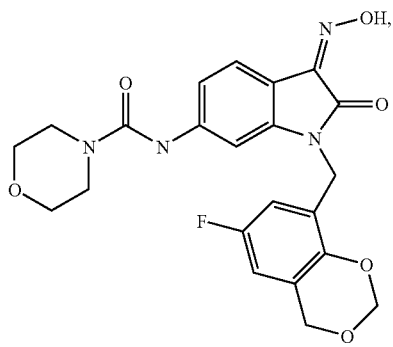
-continued
258
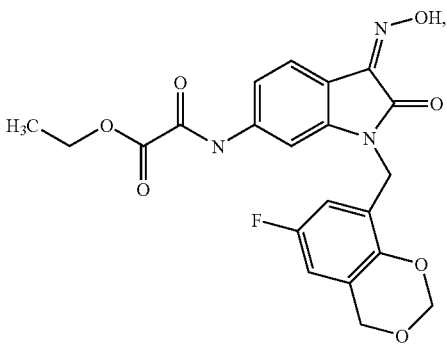
259
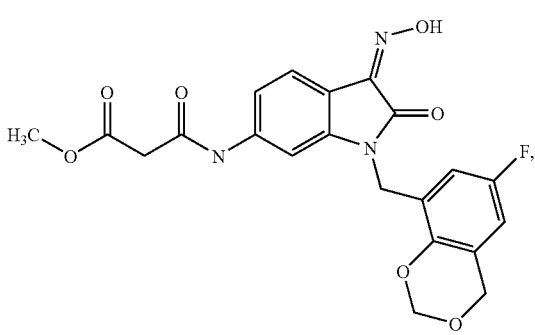
260
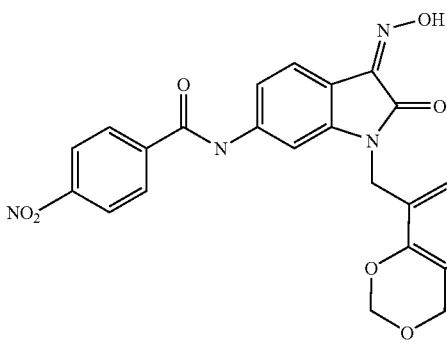
261
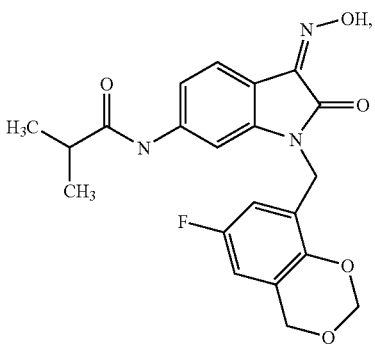

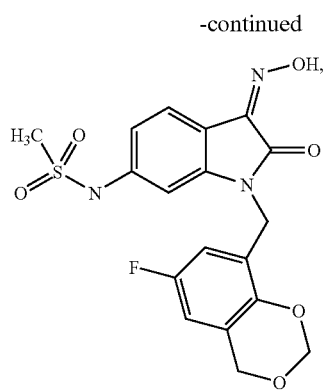
262
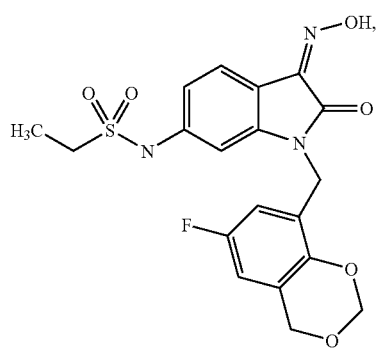
263
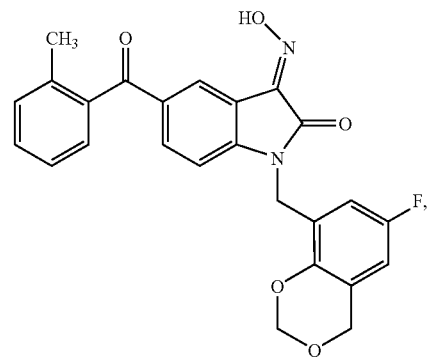
266
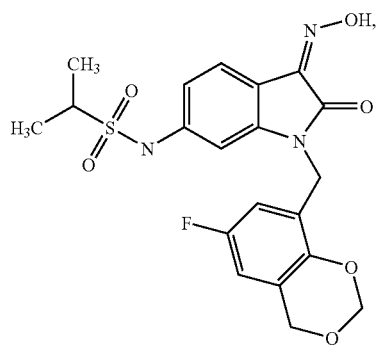
264
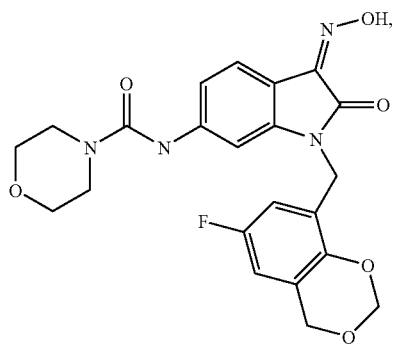
268
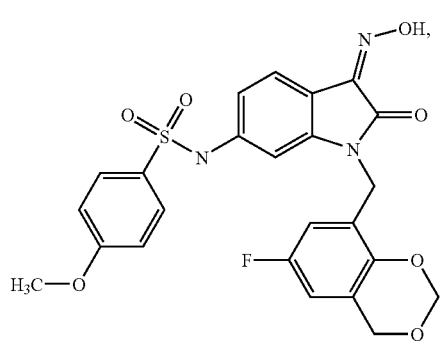
265
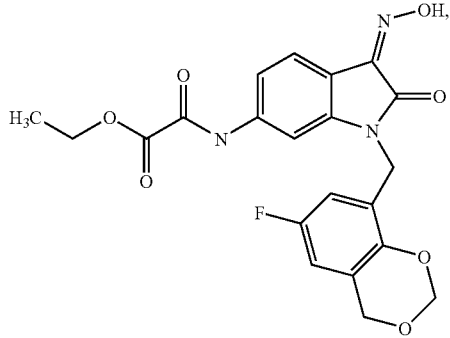
269
270

271 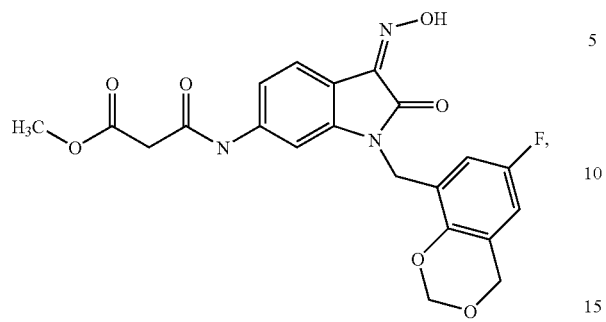
275 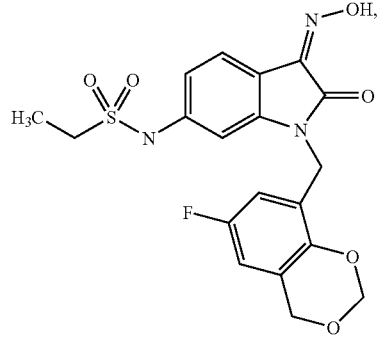
272 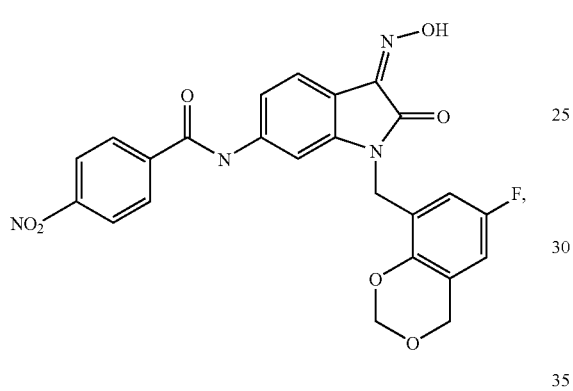
276 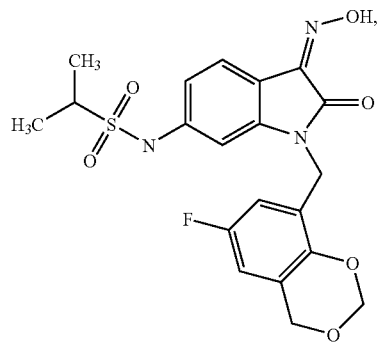
273 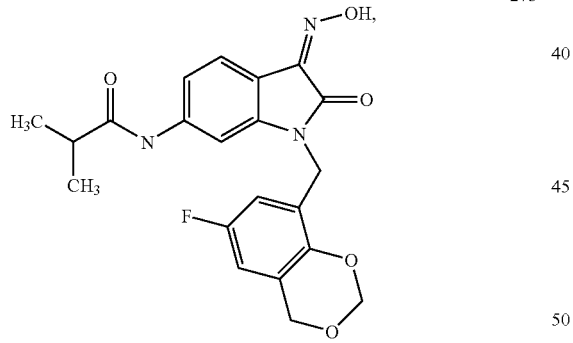
277 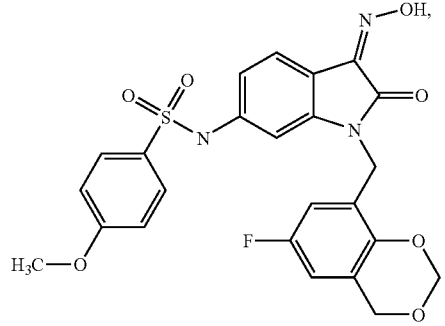
274 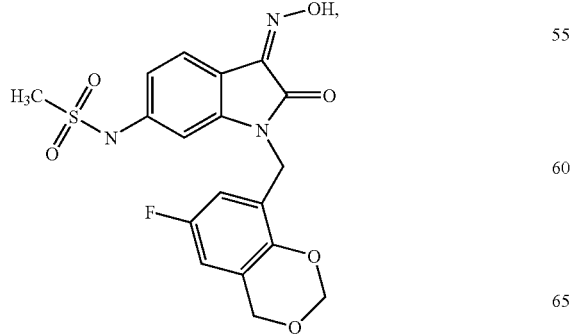
278 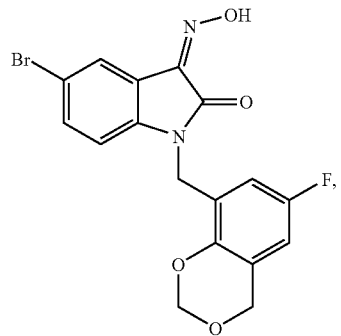

-continued
| | |
|---|---|
| 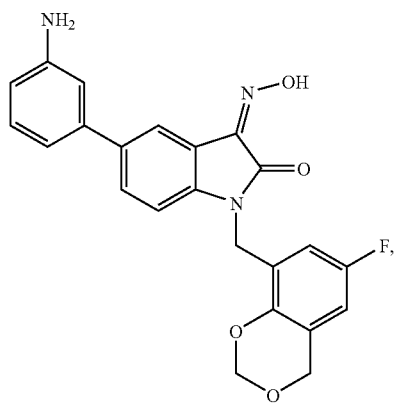 | 280 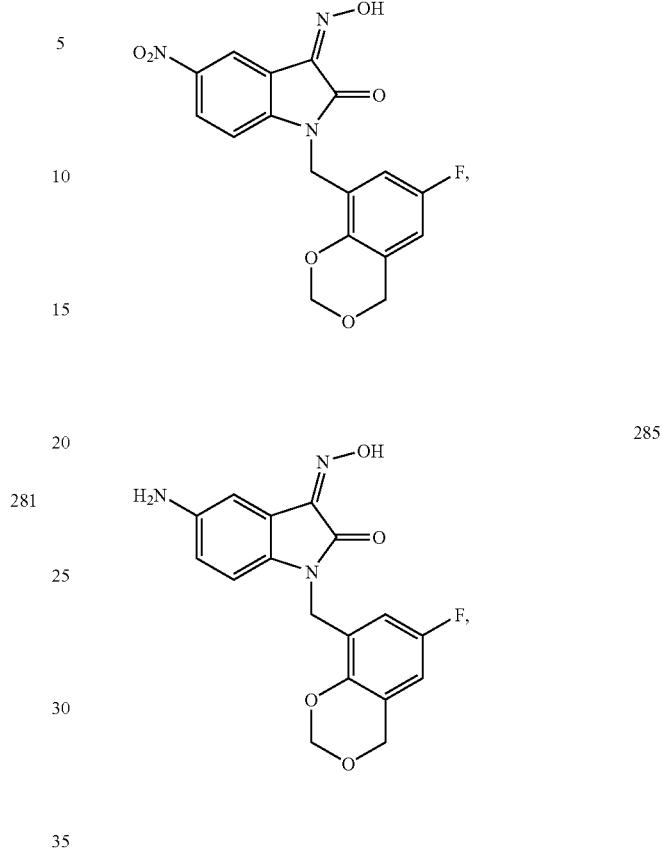 284 |
| 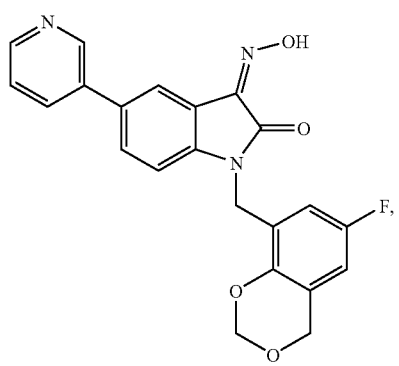 281 | 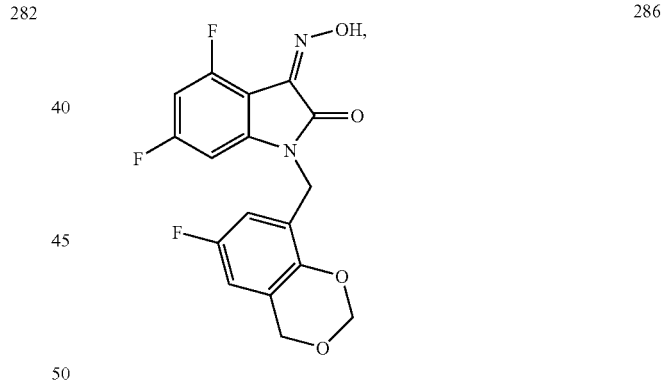 285 |
| 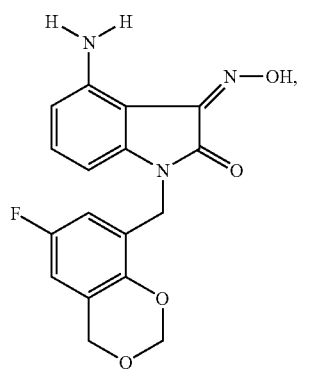 282 | 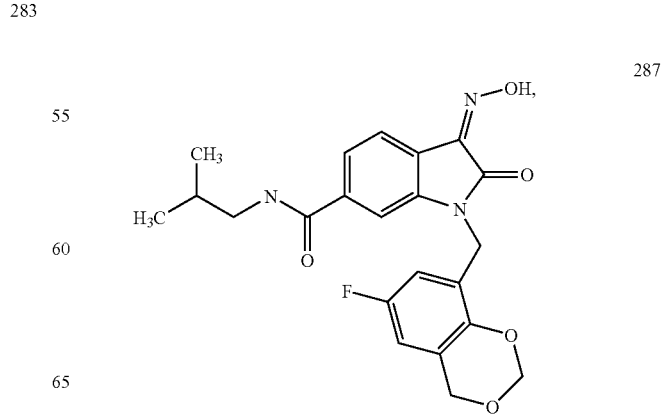 286 |
| 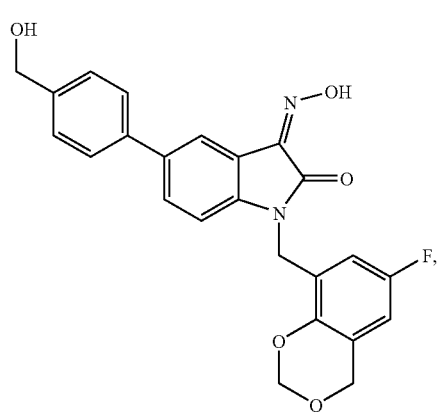 283 | 287 |

288
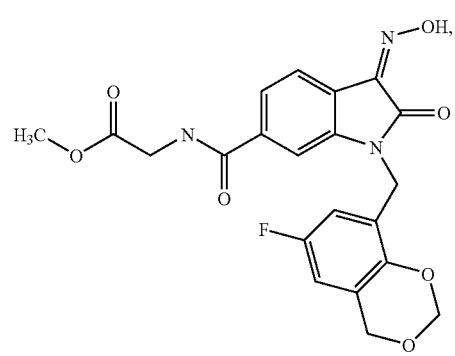
289
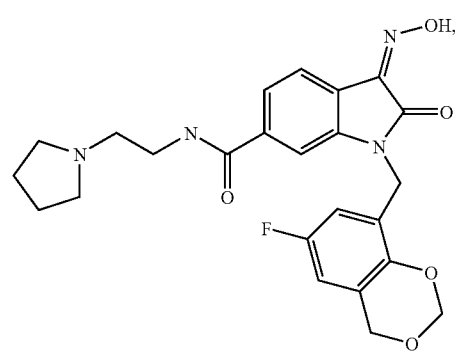
290
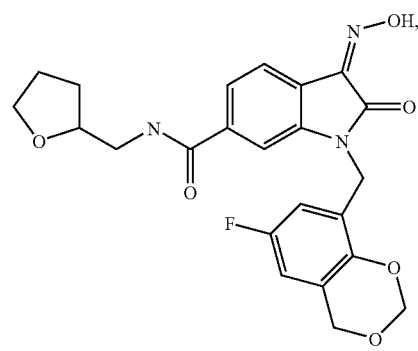
291
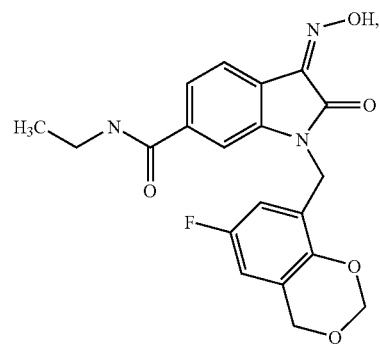
292
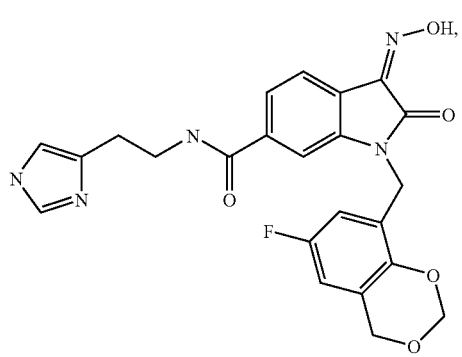
293
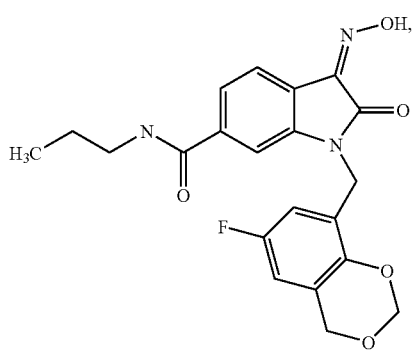
294
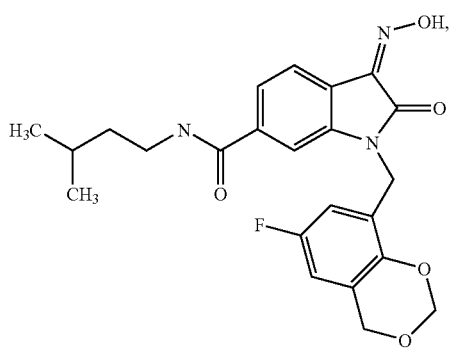
295
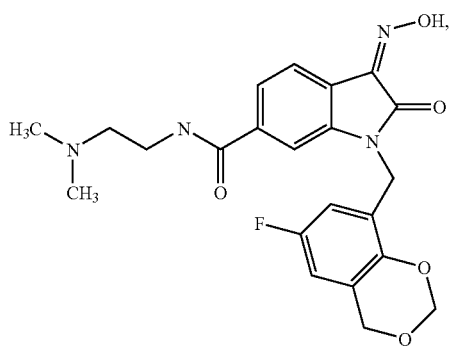

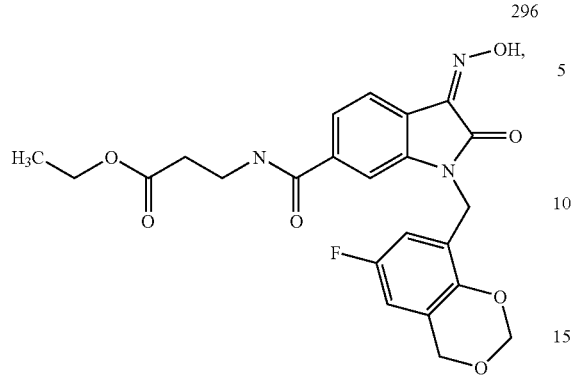
296
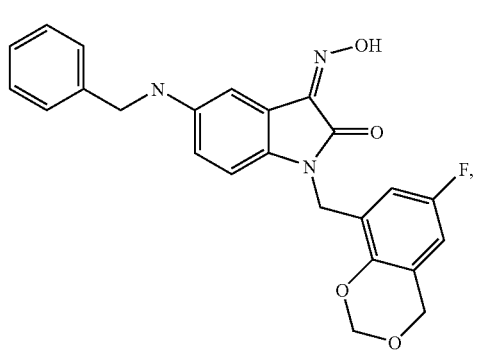
300
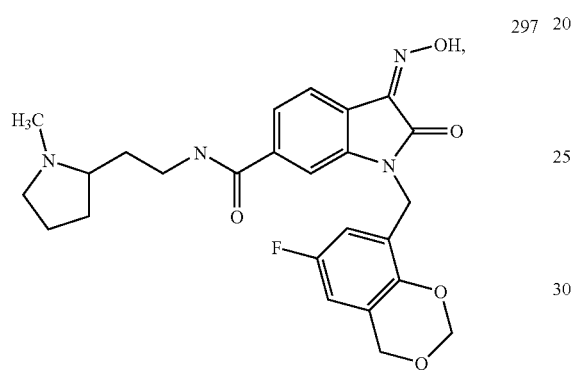
297
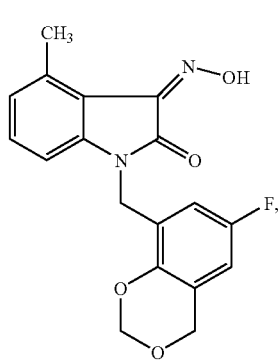
301
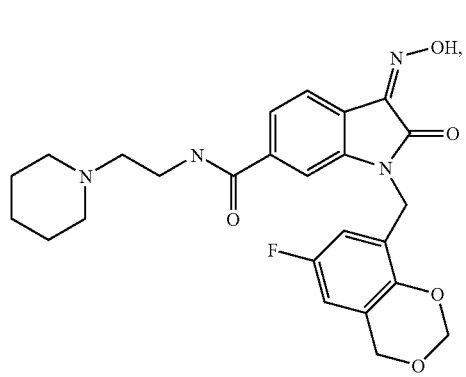
298
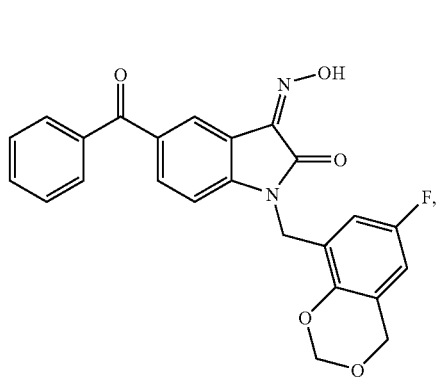
302
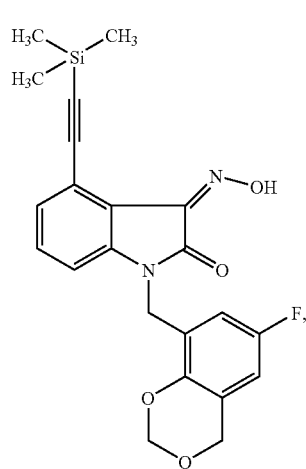
299
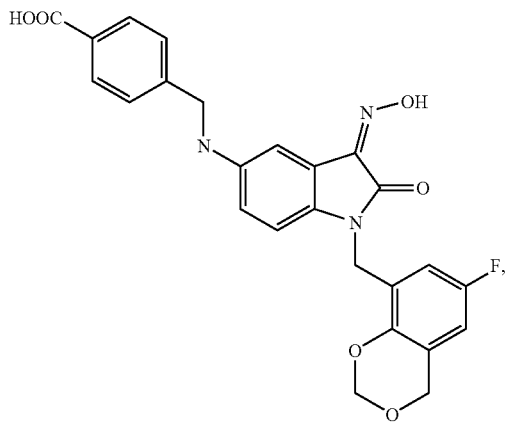
303

-continued
304
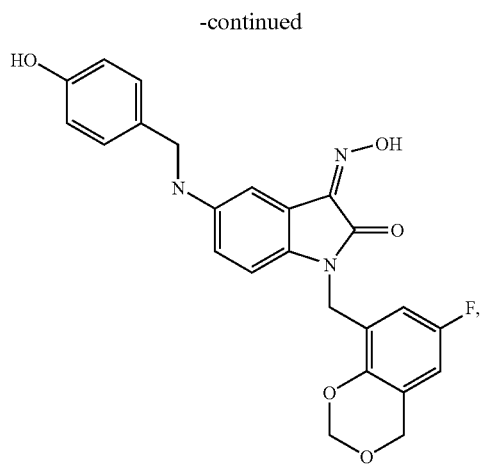
305
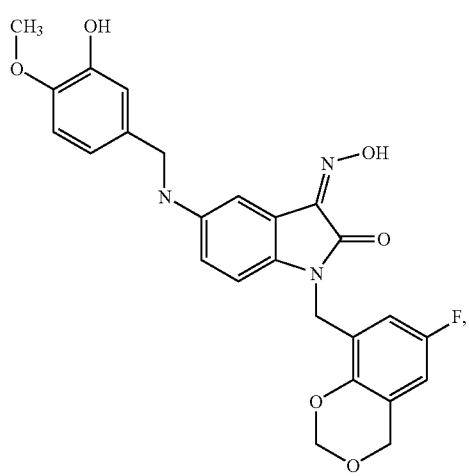
306
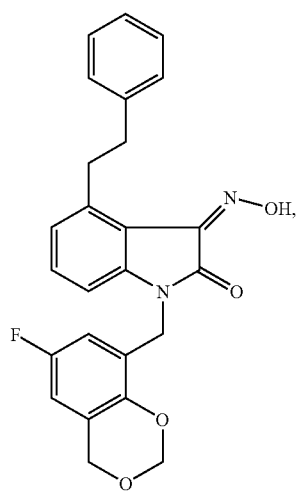
-continued
307
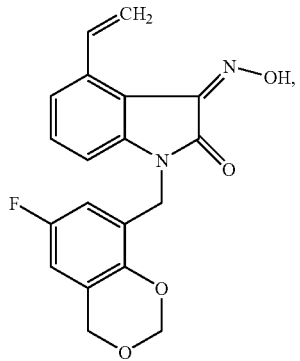
308
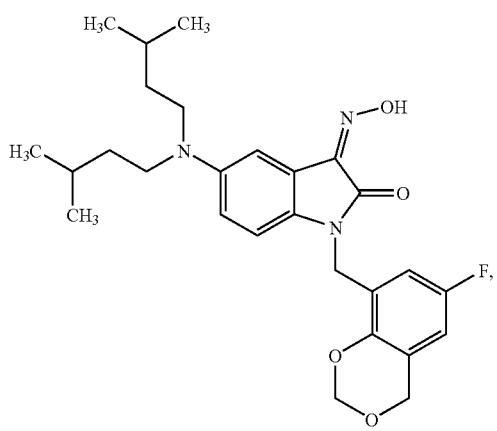
309
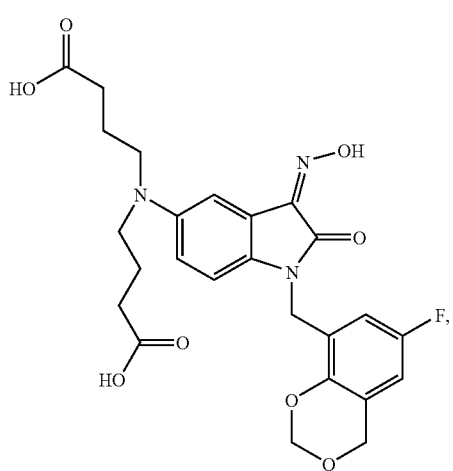

247
-continued
310 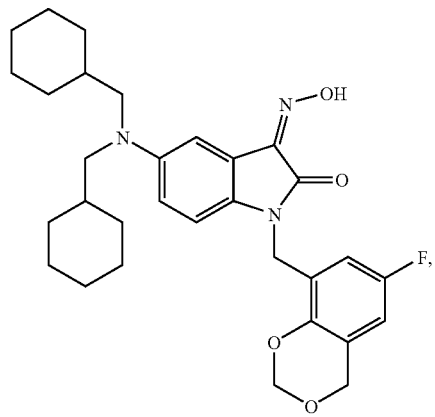
311 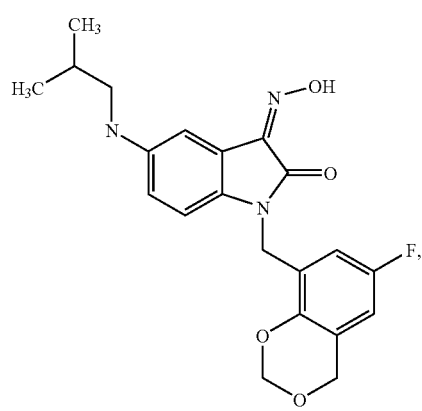
312 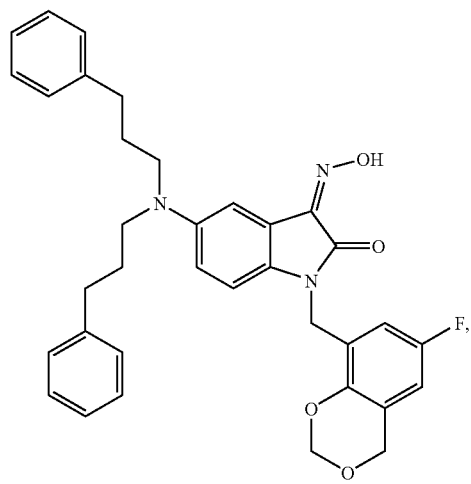
313 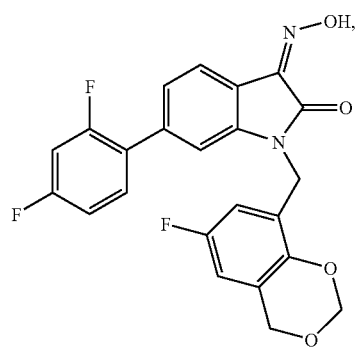
248
-continued
314 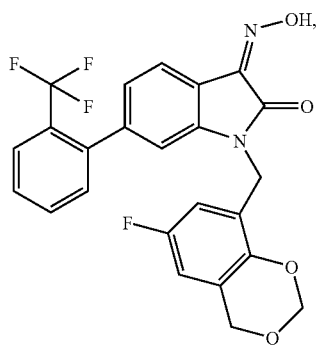
315 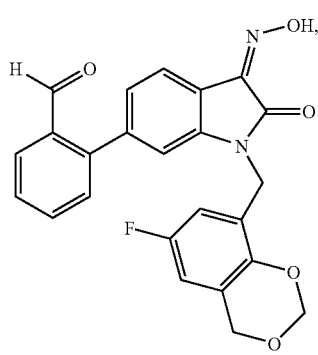
316 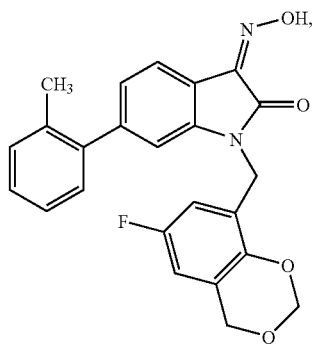
318 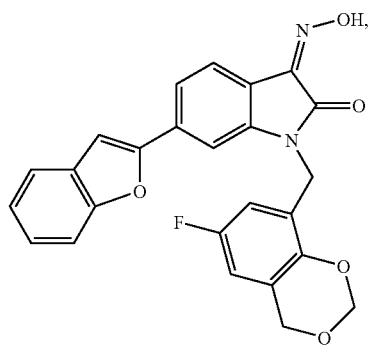

319 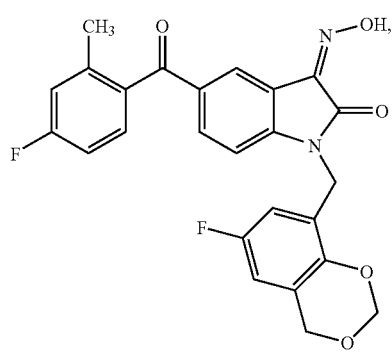
320 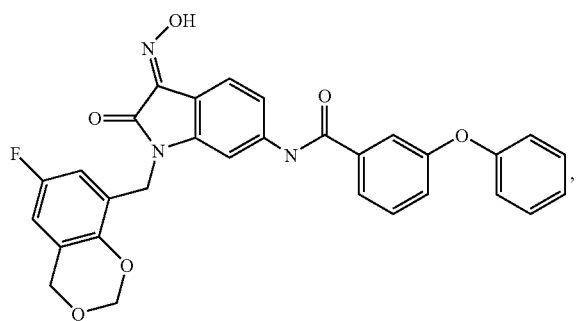
321 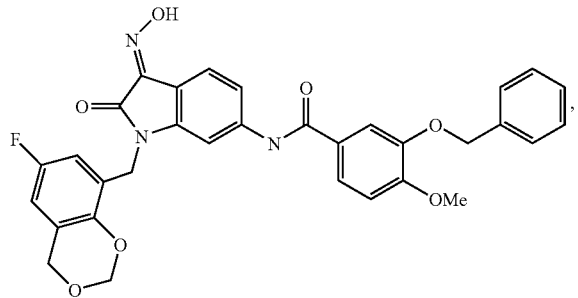
322 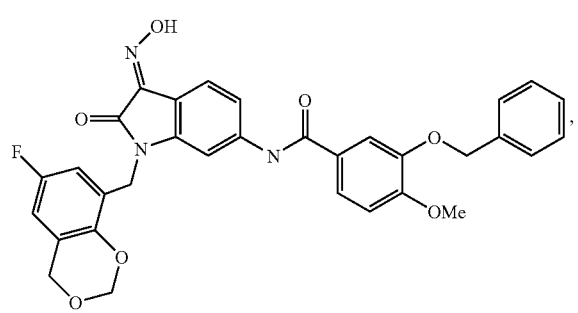
323 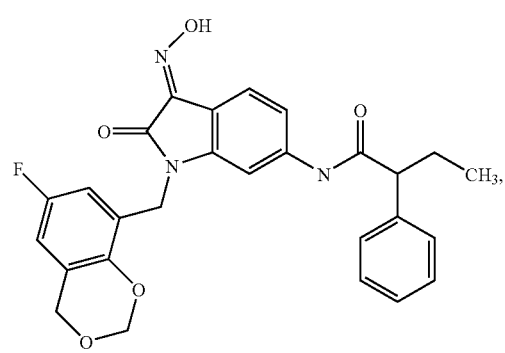
324 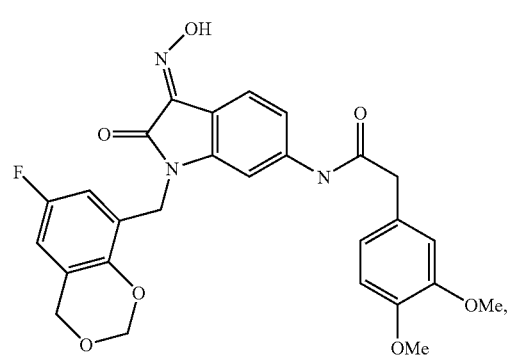
325 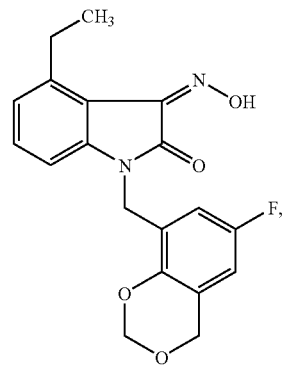
326 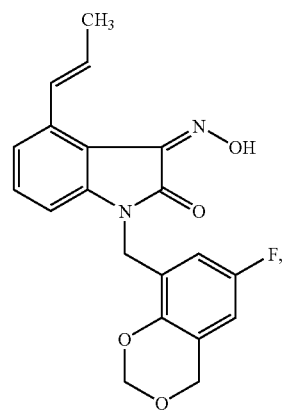

-continued
327
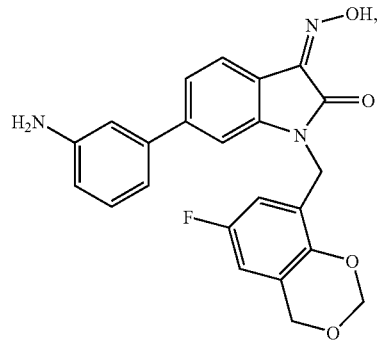
328
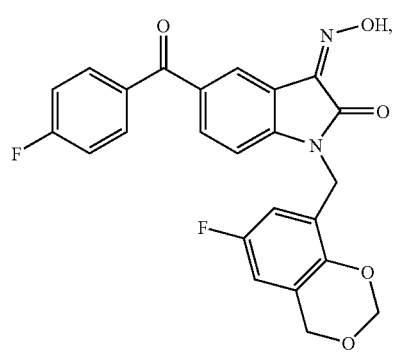
329
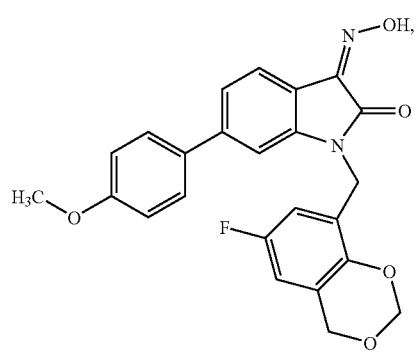
330
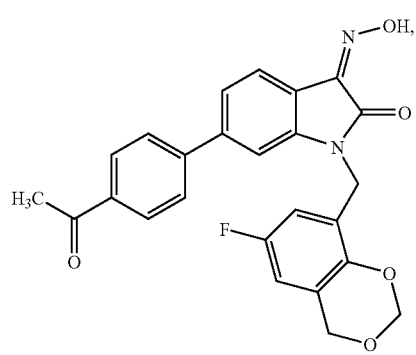
-continued
331
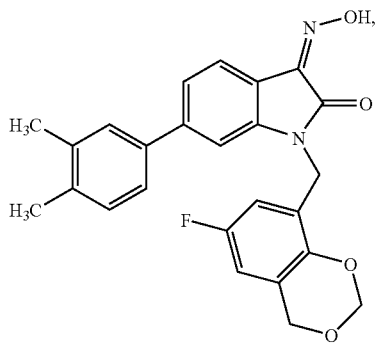
332
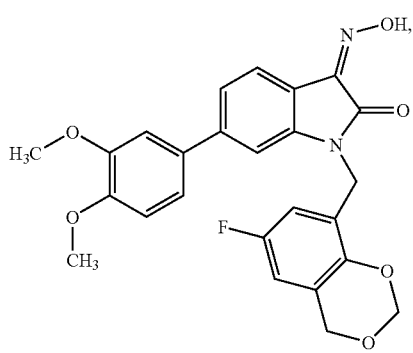
333
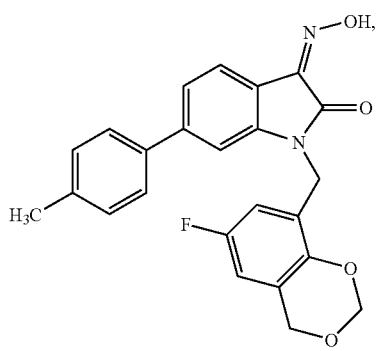
334
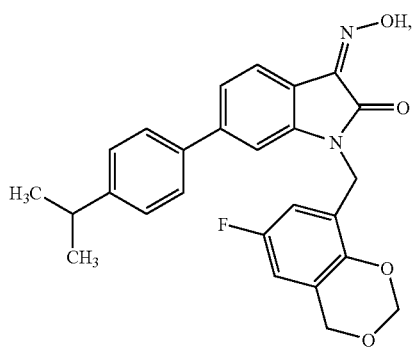

253
-continued
335
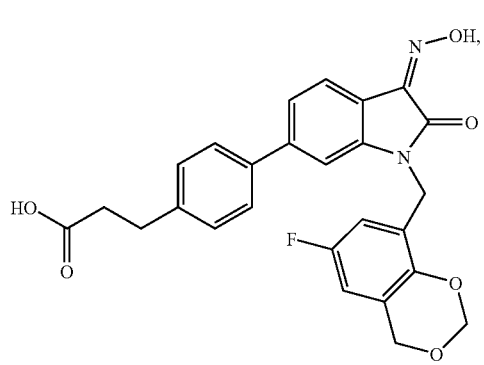
336
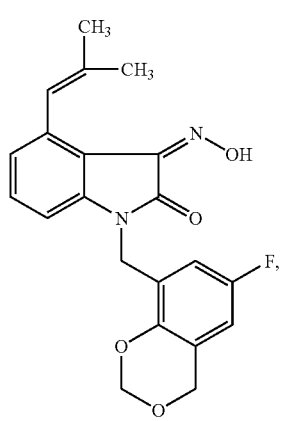
337
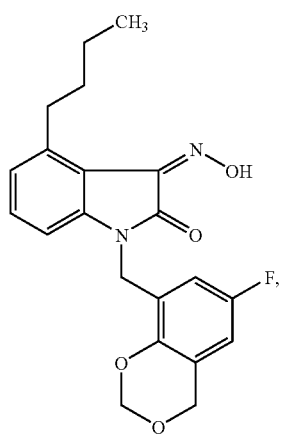
338
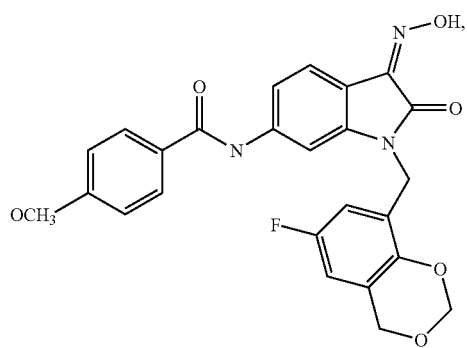
254
-continued
339
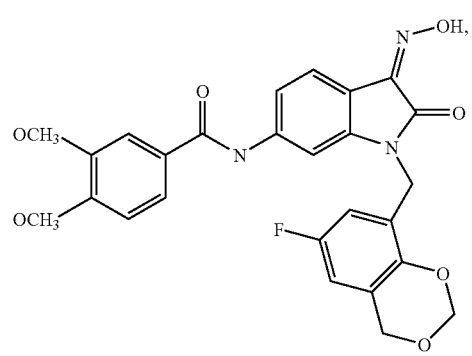
340
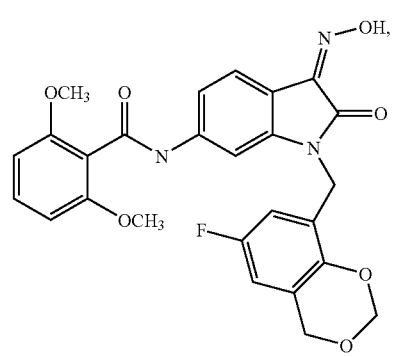
341
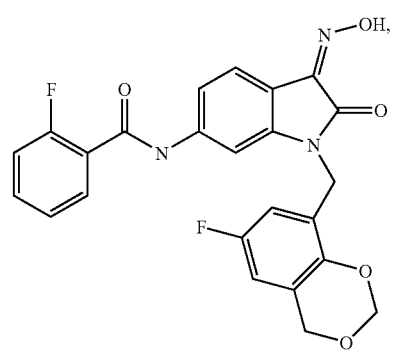
342
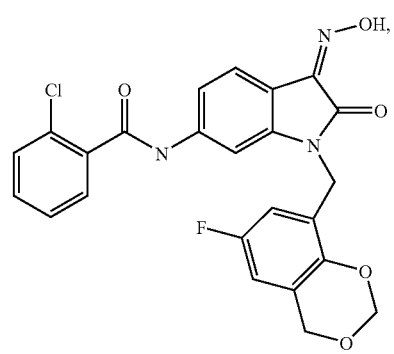

-continued
343
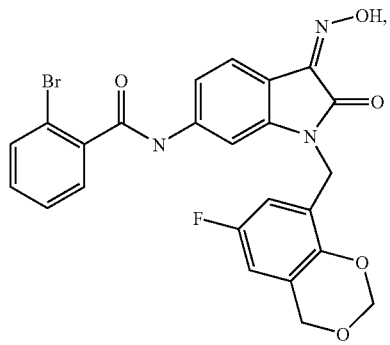
344
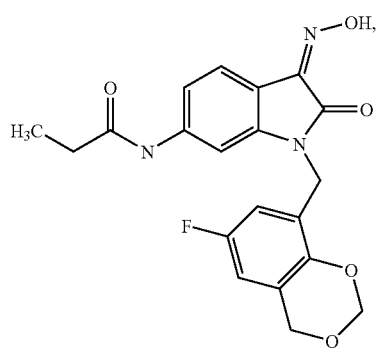
345
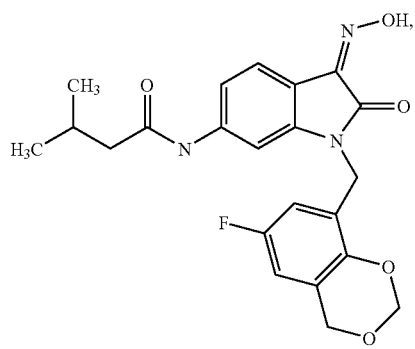
346
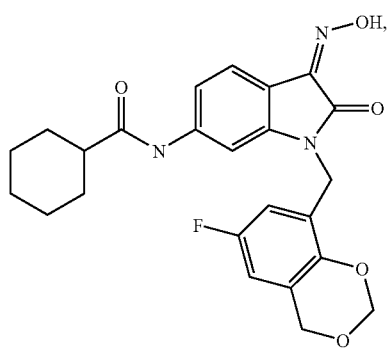
-continued
348
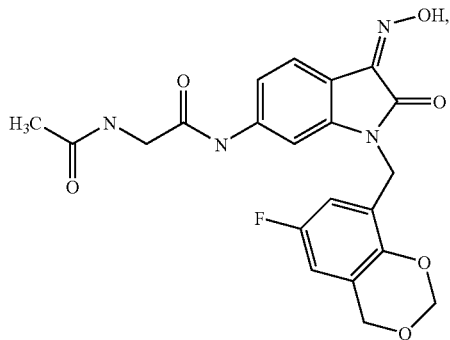
349
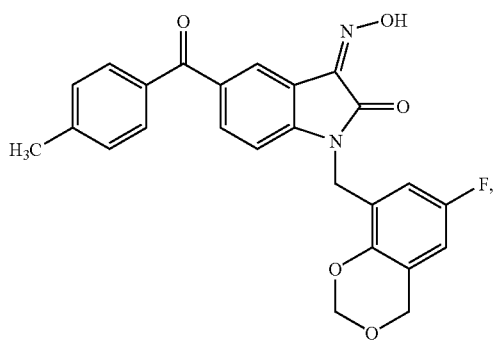
350
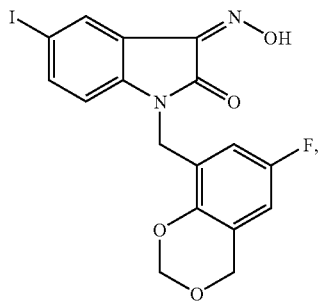
351

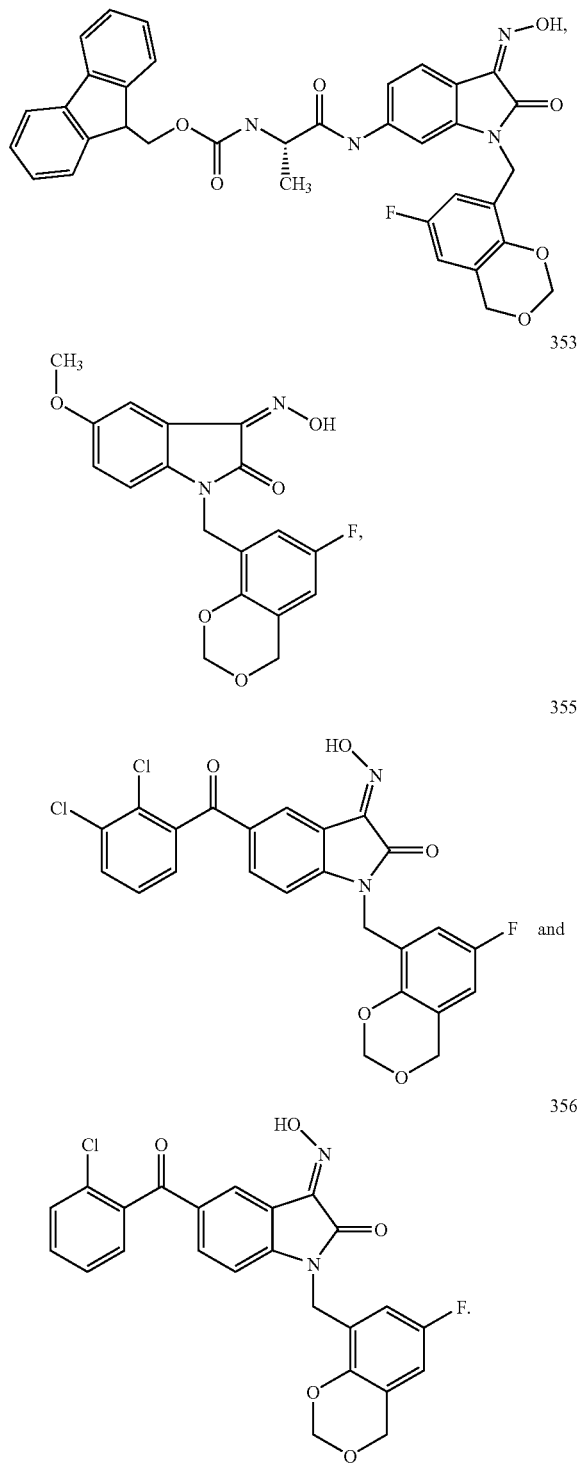

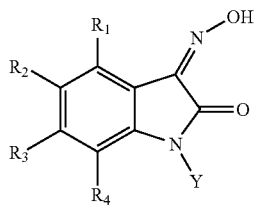

12. A pharmaceutical composition comprising a compound according to either of claims 1 or 11 and a pharmaceutically acceptable carrier.

13. A method for treating Parkinson's disease in a patient in need thereof, comprising administering the pharmaceutical composition of claim 12 to the patient.

14. A compound of the formula:

or a pharmaceutically acceptable salt thereof; wherein

Y is —($CH_2$)-$Q_1$;

$Q_1$ is benzodioxanyl, a substituted phenyl group, a substituted 5-7 membered aromatic heterocyclic ring, a 10-membered heterocyclic bicyclic ring, or a straight chain alkyl group substituted with phenyl or a heterocyclic monocyclic or bicyclic ring, wherein said phenyl or heterocyclic ring is substituted with one to four substituents, each of which is independently selected from $NH_2$, NH—R, N(R)$_2$, $NO_2$, OH, OR, $CF_3$, halo, CN, $CO_2$H, C(O)—$NH_2$, C(O)—NH—R, C(O)—N(R)$_2$, C(O)—R, SR, S(O)—R, S(O)$_2$—R, S(O)$_2$—NH—R or —R;

$R^1$ is $R^5$;

$R^2$ is $OCF_3$, $NH_2$, $R^5$, NH(CO)—$R^6$, NH($SO_2$)—$R^6$, —NH$CH_2R^5$, CO-$Q_1$ or CONH-$Q_1$;

$R^3$ is NH(CO)—$R^6$, NH($SO_2$)—$R^6$, CONH-$Q_1$, H, halo, methyl, $CF_3$, substituted or unsubstituted phenyl, a substituted or unsubstituted aromatic heterocyclic ring, an aromatic bicyclic ring, $NO_2$ or $NH_2$;

$R^4$ is $R^5$;

$R^5$ and $R^6$ are each independently selected from H; N(R)$_2$, NHOH, $NO_2$, C(O)OR or halo; a $C_1$-$C_6$ straight chain or branched alkyl, alkenyl or alkynyl group; a 5-7 membered aromatic or non-aromatic carbocyclic or heterocyclic ring; or a 9-14 membered bicyclic or tricyclic aromatic or non-aromatic carbocyclic or heterocyclic ring; wherein said alkyl, alkenyl, ring or ring system is optionally substituted with one to four substituents, each of which is independently selected from $NH_2$, NHR, NHC(O)OR, N(R)$_2$, $NO_2$, OH, OR, $CF_3$, halo, CN, Si(R)$_3$, $CO_2$H, COOR, $CONH_2$, CONHR, CON(R)$_2$, COR, SR, S(O)R, S(O)$_2$R, S(O)$_2$NHR or R; and R is a $C_1$-$C_6$ straight chain or branched alkyl or alkenyl group, a 5-7 membered aromatic or non-aromatic carbocyclic or heterocyclic ring, or a 9-10 membered bicyclic aromatic or non-aromatic carbocyclic or heterocyclic ring system.

15. The compound according to claim 14, wherein $R^1$ is H, methyl, halo, an optionally substituted phenyl, a monocyclic or bicyclic heterocycle, a substituted or unsubstituted alkyl, alkenyl or alkynyl, or COOR.

16. The compound according to claim 4, wherein $R^2$ is H, halo, $NO_2$, $NH_2$, methyl, $OCF_3$, —N(R)$_2$, or substituted phenyl.

17. The compound according to claim 14, wherein $R^3$ is H, halo, methyl, $CF_3$, substituted or unsubstituted phenyl, an aromatic heterocyclic ring, a bicyclic ring, $NO_2$ or $NH_2$.

18. The compound according to claim 14, wherein $R^4$ is H or methyl.

19. The compound according to claim 14, wherein $Q_1$ is a substituted phenyl group.

20. The compound according to claim 14, wherein said compound is selected from the group consisting of:
1
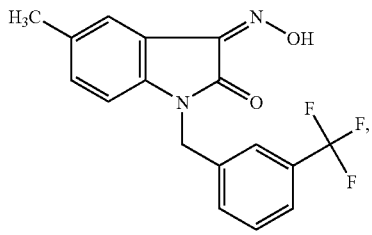
2
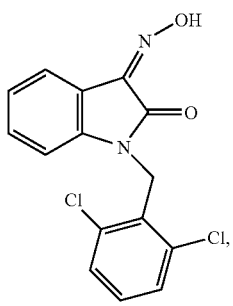
3
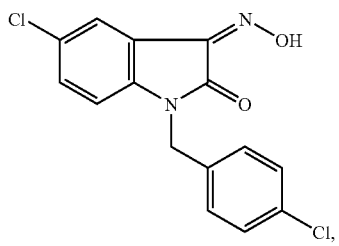
4
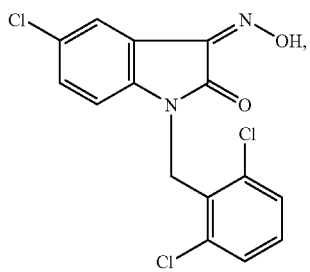
5
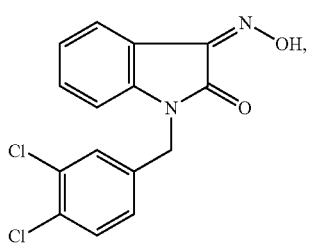
-continued
6
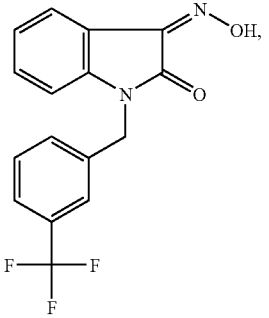
7
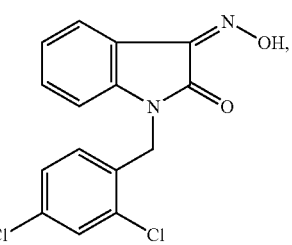
8
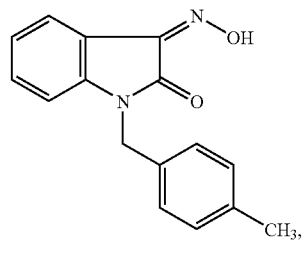
9
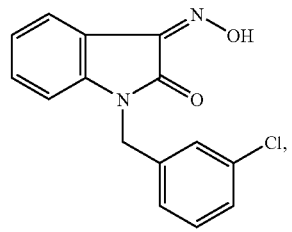
10
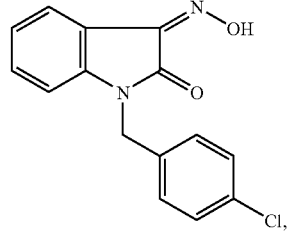
11
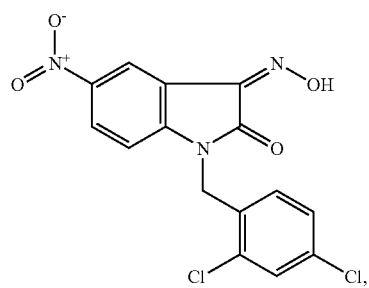

-continued
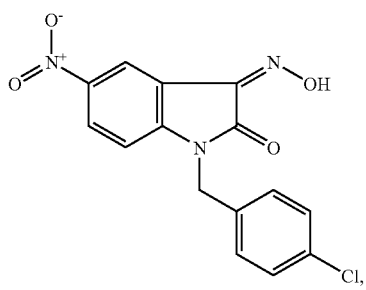
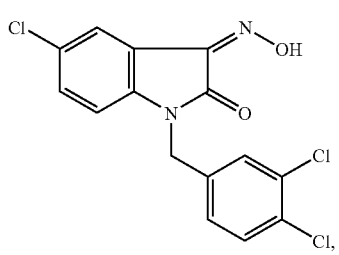
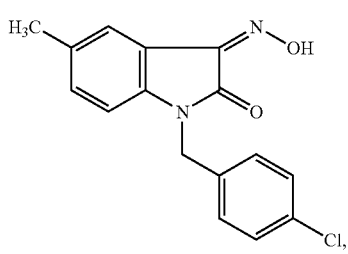
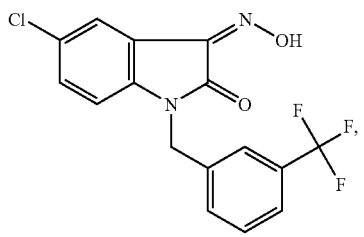
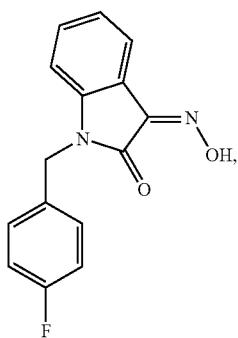
-continued
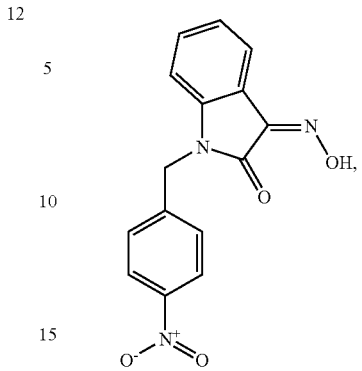
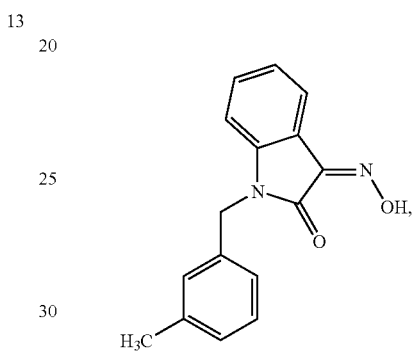
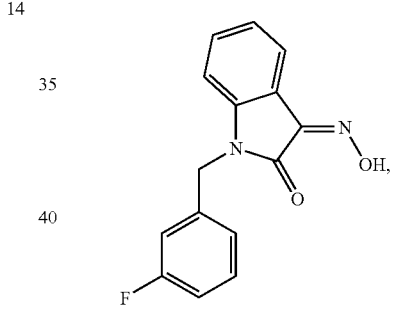
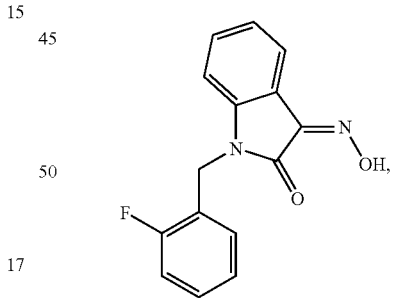
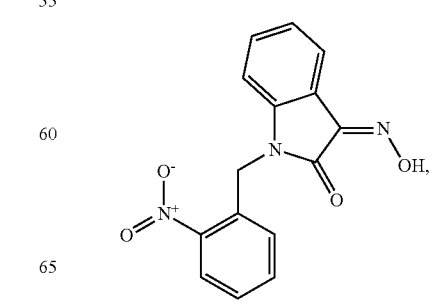

24
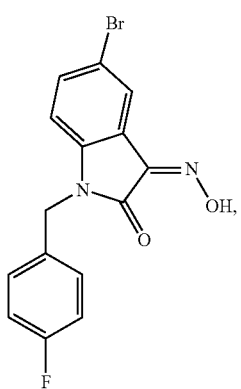
25
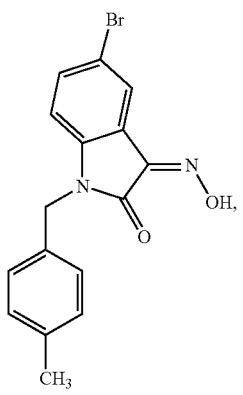
26
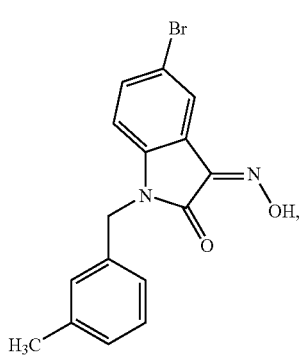
27
28
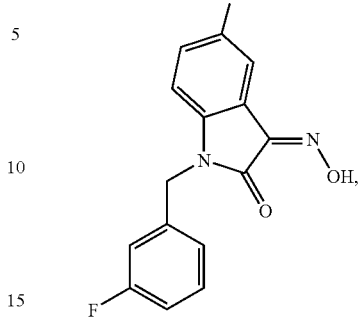
29
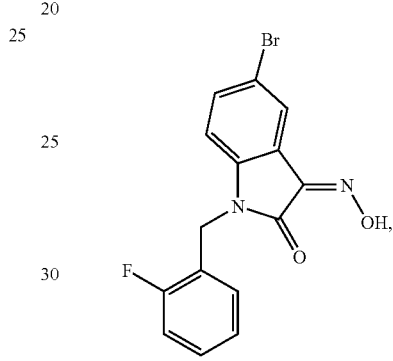
30
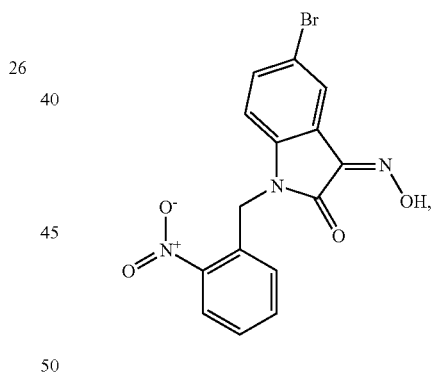
32
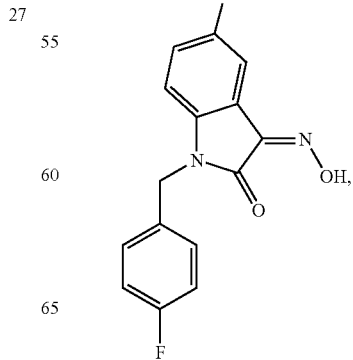

-continued

33

34

35

36

-continued

38

39

40

41

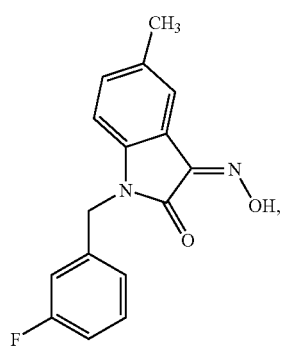
42
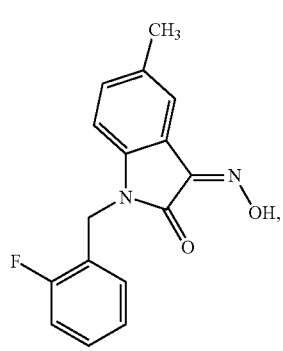
43
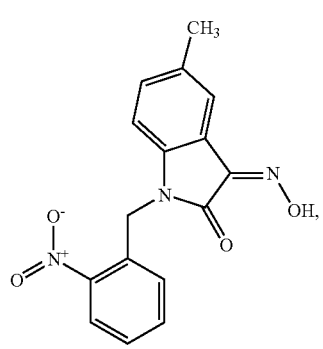
44
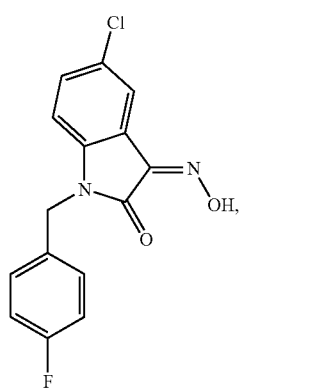
46
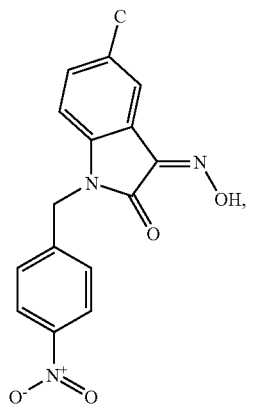
47
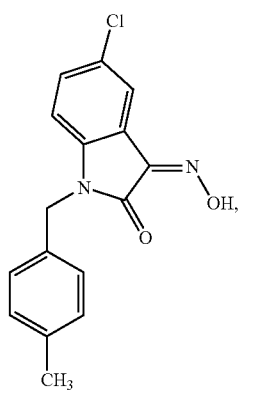
48
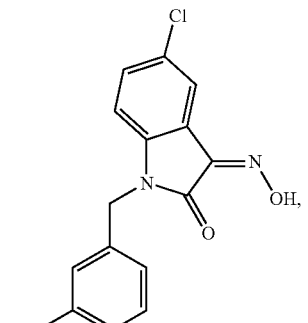
49
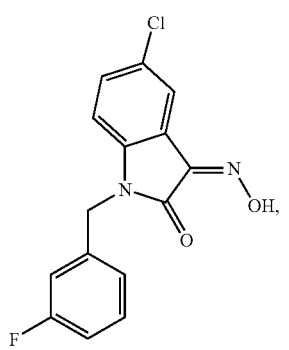
50

-continued
51
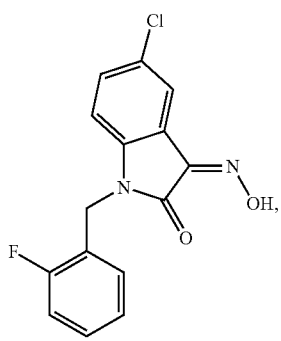
52
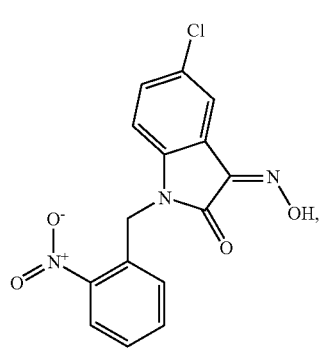
54
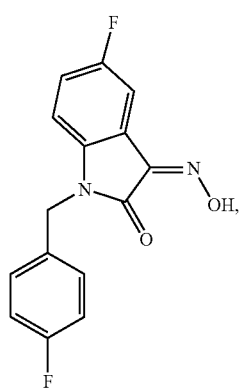
55
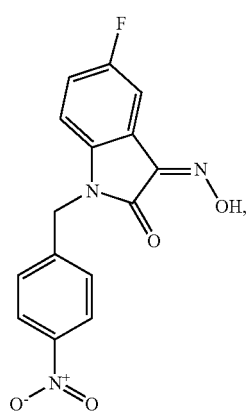
-continued
56
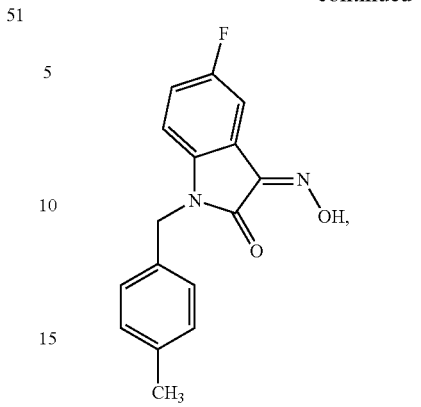
57
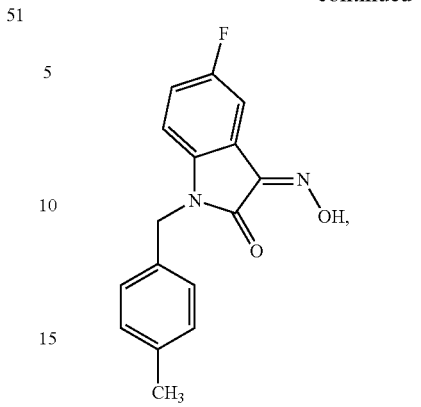
58
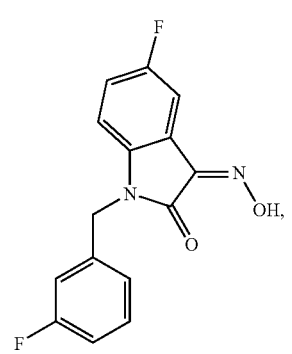
59
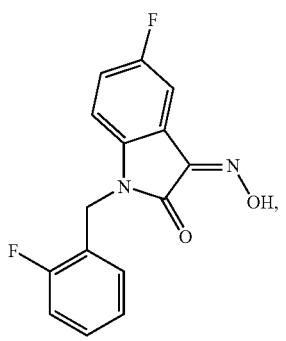

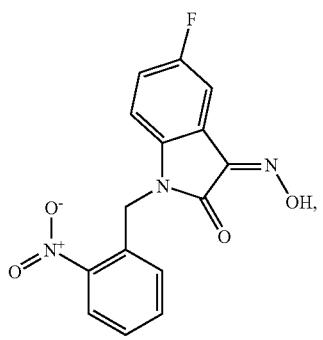
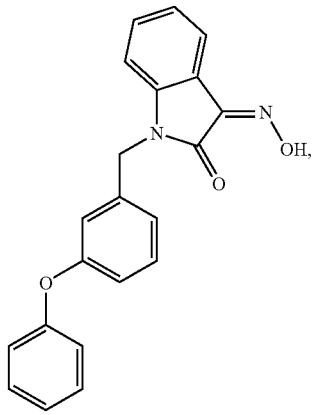
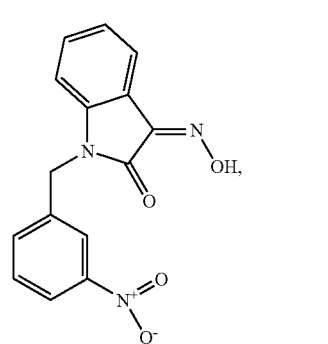
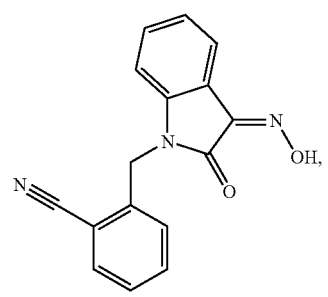
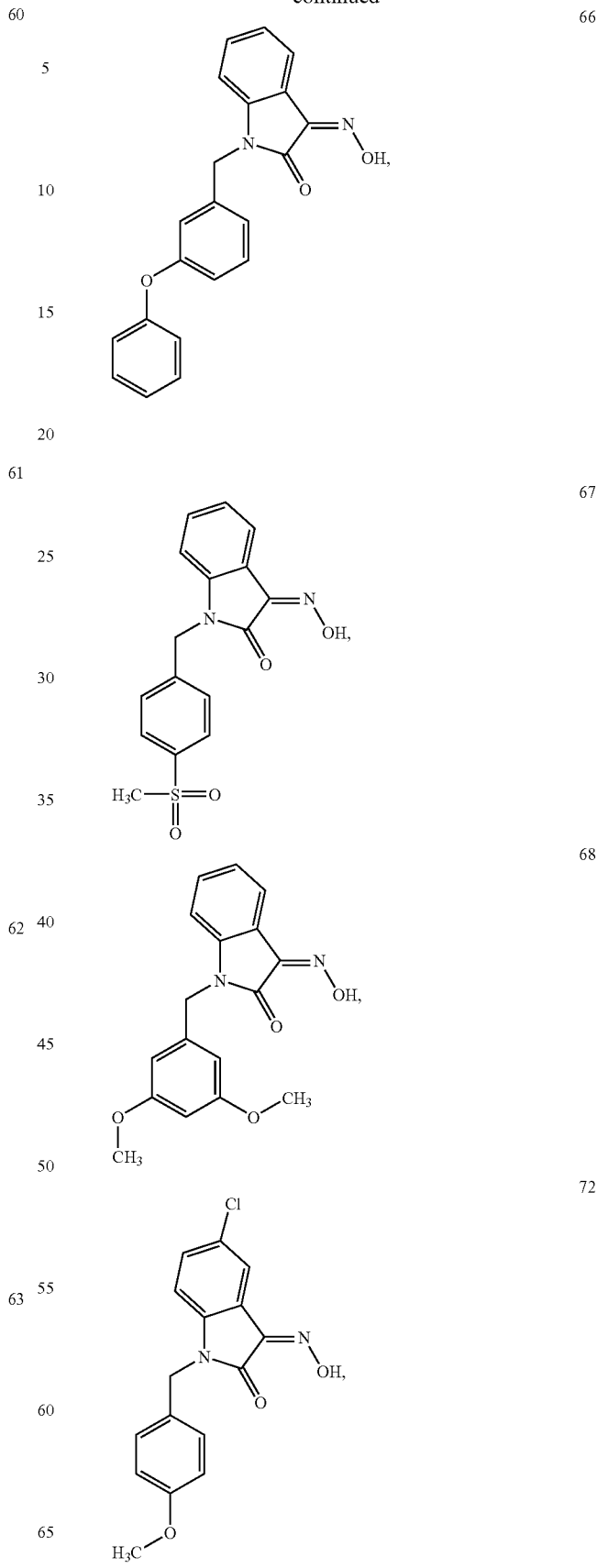

| 73 | 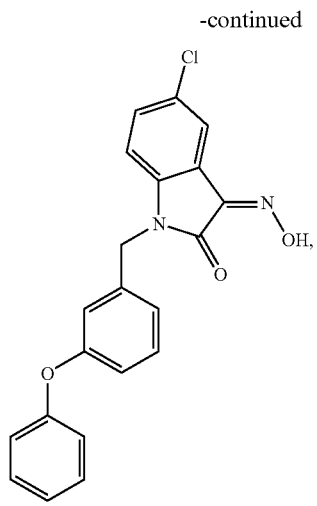 | 80 | 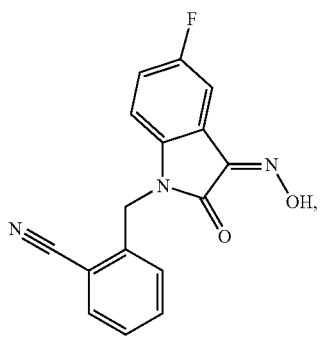 |
| 74 | 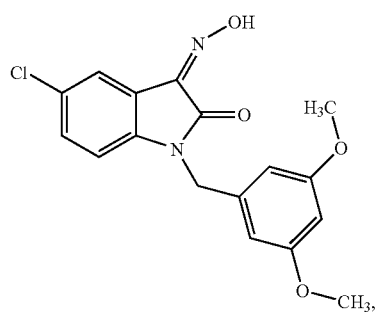 | 82 | 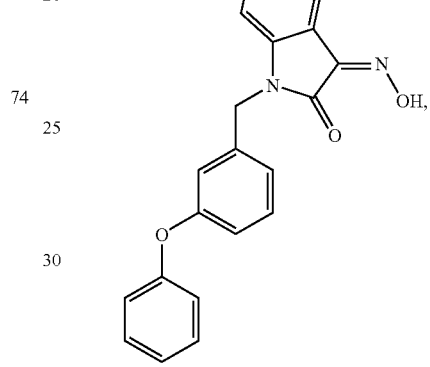 |
| 78 | 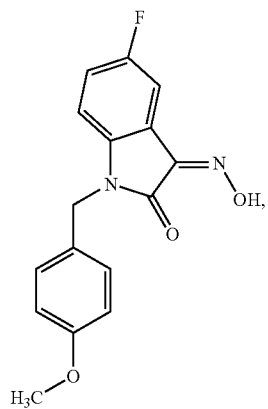 | 83 | 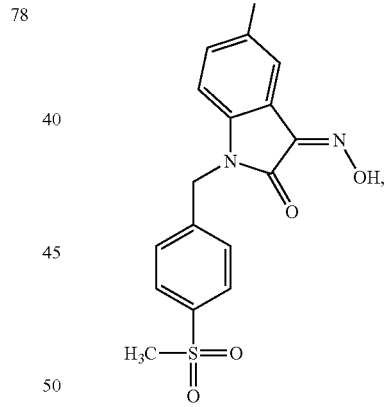 |
| 79 | 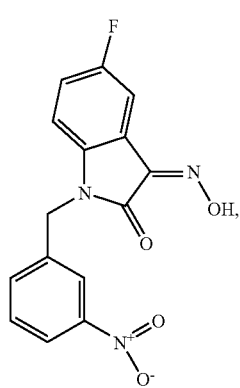 | 84 | 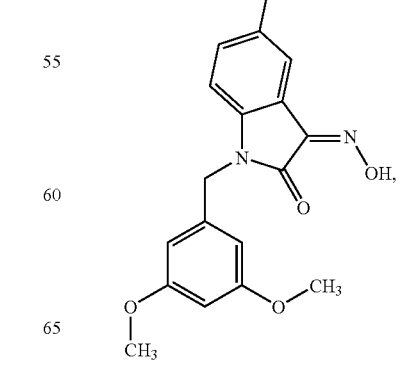 |

87
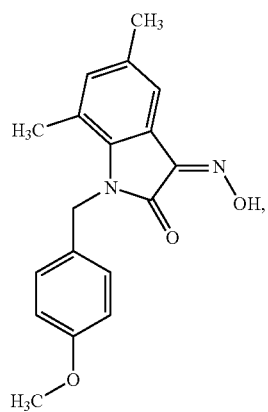
88
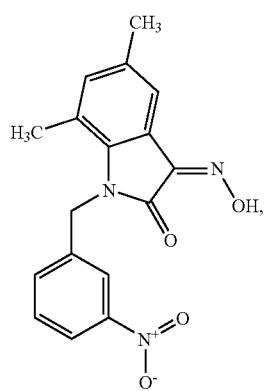
89
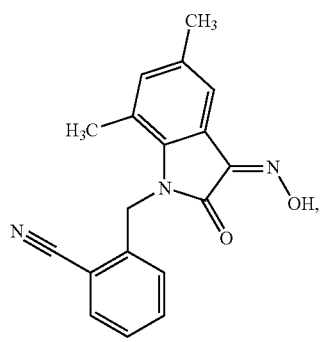
92
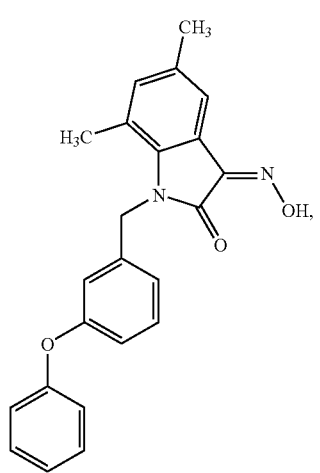
93
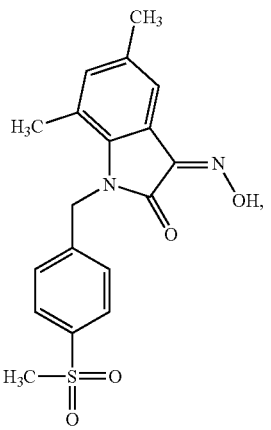
94
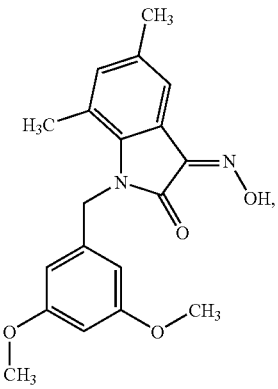
97
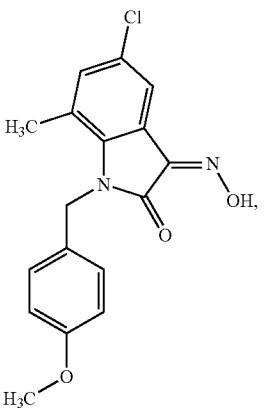
98
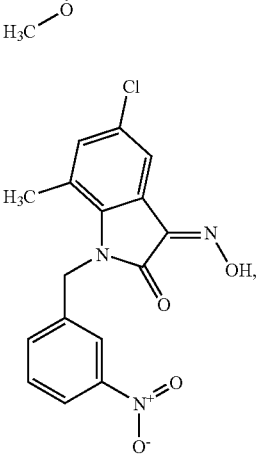

-continued
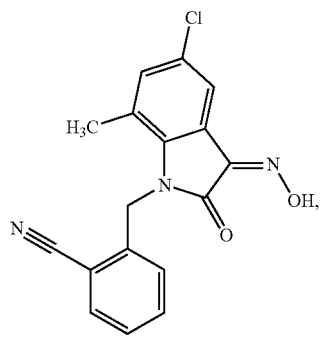
99
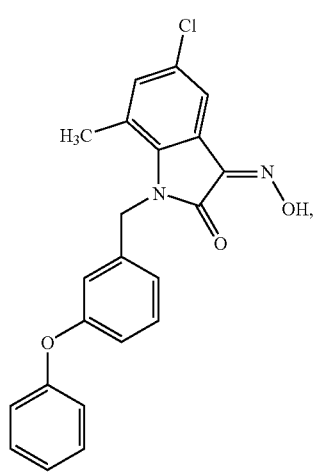
100
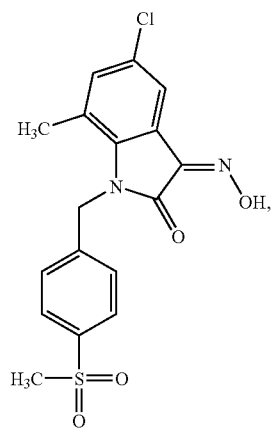
101
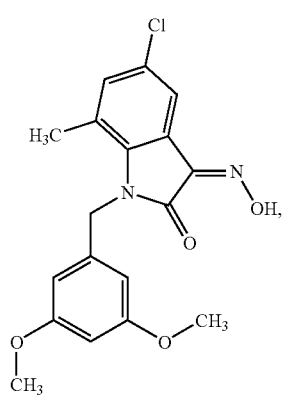
102

-continued
121
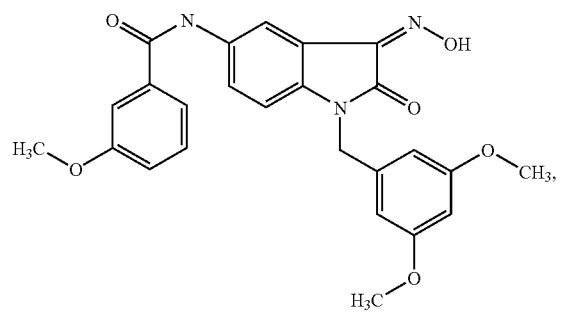
140
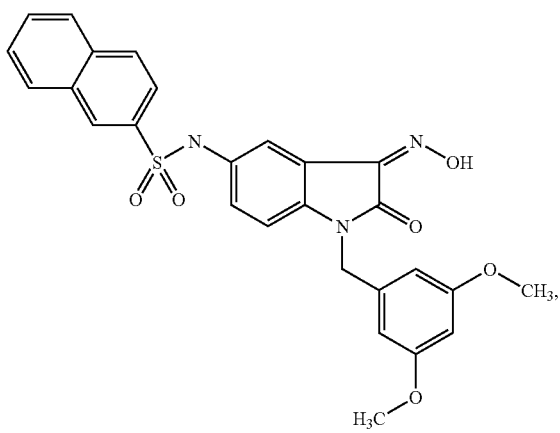
131
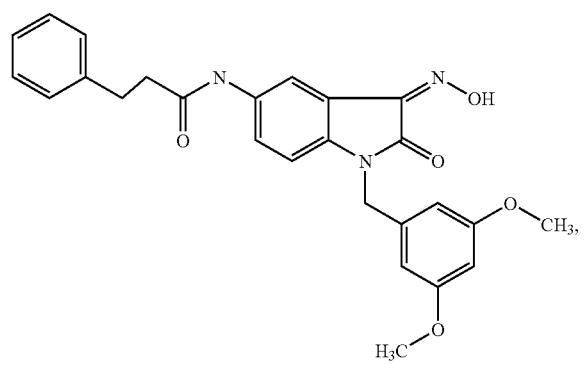
143
134
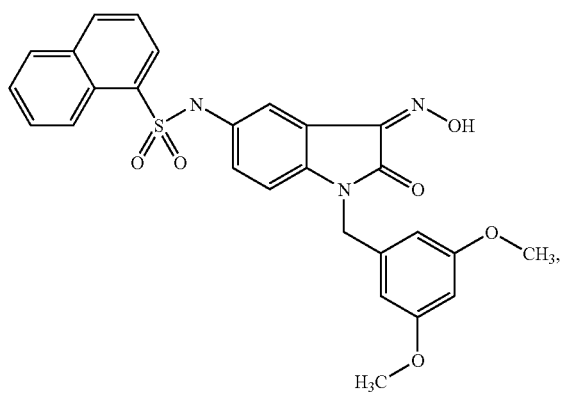
145
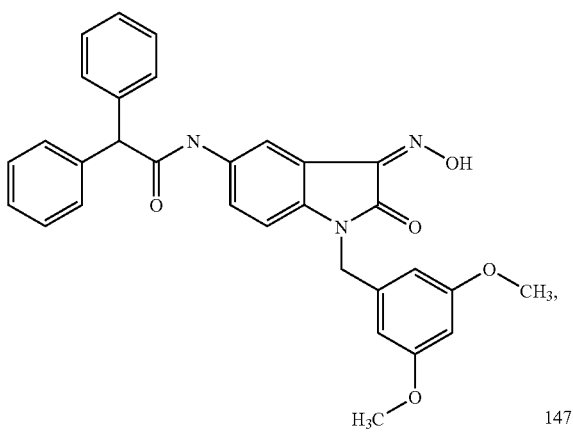
137
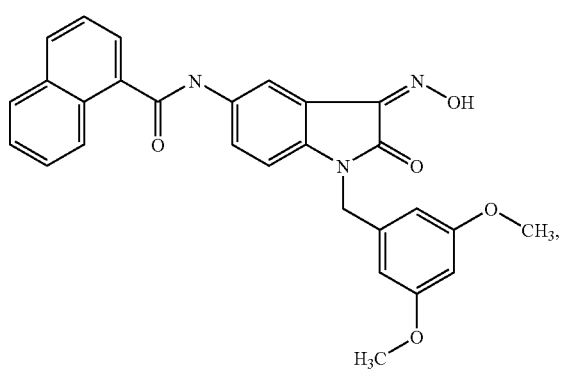
147

150
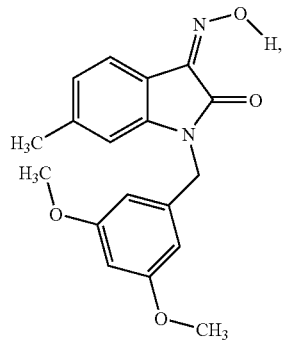
151
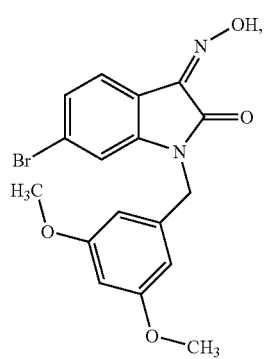
162
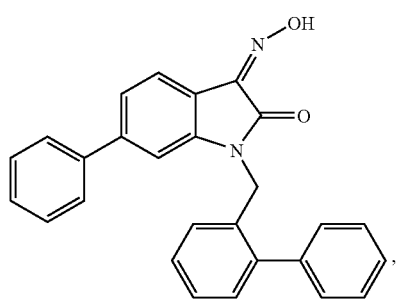
164
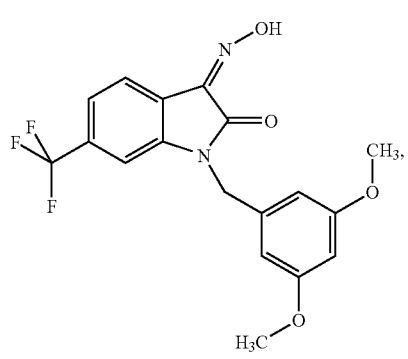
166
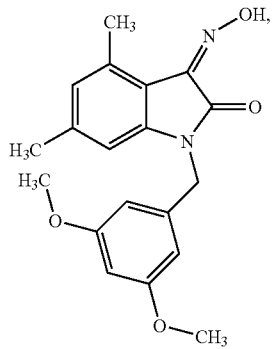
171
180
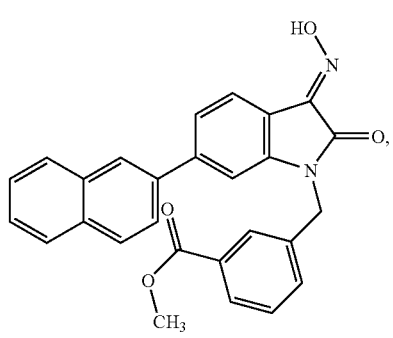

-continued
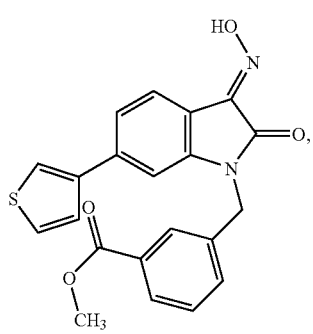
185
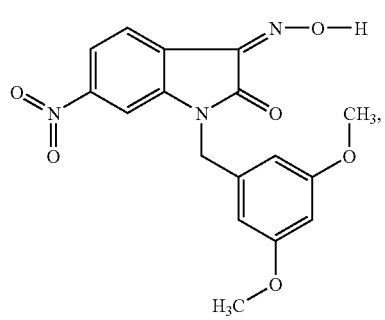
198
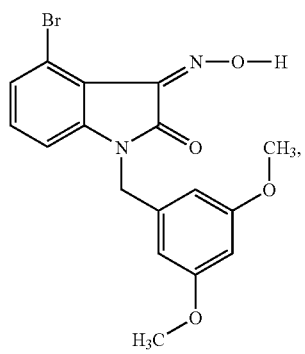
199
-continued
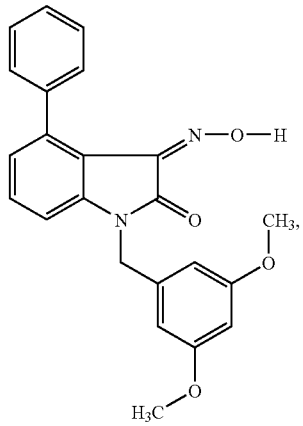
200
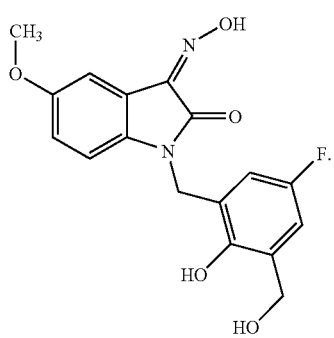
354
and
21. A pharmaceutical composition comprising a compound according to either of claims 14 or 20 and a pharmaceutically acceptable carrier.
22. A method for treating Parkinson's disease in a patient in need thereof, comprising administering the pharmaceutical composition of claim 21 to the patient.
* * * * *